(12) United States Patent
Okawa et al.

(10) Patent No.: US 7,283,247 B2
(45) Date of Patent: Oct. 16, 2007

(54) OPTICAL PROBE SYSTEM

(75) Inventors: Atsushi Okawa, Hachioji (JP); Akihiro Horii, Hachioji (JP); Tianyu Xie, Akiruno (JP); Mitsuhiro Hara, Musashino (JP)

(73) Assignee: Olympus Corporation, Tokyo (JP)

( * ) Notice: Subject to any disclaimer, the term of this patent is extended or adjusted under 35 U.S.C. 154(b) by 806 days.

(21) Appl. No.: 10/667,773

(22) Filed: Sep. 22, 2003

(65) Prior Publication Data
US 2004/0212808 A1 Oct. 28, 2004

(30) Foreign Application Priority Data
Sep. 25, 2002 (JP) ............................. 2002-279905
Oct. 2, 2002 (JP) ............................. 2002-290410
Sep. 9, 2003 (JP) ............................. 2003-317380

(51) Int. Cl.
G01B 9/02 (2006.01)
(52) U.S. Cl. .................. 356/477; 356/556; 356/479; 382/131
(58) Field of Classification Search ........ 382/128–132, 382/168–172, 266; 356/479, 511, 451; 600/407, 600/478; 348/65
See application file for complete search history.

(56) References Cited

U.S. PATENT DOCUMENTS

| 5,321,501 | A | * | 6/1994 | Swanson et al. ............ 356/479 |
| 5,459,570 | A | * | 10/1995 | Swanson et al. ............ 356/479 |
| 5,508,805 | A | * | 4/1996 | Muranishi et al. .......... 356/493 |
| 6,141,577 | A | * | 10/2000 | Rolland et al. ............ 600/407 |
| 6,501,551 | B1 | * | 12/2002 | Tearney et al. ............ 356/477 |
| 6,594,036 | B1 | * | 7/2003 | Wong et al. ............... 358/471 |
| 6,608,684 | B1 | * | 8/2003 | Gelikonov et al. .......... 356/479 |
| 6,615,072 | B1 | * | 9/2003 | Izatt et al. ................ 600/478 |
| 6,724,418 | B1 | * | 4/2004 | Takahashi .................. 348/65 |
| 6,760,110 | B2 | * | 7/2004 | Aoki et al. ................ 356/445 |
| 6,809,866 | B2 | * | 10/2004 | Xie et al. .................. 359/618 |
| 6,999,608 | B2 | * | 2/2006 | Toida ....................... 382/131 |
| 2002/0196334 | A1 | * | 12/2002 | Saito et al. ................ 348/65 |

FOREIGN PATENT DOCUMENTS

| JP | 2000-75210 | 3/2000 |
| JP | 2000-126115 | 5/2000 |
| JP | 2001-512606 | 8/2001 |
| JP | 2001-356273 | 12/2001 |

* cited by examiner

Primary Examiner—Joseph Mancuso
Assistant Examiner—Andrae Allison
(74) Attorney, Agent, or Firm—Scully, Scott, Murphy & Presser, P.C.

(57) ABSTRACT

An optical probe system comprises an optical probe that is inserted into a body cavity, a light source that generates light which is irradiated to an object, and a high-magnification observation unit included in the distal section of the optical probe. The optical probe system further comprises: an image digitization unit that digitizes a luminance signal produced by the high-magnification observation unit; an image parameter sampling unit that samples an image parameter from an image; an optimization parameter calculation unit that calculates an optimization parameter on the basis of the image parameter; an image optimization unit that optimizes an image according to the optimization parameter; an image display device on which an optimized image is displayed; and a digital image preservation unit in which a digitized image is preserved.

14 Claims, 37 Drawing Sheets

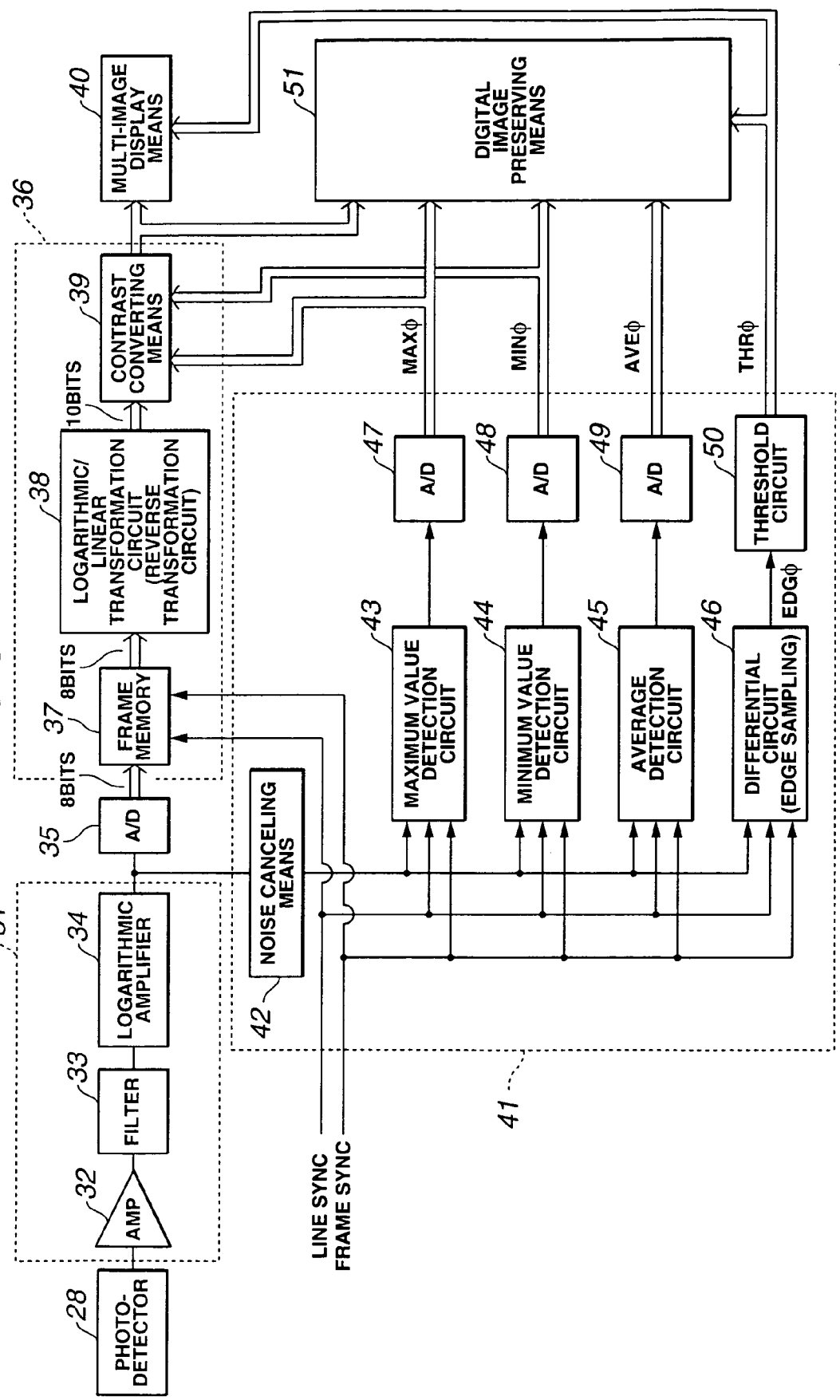

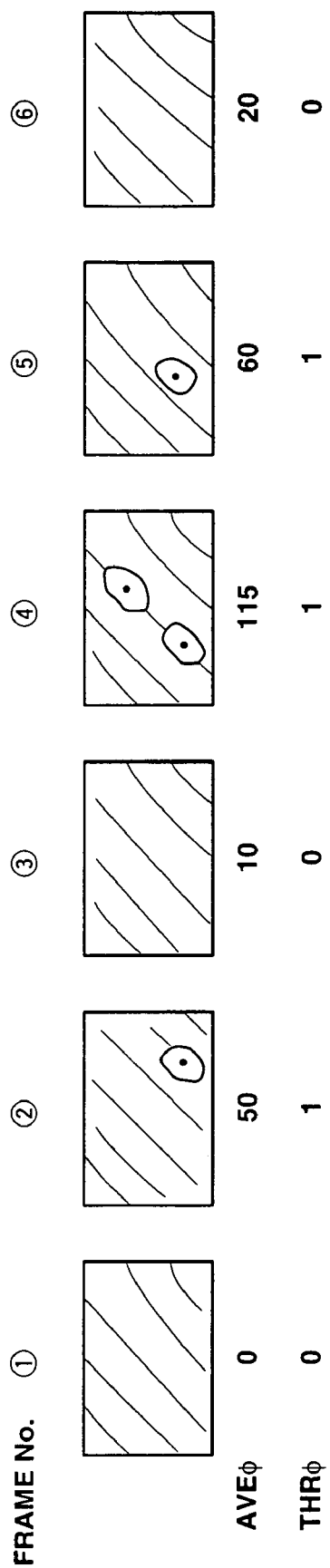
FIG.8
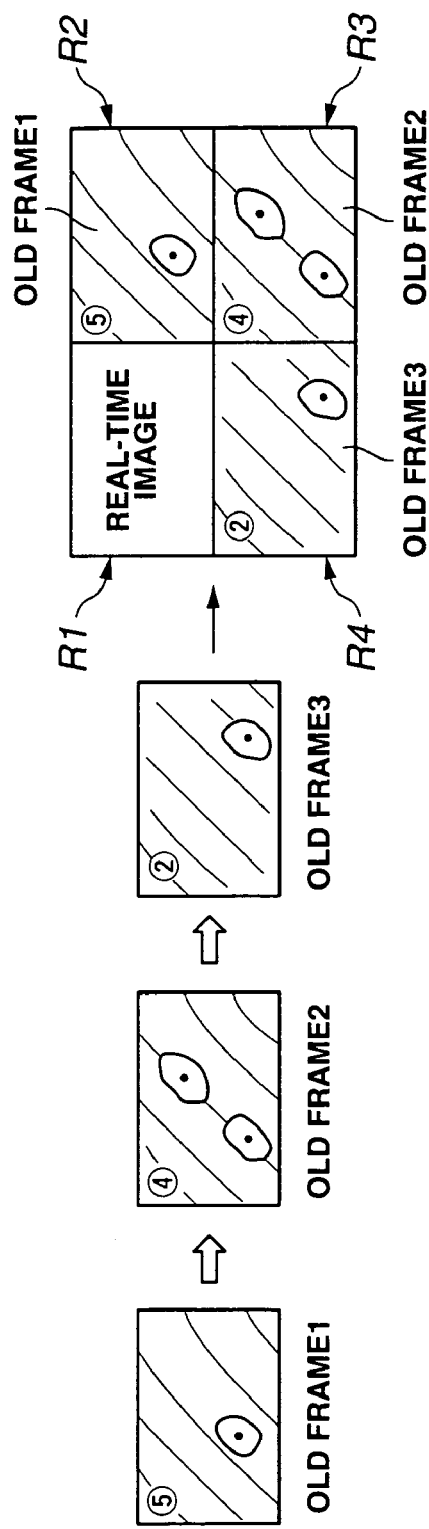
FIG.9A
FIG.9B

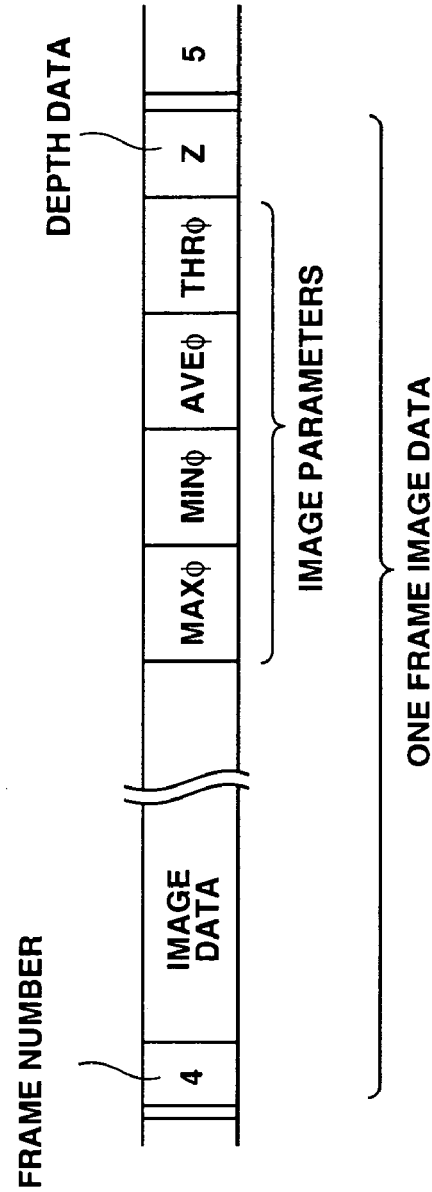

FRAME IMAGE 1
FRAME IMAGE 2
FRAME IMAGE 3
FRAME IMAGE 4
SYNTHETIC IMAGE

FIG.36A

PATTERNS OF SETTINGS FOR DISPLAY/PRESERVATION

| DISPLAY/PRESERVATION MODE | REFERENCE FOR SELECTION | | | TIMING | BLUR CORRECTION | SIMULTANEOUSLY PRESERVED DATA | NUMBER OF SELECTIVE PATTERNS |
|---|---|---|---|---|---|---|---|
| SPECIFIC-IMAGE DISPLAY/PRESERVATION | LUMINANCE VALUE | DESIGNATION OF SIZE=ON | | START OF SCANNING | ON/OFF | NORMAL ENDOSCOPIC IMAGE SCALE TEXT CURSOR | 5 |
| | | | | EXECUTION OF FREEZE | ON/OFF | | |
| | | | | BEFORE OR AFTER EXECUTION OF FREEZE | ON/OFF | | |
| | | | | START OF LASER LIGHT EMISSION | ON/OFF | | |
| | | | | START OF BLUR CORRECTION | ON | | |
| | | DESIGNATION OF SIZE=OFF | | START OF SCANNING | ON/OFF | NORMAL ENDOSCOPIC IMAGE SCALE TEXT CURSOR | 5 |
| | | | | EXECUTION OF FREEZE | ON/OFF | | |
| | | | | BEFORE OR AFTER EXECUTION OF FREEZE | ON/OFF | | |
| | | | | START OF LASER LIGHT EMISSION | ON/OFF | | |
| | | | | START OF BLUR CORRECTION | ON | | |
| | AREA | | | START OF SCANNING | ON/OFF | NORMAL ENDOSCOPIC IMAGE SCALE TEXT CURSOR | 5 |
| | | | | EXECUTION OF FREEZE | ON/OFF | | |
| | | | | BEFORE OR AFTER EXECUTION OF FREEZE | ON/OFF | | |
| | | | | START OF LASER LIGHT EMISSION | ON/OFF | | |
| | | | | START OF BLUR CORRECTION | ON | | |
| | Frame Image | | | START OF SCANNING | ON/OFF | NORMAL ENDOSCOPIC IMAGE SCALE TEXT CURSOR | 5 |
| | | | | EXECUTION OF FREEZE | ON/OFF | | |
| | | | | BEFORE OR AFTER EXECUTION OF FREEZE | ON/OFF | | |
| | | | | START OF LASER LIGHT EMISSION | ON/OFF | | |
| | | | | START OF BLUR CORRECTION | ON | | |
| | TIME | | | START OF SCANNING | ON/OFF | NORMAL ENDOSCOPIC IMAGE SCALE TEXT CURSOR | 5 |
| | | | | EXECUTION OF FREEZE | ON/OFF | | |
| | | | | BEFORE OR AFTER EXECUTION OF FREEZE | ON/OFF | | |
| | | | | START OF LASER LIGHT EMISSION | ON/OFF | | |
| | | | | START OF BLUR CORRECTION | ON | | |
| SPECIFIC-IMAGE DISPLAY/ ALL-IMAGES PRESERVATION | LUMINANCE VALUE | DESIGNATION OF SIZE=ON | | START OF SCANNING | ON/OFF | NORMAL ENDOSCOPIC IMAGE SCALE TEXT CURSOR | 5 |
| | | | | EXECUTION OF FREEZE | ON/OFF | | |
| | | | | BEFORE OR AFTER EXECUTION OF FREEZE | ON/OFF | | |
| | | | | START OF LASER LIGHT EMISSION | ON/OFF | | |
| | | | | START OF BLUR CORRECTION | ON | | |
| | | DESIGNATION OF SIZE=OFF | | START OF SCANNING | ON/OFF | NORMAL ENDOSCOPIC IMAGE SCALE TEXT CURSOR | 5 |
| | | | | EXECUTION OF FREEZE | ON/OFF | | |
| | | | | BEFORE OR AFTER EXECUTION OF FREEZE | ON/OFF | | |
| | | | | START OF LASER LIGHT EMISSION | ON/OFF | | |
| | | | | START OF BLUR CORRECTION | ON | | |
| | AREA | | | START OF SCANNING | ON/OFF | NORMAL ENDOSCOPIC IMAGE SCALE TEXT CURSOR | 5 |
| | | | | EXECUTION OF FREEZE | ON/OFF | | |
| | | | | BEFORE OR AFTER EXECUTION OF FREEZE | ON/OFF | | |
| | | | | START OF LASER LIGHT EMISSION | ON/OFF | | |
| | | | | START OF BLUR CORRECTION | ON | | |

FIG. 36B

| | | | | | |
|---|---|---|---|---|---|
| SPECIFIC-IMAGE DISPLAY/ ALL-IMAGES PRESERVATION | Frame Image | | START OF SCANNING | ON/OFF | NORMAL ENDOSCOPIC IMAGE SCALE TEXT CURSOR | 5 |
| | TIME | | EXECUTION OF FREEZE | ON/OFF | | |
| | | | BEFORE OR AFTER EXECUTION OF FREEZE | ON/OFF | | |
| | | | START OF LASER LIGHT EMISSION | ON/OFF | | |
| | | | START OF BLUR CORRECTION | ON | | |
| ALL-IMAGES DISPLAY/ SPECIFIC-IMAGE PRESERVATION | LUMINANCE VALUE | DESIGNATION OF SIZE=ON | START OF SCANNING | ON/OFF | NORMAL ENDOSCOPIC IMAGE SCALE TEXT CURSOR | 5 |
| | | | EXECUTION OF FREEZE | ON/OFF | | |
| | | | BEFORE OR AFTER EXECUTION OF FREEZE | ON/OFF | | |
| | | | START OF LASER LIGHT EMISSION | ON/OFF | | |
| | | | START OF BLUR CORRECTION | ON | | |
| | | DESIGNATION OF SIZE=OFF | START OF SCANNING | ON/OFF | NORMAL ENDOSCOPIC IMAGE SCALE TEXT CURSOR | 5 |
| | | | EXECUTION OF FREEZE | ON/OFF | | |
| | | | BEFORE OR AFTER EXECUTION OF FREEZE | ON/OFF | | |
| | | | START OF LASER LIGHT EMISSION | ON/OFF | | |
| | | | START OF BLUR CORRECTION | ON | | |
| | AREA | | START OF SCANNING | ON/OFF | NORMAL ENDOSCOPIC IMAGE SCALE TEXT CURSOR | 5 |
| | | | EXECUTION OF FREEZE | ON/OFF | | |
| | | | BEFORE OR AFTER EXECUTION OF FREEZE | ON/OFF | | |
| | | | START OF LASER LIGHT EMISSION | ON/OFF | | |
| | | | START OF BLUR CORRECTION | ON | | |
| | Frame Image | | START OF SCANNING | ON/OFF | NORMAL ENDOSCOPIC IMAGE SCALE TEXT CURSOR | 5 |
| | | | EXECUTION OF FREEZE | ON/OFF | | |
| | | | BEFORE OR AFTER EXECUTION OF FREEZE | ON/OFF | | |
| | | | START OF LASER LIGHT EMISSION | ON/OFF | | |
| | | | START OF BLUR CORRECTION | ON | | |
| | TIME | | START OF SCANNING | ON/OFF | NORMAL ENDOSCOPIC IMAGE SCALE TEXT CURSOR | 5 |
| | | | EXECUTION OF FREEZE | ON/OFF | | |
| | | | BEFORE OR AFTER EXECUTION OF FREEZE | ON/OFF | | |
| | | | START OF LASER LIGHT EMISSION | ON/OFF | | |
| | | | START OF BLUR CORRECTION | ON | | |
| ALL-IMAGES DISPLAY/PRESERVATION | DESIGNATION DISABLED | | START OF SCANNING | ON/OFF | NORMAL ENDOSCOPIC IMAGE SCALE TEXT CURSOR | 5 |
| | | | EXECUTION OF FREEZE | ON/OFF | | |
| | | | BEFORE OR AFTER EXECUTION OF FREEZE | ON/OFF | | |
| | | | START OF LASER LIGHT EMISSION | ON/OFF | | |
| | | | START OF BLUR CORRECTION | ON | | |
| TOTAL | | | | | | 80 |

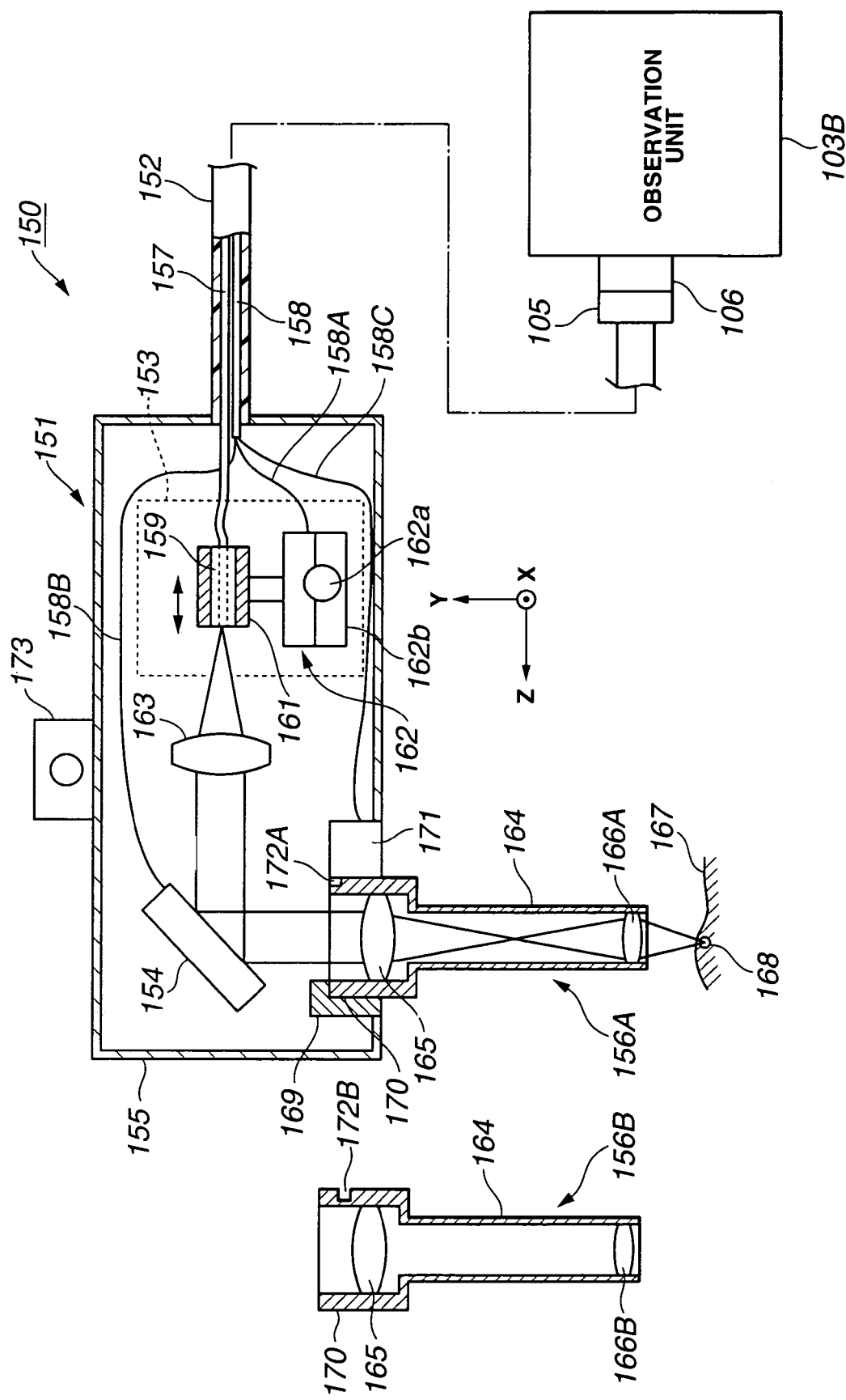

OPTICAL PROBE SYSTEM

This application claims the benefit of Japanese Applications No. 2002-279905 filed on Sep. 25, 2002, No. 2002-290410 filed on Oct. 2, 2002, and No. 2003-317380 filed on Sep. 9, 2003, the contents of which are incorporated by this reference.

BACKGROUND OF THE INVENTION

1. Field of the Invention

The present invention relates to an optical probe system that uses an optical probe to produce an image of an optically scanned intracavitary region.

2. Description of the Related Art

In recent years, for example, Japanese Unexamined Patent Application Publication No. 2000-126115 discloses a related art adapted to an optical probe system that uses an optical scanning probe to observe a living tissue in enlargement.

According to the related art, light is scanned even in a depth direction so that an image in the depth direction can be produced.

SUMMARY OF THE INVENTION

Accordingly, an optical probe system in accordance with the present invention comprises an optical probe that is inserted into a body cavity, a light source that generates light which is irradiated to an object, and a high-magnification observation unit included in the distal section of the optical probe.

The optical probe system further comprises:

an image digitization unit that digitizes a luminance signal produced by the high-magnification observation unit;

an image parameter sampling unit that samples an image parameter from an image;

an optimization parameter calculation unit that calculates an optimization parameter on the basis of the image parameter;

an image optimization unit that optimizes an image according to the optimization parameter;

an image display device on which an optimized image is displayed; and a digital image preservation unit in which a digital image is preserved.

BRIEF DESCRIPTION OF THE DRAWINGS

FIG. 1 to FIG. 12 are concerned with a first embodiment of the present invention;

FIG. 1 shows the overall configuration of an optical scanning probe system in accordance with the first embodiment;

FIG. 2 shows the configuration of the distal section of an optical scanning probe shown in FIG. 1;

FIG. 3 is a block diagram showing the components of a personal computer and an image parameter sampling means shown in FIG. 1;

FIG. 4 shows an endoscope through which the optical scanning probe is passed;

FIG. 5 is a sectional view showing the structure of the distal section of a confocal optical scanning probe;

FIG. 6 schematically shows the structure of an optical unit shown in FIG. 5;

FIG. 8 shows examples of produced time-sequential image frames;

FIG. 9A and FIG. 9B are explanatory diagrams concerning sampling of images, which are actually displayed on a multi-image display means, from the time-sequential frame images shown in FIG. 8, and displaying of the images;

FIG. 10 is a flowchart describing displaying of images in areas R2 to R4 on the multi-image display means;

FIG. 12 is a flowchart describing displaying of images in the areas R2 to R4 on the multi-image display means according to a variant;

FIG. 14A to FIG. 17 are concerned with a third embodiment of the present invention;

FIG. 14A and FIG. 14B show a histogram expressing an image whose contrast is not converted and a histogram expressing an image whose contrast is converted according to the third embodiment;

FIG. 15 is a flowchart describing histogram conversion from the histogram shown in FIG. 14A to the one shown in FIG. 14B;

FIG. 16 is a flowchart describing operations to be performed according to a first variant;

FIG. 17 is a flowchart describing operations to be performed according to a second variant;

FIG. 18 to FIG. 20 are concerned with a fourth embodiment of the present invention;

FIG. 18 schematically shows images produced by scanning an object in a depth direction using a condenser lens employed in the fourth embodiment;

FIG. 19 shows an example of time-sequential images produced by scanning an object in a depth direction in the case of FIG. 18;

FIG. 20 shows the image data and image parameters preserved in the digital image preserving means;

FIG. 21 schematically shows an image produced when a shake occurs in a horizontal direction in the fifth embodiment;

FIG. 22 shows an example of four images produced in the case of FIG. 21;

FIG. 23 shows an image produced by pasting the four images shown in FIG. 22;

FIG. 24 and FIG. 25 are concerned with a sixth embodiment of the present invention;

FIG. 24 shows the structure of an optical scanning means employed in the sixth embodiment;

FIG. 27 to FIG. 49 are concerned with an eighth embodiment of the present invention;

FIG. 27 shows the overall configuration of an optical scanning observation unit employed in the eighth embodiment;

FIG. 28 shows an example of display on a monitor;

FIG. 29 is an explanatory diagram concerning a method of defining an area in a case where an area is selected as a reference for display;

FIG. 30 is a flowchart describing the entire process from designation of a display/preservation method to execution of display/preservation;

FIG. 31 is a flowchart describing designation of a display/preservation mode;

FIG. 32 is a flowchart describing designation of a reference for selection;

FIG. 33 is a flowchart describing designation of an area;

FIG. 34 is a flowchart describing designation of timing;

FIG. 35 is a flowchart describing designation of simultaneously preserved data;

FIG. 36A and FIG. 36B list patterns in which display and preservation of a specific image can be selected or designated by determining various parameters;

FIG. 37 is a flowchart describing display/preservation to be performed in a case where a display/preservation mode is set to a specific-image display/preservation mode, a reference for selection is set to a luminance value (=150), designation of a size is disabled (off), timing is set to the start of scanning, blur correction is disabled (off), and simultaneously preserved data is set to a normal endoscopic image and a scale;

FIG. 38 is a block diagram showing the circuit elements of a signal processing circuit included when a reference for selection is set to a luminance value;

FIG. 39 is a timing chart indicating the timing of starting or stopping display and preservation when timing is set to the start of scanning;

FIG. 40 is a flowchart describing a process to be executed when the designation of a size that is one of the parameters described in FIG. 37 is enabled (on);

FIG. 41 is a flowchart describing a process to be executed in case where a display/preservation mode is set to a specific-image display/all-images preservation mode, a reference for selection is set to an area, timing is set to the execution of freeze (the time of displaying a still image), blur correction is disabled (off), and simultaneously preserved data is set to a text;

FIG. 42 is a timing chart concerning the process described in FIG. 41;

FIG. 43 is a flowchart describing a process to be executed in a case where a display/preservation mode is set to an all-images display/specific-image preservation mode, a reference for selection is set to a frame image, the number of specific frame images is 50 ranging from frame image 1 to frame image 50, timing is set to the timing preceding or succeeding freeze (a timing position is set to −10), blur correction is disabled (off), and simultaneously preserved data is set to a cursor;

FIG. 44 is a timing chart indicating the start of display and preservation that precedes or succeeds freeze as designated in the case described in FIG. 43;

FIG. 45 is an explanatory diagram showing data to be preserved when the timing is set to the timing preceding or succeeding freeze;

FIG. 46 is a flowchart describing a process to be executed in a case where a display/preservation mode is set to a specific-image display/preservation mode, a reference for selection is set to a time, a specified time is set to 1000 msec, and timing is set to the start of laser light emission, blur correction is disabled (off), and simultaneously preserved data is set to a normal endoscopic image;

FIG. 47 is a timing chart indicating the start/stop of display and preservation to be performed in the case described in FIG. 46;

FIG. 48 is a flowchart describing a process to be executed in a case where a display/preservation mode is set to an all-images display/preservation mode, timing is set to the start of blur correction, and blur correction is enabled (on), and simultaneously preserved data is set to a scale;

FIG. 49 is a timing chart indicating the start/stop of display or preservation to be performed in the case described in FIG. 48;

FIG. 50 and FIG. 51 are concerned with a ninth embodiment 2 of the present invention;

FIG. 50 shows the configuration of an optical probe system in accordance with the ninth embodiment; and FIG. 51 shows an example of use of an optical probe shown in FIG. 50.

DETAILED DESCRIPTION OF THE PREFERRED EMBODIMENTS

Figure 1:
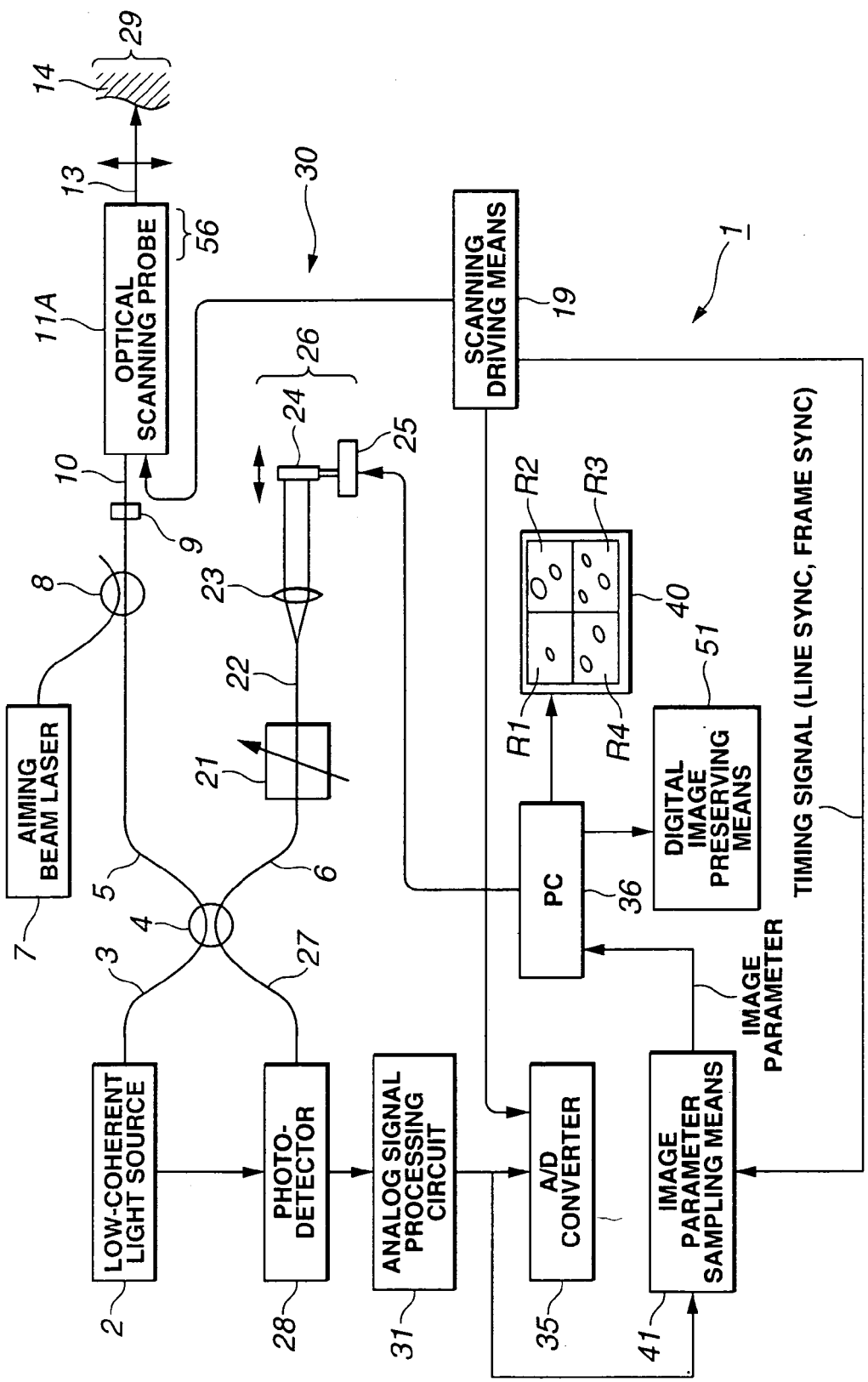

Referring to the drawings, embodiments of the present invention will be described below.

First Embodiment

Referring to FIG. 1 to FIG. 12, a first embodiment of the present invention will be described below.

In an optical scanning probe system (more broadly, an optical probe system or optical imaging system) 1 of the first embodiment shown in FIG. 1, low-coherent near infrared light emanating from a low-coherent light source 2 is propagated over a first optical fiber 3, and branched into a third optical fiber 5 and a fourth optical fiber 6 by an optical coupler 4 that has four input and output terminals.

Visible laser light emanating from an aiming beam laser 7 is introduced into the third optical fiber 5 by an optical coupler 8. The third optical fiber 5 is joined to a fifth optical fiber 10 via an optical connector 9, and propagates low-coherent light to an optical scanning probe 11A.

Figure 2:
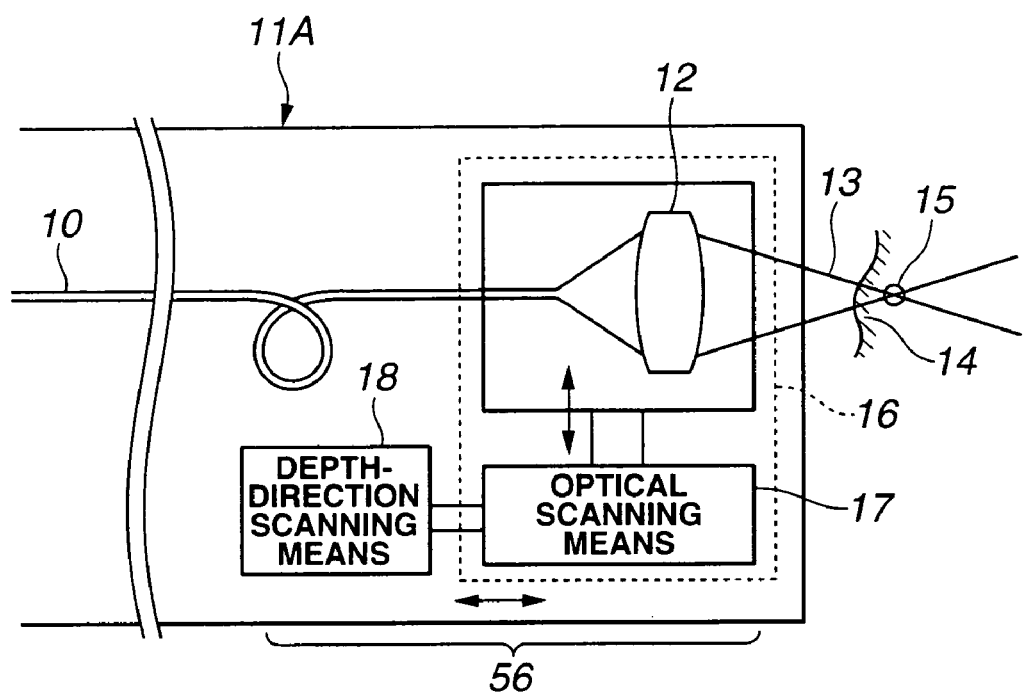

FIG. 2 shows the configuration of the distal section 56 of the optical scanning probe 11A. Low-coherent light emitted from the end of the fifth optical fiber 10 is converged as viewing light (viewing beam) 13 at a viewing point 15 within an object of observation 14 by means of a condenser lens (objective lens) 12 that converges light. An objective unit 16 comprising the end of the fifth optical fiber 10 and the condenser lens 12 includes an optical scanning means 17, and scans the object of observation 14 that is an object while moving the viewing light 13 and viewing point 15 in two-dimensional directions.

Moreover, the objective unit 16 is connected to a depth-direction scanning means 18 serving as a focus moving means, and can therefore scan the viewing point 15 in the depth direction. The optical scanning means 17 and depth-direction scanning means 18 are driven by a scanning driving means 19 shown in FIG. 1. That is, the focus moving means moves the condenser lens 12 and optical scanning means 17 as one united body in optical-axis directions.

The optical scanning probe 11A is a thin soft tubular body and can therefore be readily inserted into a body cavity directly or trans-endoscopically and trans-vascularly. Moreover, the optical scanning probe 11A may be constructed as an endoscope having an observation optical system.

The fourth optical fiber 6 is coupled to a frequency shifter 21. An output of the frequency shifter 21 is routed to a sixth optical fiber 22. A phase modifying means formed with an acoustooptic device (AOM), an electrooptic device (EO), or a piezoelectric element with a fiber loop can be adopted as the frequency shifter 21.

Light emitted from the end of the sixth optical fiber 22 is introduced into a movable mirror 24 via a collimator lens 23. The movable mirror 24 is moved in the directions of the ray axis of emission light by means of a mirror driving means 25. The end of the sixth optical fiber 22, collimator lens 23, movable mirror 24, and mirror driving means 25 constitute an optical path length adjusting means 26.

A second optical fiber 27 coupled to the remaining terminal of the optical coupler 4 is coupled to a photo detector 28. Preferably, a single-mode optical fiber, a low-order multi-mode optical fiber capable of fully sustaining coherence, or a polarization-preserving optical fiber may be adopted as the first optical fiber 3, second optical fiber 27, third optical fiber 5, fourth optical fiber 6, fifth optical fiber 10, and sixth optical fiber 22.

Near-infrared low-coherent light emanating from the low-coherent light source 2 is introduced to the first optical fiber 3, and branched into the third optical fiber 5 and fourth optical fiber 6 by the optical coupler 4. Light introduced into the third optical fiber 5 is introduced into the optical scanning probe 11A via the optical connector 9 over the fifth optical fiber 10, and emitted as the viewing light 13 to the object of observation 14.

The optical scanning means 17 and depth-direction scanning means 18 sweep the viewing light 13 and viewing point 15 so as to scan the object of observation 14. Light reflecting or scattering from the viewing point 15 in the object of observation 14 returns to the fifth optical fiber 10 via the condenser lens 12, and goes back to the third optical fiber 5 by following the foregoing path inversely. This light path shall be called an object-side path 29.

Similarly, low-coherent light branched into the fourth optical fiber 6 has the frequency thereof shifted by the frequency shifter 21, and is then emitted to the collimator lens 23 over the sixth optical fiber 22. The light incident on the collimator lens 23 is recomposed into substantially parallel rays, and introduced into the movable mirror 24. The light reflected from the movable mirror 24 is introduced into the sixth optical fiber 22 by the collimator lens 23, and thus returns to the fourth optical fiber 6. This light path shall be called a reference path 30.

The light waves traveling along the object-side path 29 and reference path 30 respectively are mixed by the optical coupler 4. Assume that the optical path length of the object-side path 29 and that of the reference path 30 agree with each other within the range of the coherence length of light emanating from the low-coherence light source 2. In this case, the photo detector 28 detects an interference wave whose frequency change is equal to or twice greater than a frequency shift produced by the frequency shifter 21 through the second optical fiber 27.

Herein, the mirror driving means 25 included in the optical path length adjusting means 26 is used to adjust the position in an optical-axis direction of the movable mirror 24 so that the optical path length of the reference path 30 will agree with the optical path length of the object-side path extending to the viewing point 15. Consequently, information fetched from the viewing point 15 is acquired as an interference wave all the time.

The photo detector 28 converts the detected interference wave into an electric signal. The electric signal is transferred to an analog signal processing circuit 31. As shown in FIG. 3, the analog signal processing circuit 31 comprises an amplifier 32, a filter 33, and a logarithmic amplifier 34. The amplifier 32 amplifies the signal, the filter 33 samples a signal component having a predetermined frequency, and the logarithmic amplifier 34 produces a logarithmic function of the signal. Thereafter, the resultant signal is transferred to an A/D converter 35, and analog-to-digital converted.

In this case, the scanning driving means 19 moves the viewing point 15 of the viewing light 13 two-dimensionally, that is, substantially vertically and in the depth direction. Synchronously with a scanning control signal, the A/D converter 35 analog-to-digital converts the received signal. The resultant signal is fetched into a personal computer (PC) 36.

As shown in FIG. 3, signal data of, for example, 8 bits long transferred from the A/D converter 35 to the PC 36 is stored in a frame memory 37 synchronously with a timing signal produced by the scanning driving means 19. The timing signals are a sync signal LINE SYNC used to scan an object in one direction and a sync signal FRAME SYNC synchronous with a frame. The signal data is stored synchronously with these sync signals.

The signal data stored in the frame memory 37 is read and transferred to a logarithmic/linear transformation circuit, that is, an inverse transformation circuit 38 whose transformation is the inverse of the transformation performed by the logarithmic amplifier 34. Consequently, the signal data is changed to signal data of, for example, 10 bits long having a linear characteristic. The signal data has the contrast value thereof transformed by a contrast converting means 39. Thereafter, the data is transmitted from the PC 36 into a multi-image display means 40 comprising a monitor and an image recording means. Eventually, multiple images are displayed.

Moreover, an output signal of the analog signal processing circuit 31 is transferred to an image parameter sampling means 41. In this case, as shown in FIG. 3, the output signal has the noise thereof canceled by a noise canceling means 42. The signal having the noise thereof canceled is transferred to each of a maximum value detection circuit 43, a minimum value detection circuit 44, an average value detection circuit 45, and a differential circuit 46 that samples data representing an edge. The maximum value detection circuit 43, minimum value detection circuit 44, average value detection circuit 45, and differential circuit 46 samples respective image parameters, that is, a maximum luminance value, a minimum luminance value, an average luminance value, and data representing an edge respectively. In this case, the signal to be transferred has the components thereof, which represent frame images, integrated (summated). A maximum value or the like is sampled (detected) from each signal component representing one frame image. Incidentally, the noise canceling means is realized with a filter that cancels a noise.

The output signals of the maximum value detection circuit 43, minimum value detection circuit 44, and average value detection circuit 45 are converted into a maximum value MAXφ, a minimum value MINφ, and an average value AVEφ respectively, which are digital quantities, by A/D converters 47, 48, and 49 respectively. Thereafter, the image parameters are transferred to a digital image preserving means 51.

Moreover, among the maximum value MAXφ, the minimum value MINφ, the average value AVEφ, and a threshold value THRφ which are sampled by the image parameter sampling means 41, a specific image parameter calculated as an image parameter needed to optimize an image to be displayed is transmitted to the contrast converting means 39 that optimizes an image, and thus used to convert a contrast.

To be more specific, the image parameters, for example, the maximum value MAXφ and minimum value MINφ are transferred to the contrast converting means 39 serving as an image optimizing means within the PC 36. The image parameters are used to change a contrast for the purpose of optimizing an image to be displayed as described later in conjunction with FIG. 7. Incidentally, a plurality of concrete examples of the contrast converting means 39 also utilizes the image parameter of the average value AVEφ.

Moreover, the output signal of the differential circuit 46 that samples data representing an edge is converted into a signal THRφ, which is checked to see if the signal level is equal to or larger than a threshold value, by a threshold value circuit 50. Thereafter, the signal is transferred to each of a digital image preserving means 51 and the multi-image display means 40.

Figure 4:
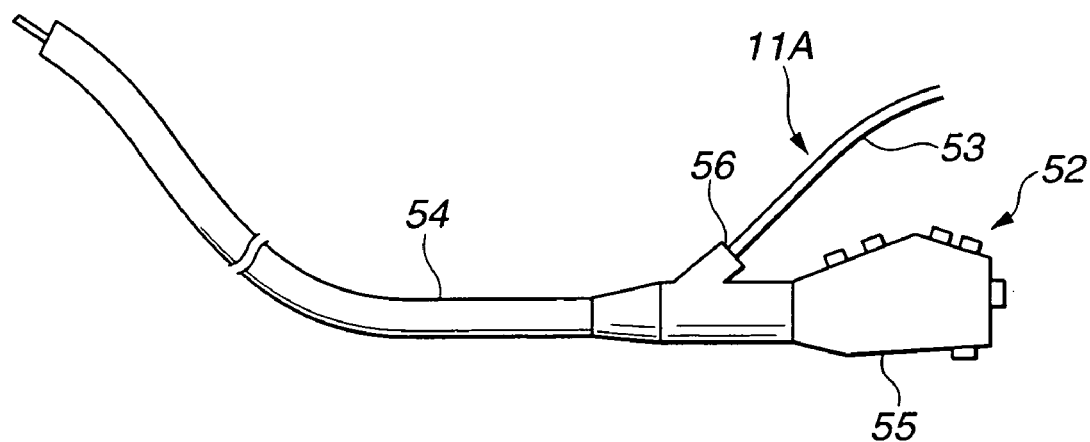

Moreover, the optical scanning probe 11A is, as shown in FIG. 4, passed through an endoscope 52 for use.

As shown in FIG. 4, the optical scanning probe 11A can be sheathed with a sheath 53 that is elongated and flexible, and can be inserted into a channel lying through an endoscope 52. The endoscope 52 has an elongated insertion unit 54, and an operating unit 55 formed at the rear end of the insertion unit 54. A treatment instrument insertion port 56 that communicates with a channel lying through the insertion unit 54 is bored near the front end of the operating unit 55. The optical scanning probe 11A can be inserted through the treatment instrument insertion port 56.

Assuming that an operator wants to check under observation through the endoscope 52 if a tissue is a lesion, the distal end of the optical scanning probe 11A is projected from the distal end of the channel, and approached to the surface of the tissue concerned. Thus, an image is acquired using the optical scanning probe 11A.

The aforesaid optical fiber 10 is passed through the sheath 53. As shown in FIG. 2, the optical scanning means 17 moves the condenser lens 12 two-dimensionally in directions orthogonal to the optical axis of the condenser lens. This results in a two-dimensional image. Moreover, the depth-direction scanning means 18 moves the objective unit 16, whereby a two-dimensional image results from scanning in the optical-axis direction, that is, the depth direction. The system having been described so far is a system that produces a microscopic image (high-magnification image) using the low-coherence optical scanning probe 11A that employs low-coherent light. Alternatively, a system may employ a confocal optical scanning probe that forms a microscopic image using confocal optical elements as disclosed in, for example, Japanese Unexamined Patent Application Publication No. 2000-126115.

In the system employing the confocal optical scanning probe, a laser light source or the like is adopted on behalf of the low-coherent light source 2 shown in FIG. 1. Moreover, the end of the optical fiber 6 is clogged or the like for fear return light may be generated. The end of the optical fiber 27 is coupled to the photo detector 28.

Moreover, the photo detector 28 and the components in the succeeding stages are the same as those described previously. The description will therefore be omitted. The structure of the distal section of a confocal optical scanning probe 11B employed in the present embodiment will be described in conjunction with FIG. 5.

Figure 5:
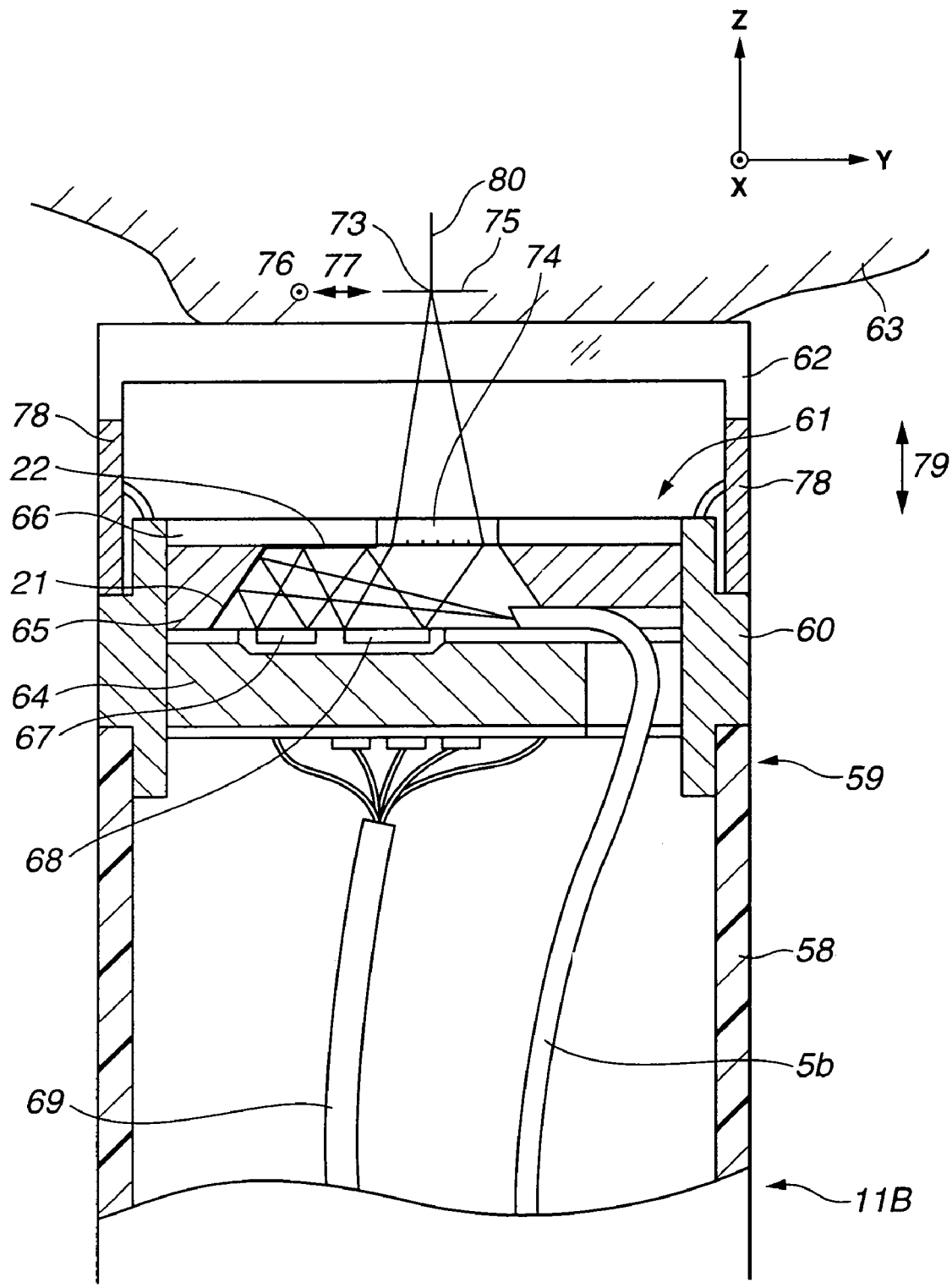

As shown in FIG. 5, the distal section 59 of the confocal optical scanning probe 11B comprises: a hard optical frame 60 having one end thereof fixed to the distal end of a tube 58 and being shaped annularly; an optical unit 61 locked in the optical frame 60; and a (transparent and hard) distal cover 62 that is coupled to the distal end of the optical frame 60 with a piezoelectric element 78, which will be described later, between them, that is pressed against an object, and that serves as a transparent window member.

The distal end of an optical fiber 5b that is inserted into the tube 58 and coupled to the light source and to the photo detector 28 via the optical coupler 4 is fixed to the optical unit 61. Light emitted from the distal end of the optical fiber 5b is converged at and irradiated to an object 63, which is an object of examination, using an optical scanning mechanism (scanner). The return light is received.

Figure 6:
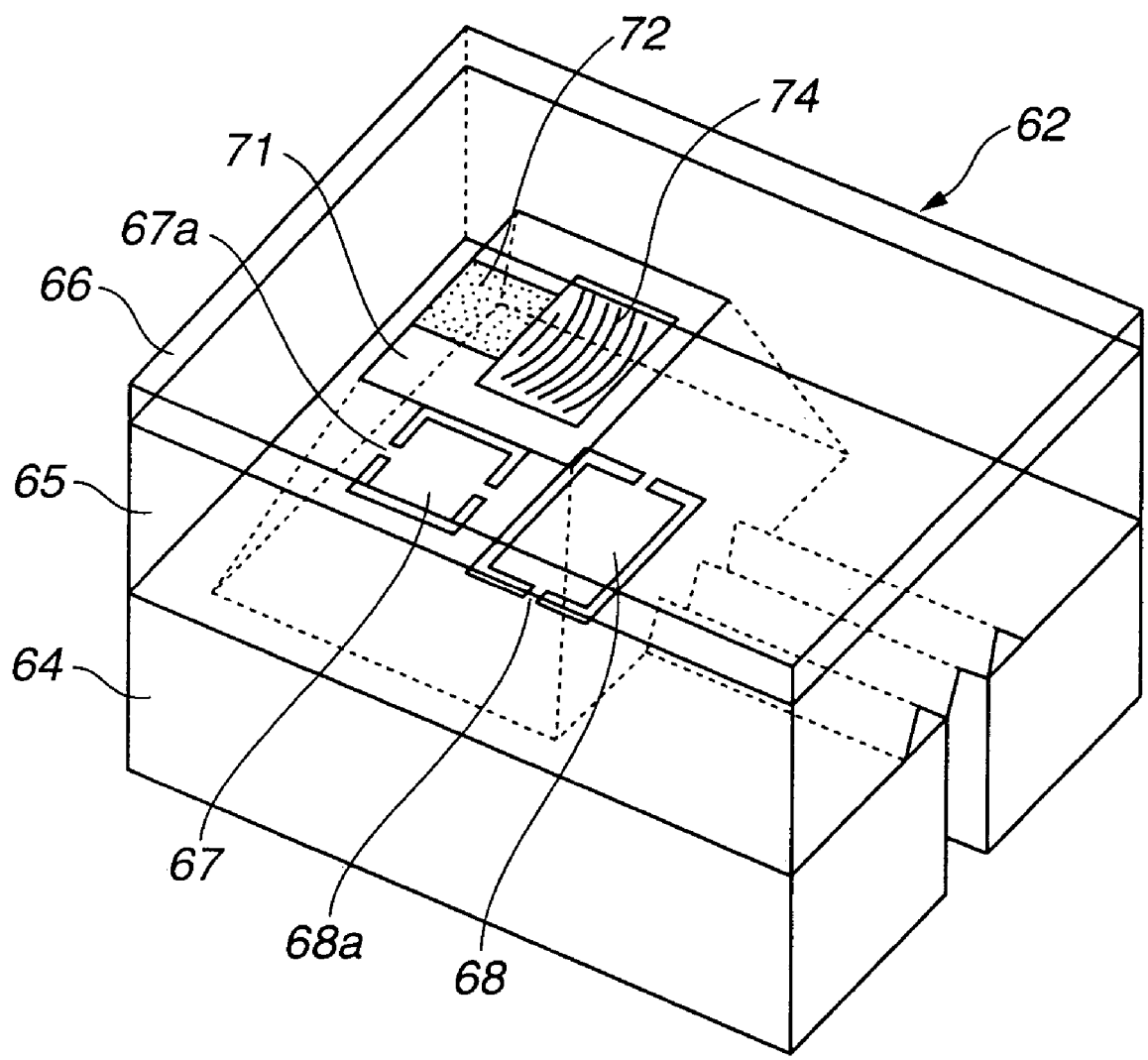

FIG. 6 shows the structure of the optical unit 61 in detail.

The optical unit 61 comprises a substrate 64, a spacer 65 placed on the top of the substrate 64, and a top plate 66 placed on the top of the spacer 65. Two movable mirrors (or rotary mirrors) 67 and 68 whose directions are variable are mounted on the substrate 64 so that laser light emitted from the light source and propagated over the optical fiber 5b will sweep an object.

The two movable mirrors 67 and 68 are supported on two hinges 67a and 68a respectively. The movable mirrors 67 and 68 are designed to be turnable with electrostatic force induced by electrodes that are not shown.

Grounds (not shown) opposed to the electrodes are connected to the optical scanning driving means 19 over a cable 69. The axes of rotation of the two movable mirrors 67 and 68 are designed in a direction orthogonal each other. Furthermore, a mirror 71 is mounted on a surface of the spacer 65 opposed to the end of the optical fiber 5b. A mirror 72 and a diffraction grating lens 74 that converges laser light and focuses it at a focal point 73 on the object 63 are mounted on the top plate 66.

The diffraction grating lens 74 brings about diffraction and exhibits the capability equivalent to the capability of a lens characteristic of a very short focal length. The focal point 73 is two-dimensionally scanned in a depth direction of the object 69 and a direction orthogonal to the depth direction, whereby an image of the object 63 enlarged as if it were enlarged with a microscope can be produced.

Moreover, the distal part of the optical fiber 5b is, as shown in FIG. 5, locked between the substrate 64 and spacer 65.

A driving signal is applied to the (electrodes of the) movable mirrors 67 and 68, whereby the movable mirrors 67 and 68 are driven to turn an appropriate angle with the hinges 67a and 68a as the axes of rotation. Consequently, the focal point 73 can be two-dimensionally scanned on a scanning plane 75.

For example, when the movable mirror 67 is driven, light is swept in X directions 76 that are vertical directions with respect to the sheet of paper of FIG. 5. When the movable mirror 68 is driven, light is swept in Y directions 77 that are lateral directions in FIG. 5. That is to say, when the movable mirror 67 or 68 is moved, the focal point 73 on the object 63 can be two-dimensionally scanned on the scanning plane 75 perpendicular to the depth direction (Z direction). Thus, a confocal microscope is realized in order to acquire information of light reflected from the scanning plane 75.

In other words, the area of the distal end of the optical fiber 5b is very small. The movable mirrors 67 and 68 and diffraction grating lens 74 are arranged to have a confocal relationship or a near confocal relationship and to share the focal point 73. Consequently, light emitted from the microscopically small distal end of the optical fiber 5b falls on the focal point 73 in the form of a microscopic light spot. Light reflected from the light spot (and its vicinity) falls on the distal end of the optical fiber 5b.

One end of the piezoelectric element 78, which is a small-size plate-like or bar-like, is bonded to four portions of the optical frame 60 that circumferentially cross at right angles. The other end of the piezoelectric element 78 is bonded to the proximal edge of the distal cover 62. Moreover, the piezoelectric element 78 is connected to the optical scanning driving means 19 over the cable 69.

When a driving signal is applied to the piezoelectric element 75, the piezoelectric element 78 stretches or contracts as indicated with reference numeral 79 in FIG. 5 in the Z direction that corresponds to the depth direction of the object 63. Thus, the focal point 73 is varied in the Z direction on a cutting plane 80. Incidentally, the distal cover 62 is formed with a transparent cover made of, for example, polycarbonate.

As mentioned above, the present embodiment can be adapted to either the system employing the optical scanning probe 11A that utilizes low-coherent light or the system employing the optical scanning probe 11B that utilizes the confocal optical elements. Next, the operation of the present embodiment will be described.

The optical scanning probe 11A or 11B shown in FIG. 1 or FIG. 5 is used to produce a high-magnification image through optical scanning. In this case, a signal resulting from photoelectric conversion performed by the photo detector 28 is transformed into a logarithmic function thereof by the logarithmic amplifier 34 included in the analog signal processing circuit 31. Thus, the dynamic range of the signal is temporarily compressed. Thereafter, the output signal of the logarithmic amplifier is digitized by the A/D converter 35, and time-sequentially stored in the frame memory 37 included in the PC 36.

The signal data (image data) time-sequentially stored in the frame memory 37 is transformed to exhibit a linear characteristic by means of the logarithmic/linear transformation circuit 38. Thus, the dynamic range for the signal is stretched (expanded). This results in image data of, for example, 10 bits long.

The image data is transferred to the contrast converting means 39 that optimizes an image to be displayed, converted into an image exhibiting an appropriate contrast, and displayed on the multi-image display means 40.

Figure 7A:
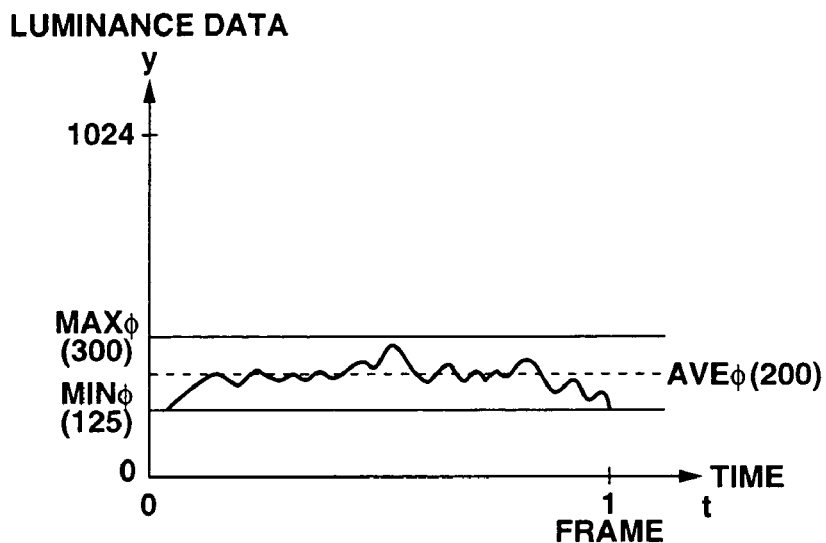
FIG. 7A and FIG. 7B graphically show time-sequential luminance data that is transferred to a contrast converting means, and graphically show changed luminance data together with a contrast changing expression.
Figure 7B:
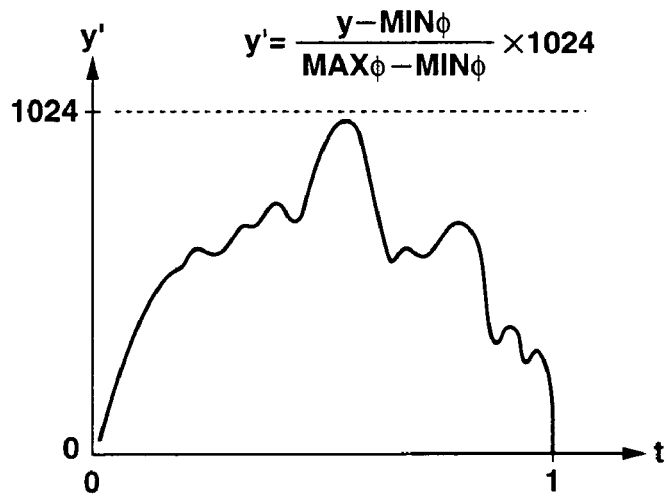

FIG. 7A and FIG. 7B are explanatory diagrams concerning the above process. FIG. 7A graphically shows time-sequential luminance data that is transferred to the contrast converting means 39. The luminance data is converted into the one shown in FIG. 7B by means of the contrast converting means 39 in order to provide an appropriate contrast.

In this case, the time-sequential luminance data y of one frame image is converted by means of the contrast converting means 39 according to an expression (1) that employs a maximum value MAXφ and a minimum value MINφ sampled from one frame image in order to provide an appropriate contrast. This conversion results in luminance data y'.

$$y'=(y-\text{MIN}\phi)/(\text{MAX}\phi-\text{MIN}\phi)\times 1024 \tag{1}$$

Consequently, even when the contrast of an image is low, that is, the difference between the maximum and minimum values of an image is small, an image having an appropriate contrast is displayed owing to the contrast change.

Figure 7C:
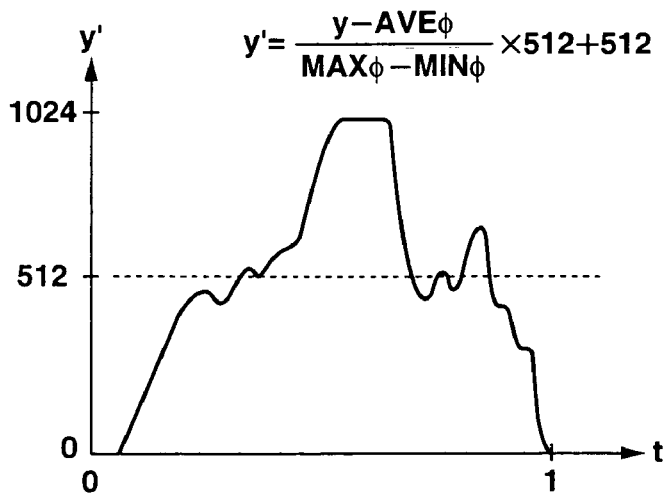
FIG. 7C graphically shows changed luminance data together with a contrast changing expression different from the expression shown in FIG. 7B.

The luminance data graphically shown in FIG. 7A may be converted into the one shown in FIG. 7C by means of the contrast converting means 39 in order to provide an appropriate contrast. In the case of FIG. 7C, the average value AVEφ is substituted for the minimum value MINφ included in the numerator of the expression (1). Namely, a contrast is converted according to an expression (2) below in order to provide luminance data y'.

$$y'=(y-\text{AVE}\phi)/(\text{MAX}\phi-\text{MIN}\phi)\times 512+512 \tag{2}$$

Consequently, when a contrast is too low or an image is too bright, an image can be displayed with an appropriate contrast through the contrast conversion.

As mentioned above, the present embodiment performs contrast conversion. For example, even a too dark image is displayed at a luminance level (brightness level) that is easy for a user to see, and is therefore seen as an easy-to-view image. Even a too bright image has the brightness level thereof converted into an easy-to-view level and is therefore seen as an easy-to-view image.

The system may be designed so that a user can designate the characteristic of the system for contrast conversion. Namely, a user uses a selection switch or the like to designate the characteristic of, for example, the contrast converting means 39 for contrast conversion according to an object of observation. Depending on the selection, for example, the expression (1) or expression (2) may be designated.

In the above case where a contrast is changed as shown in FIG. 7C, for example, an abrupt change of the contrast of a frame image from the contrast of a preceding frame image may be suppressed as described below.

That is to say, an average value AVE(t) of a frame image t may be adopted as the average value AVEφ employed in the expression (2), and a range RANGE(t) in the frame image t may be substituted for the difference between the maximum and minimum values, that is, MAXφ−MINφ in the denominator of the expression (2). (Herein, t denotes each frame image. For example, an average value AVE(t) means an average value of luminance data contained in the data of a frame image t).

$$\begin{aligned}&\text{AVE}(t)=\text{AVE}(t-1)+\text{MAXdiff if AVEdiff}\geq\text{MAXdiff or}\\&\text{AVE}(t)=\text{AVE}(t-1)+\text{AVEdiff or }-\text{MAXdiff if}\\&\text{AVEdiff}\leq\text{MAXdiff}\end{aligned} \tag{3}$$

where $$\text{AVEdiff}=\text{AVE}\phi-\text{AVE}(t-1) \tag{4}$$

$$\begin{aligned}&\text{RANGE}(t)=\text{RANGE}(t-1)+\text{MAXdiff2 if RANGEdiff}\\&\text{MAXdiff2 or RANGE}(t)=\text{RANGE}(t-1)+\text{RANG-}\\&\text{Ediff or MAXdiff2 if RANGEdiff}\leq-\text{MAXdiff2}\end{aligned} \tag{5}$$

where $$\text{RANGE}\phi=\text{MAX}\phi-\text{MIN}\phi \tag{6}$$

$$\text{RANGEdiff}=\text{RANGE}\phi-\text{RANGE}(t-1) \tag{7}$$

According to the expression (2), when frame images are sequentially displayed in real time, the frame images are displayed with optimized appropriate contrasts. However, if a scanning speed is high or a shake is made, the contrast of a frame image changes significantly from that of a previous one. In this case, contrast conversion is (partly) disabled in order to disable optimization of the contrast of each frame image. Thus, the images may be displayed as a motion picture in which an abrupt change of the contrast of a frame image from the contrast of a preceding one is suppressed.

In this case, when the above expressions (3) to (7) are employed, an abrupt change of the contrast of a frame image from the contrast of a preceding one can be suppressed, and images can be displayed with appropriate contrasts.

Instead of modifying the expression (2) according to the expressions (3) to (7), parameters k1 to m3 may be used to define the average AVE(t) and range RANGE(t) as presented below. Thus, contrast conversion may be performed in order to optimize a contrast.

$$AVE(t)=k1AVE(t-1)+k2AVE(t-2)+k3AVE(t-3) \qquad (8)$$

$$RANGE(t)=m1RANGE(t-1)+m2RANGE(t-2)+ \\ m3RANGE(t-3) \qquad (9)$$

In this case, an average of luminance values of a past frame image or a contrast of the frame image is partly taken into account by reflecting it in the parameter, and contrast conversion is performed. Consequently, appropriate contrast images can be displayed with an abrupt change of the contrast of a frame image from the contrast of a preceding one suppressed.

Image data whose contrast data is converted is transmitted to each of the multi-image display means 40 and the digital image preserving means 51. As shown in FIG. 1 and FIG. 9B, real-time images (motion picture) are displayed in a real-time image display area R1 on the multi-image display means 40. As described later, old images that meet a threshold value condition are displayed in other image display areas R2, R3, and R4.

Moreover, in the digital image preserving means 51, digital images that meet a predetermined threshold value condition determined by the threshold value circuit 50 included in the image parameter sampling means 41 are recorded together with image parameters.

FIG. 8 shows a concrete example of (real-time) images produced time-sequentially. Namely, frame image 1 (1̂ in FIG. 8. The same applies to other frame numbers.) is an image produced when the contour or edge of a tissue of an object of observation cannot be detected. For example, an average value AVEφ that is one of image parameters is 0 and a threshold value THRφ is 0.

Frame image 2 is an image produced when the edge of the tissue of the object of observation can be recognized considerably well. For example, the average value AVEφ that is one of image parameters is 50, and the threshold value THRφ is 1. The average of the image is equal to or larger than the threshold value determined by the threshold value circuit 50.

As mentioned above, an image depicting an edge (contour) whose average is equal to or larger than the threshold value determined by the threshold value circuit 50 is preserved in the digital image preserving means 51. Moreover, the result of judgment made by the threshold value circuit 50 is transferred to the multi-image display means 40. Old images each depicting an edge whose averages are equal to or larger than threshold values determined by the threshold value circuit are displayed in the image display areas R2 to R4.

FIG. 9B shows old frame images 1 to 3 displayed in the image display areas R2 to R4 on the multi-image display means 40. In this case, the multi-image display means 40 includes three frame memories as an image storage means in which frame images to be displayed in the image display areas R2 to R4 are stored. Frame images are, as shown in FIG. 9A, stored in the three frame memories orderly from the oldest one.

In the case of time-sequential images shown in FIG. 8, the oldest frame image 1, the second oldest frame image 2, and the third oldest frame image 3 are stored in the three frame memories, and displayed in the fashion shown in FIG. 9B. When the threshold value circuit 50 detects an old image to be preserved next, the image is displayed in the image display area R4 as the newest frame image among the old frame images, that is, as an old frame image 3. In this case, the old frame image 4 shown in FIG. 9A is displayed as the oldest frame image in the image display area R2, and the frame image 2 is displayed as the second oldest frame image in the image display area R3.

Figure 10:
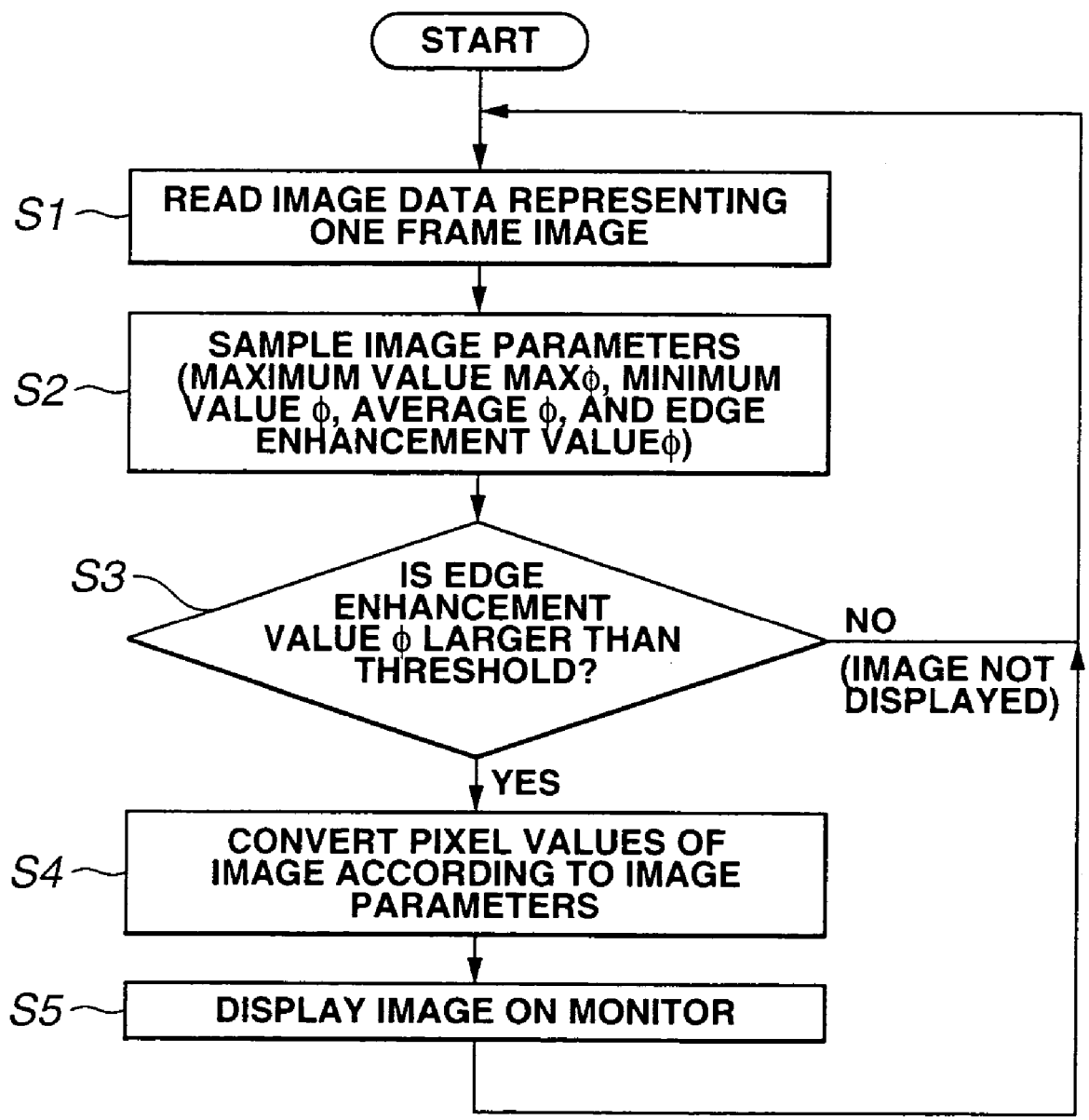

FIG. 10 is a flowchart describing operations to be performed for displaying frame images in the image display areas R2 to R4 according to the present embodiment.

The image parameter sampling means 41 reads the image data of one frame image at step S1. At step S2, image parameters (a maximum value MAXφ, a minimum value MINφ, an average value AVEφ, and an edge enhancement value EDGφ) are sampled.

The image parameter sampling means 41 judges at step S3 whether the edge enhancement value EDGφ exceeds the threshold value determined by the threshold value circuit 50 shown in FIG. 3. If the edge enhancement value EDGφ does not exceed the threshold value, control is returned to step S1. The next image data is then acquired. That is to say, in this case, acquired image data is not displayed.

On the other hand, if the edge enhancement value EDGφ exceeds the threshold value, the PC 36 selects an image parameter, which is needed to optimize image display, from the above image parameters sampled by the image parameter sampling means 41 at step S4. The PC 36 uses the image parameter to convert the values of pixels constituting an image. In particular, the contrast conversion expression (1) or (2) is adopted.

At step S5, an image whose pixel values are converted in order to convert the contrast of the image is displayed on the monitor screen of the multi-image display means 40. Thereafter, control is returned to step S1, and the next frame image is processed similarly.

Frame images detected relative to threshold values of predetermined levels determined by the threshold value circuit 50 are sequentially stored in the digital image preserving means 51. Namely, images to be displayed in the image display areas R2 to R4 on the multi-image display means 40 are preserved.

Figure 11A:
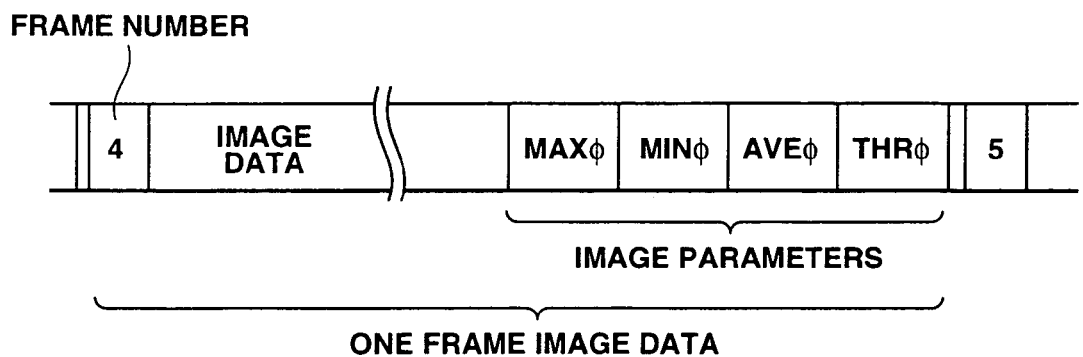
FIG. 11A and FIG. 11B show a file structure in which image data representing one frame image and image parameters are preserved in a digital image preserving means, and a file structure in which a plurality of frame images is preserved.
Figure 11B:

FIG. 11 shows a file structure in which data is preserved in the digital image preserving means 51. FIG. 11A shows a file structure in which one frame image is preserved. FIG. 11B shows a file structure in which a plurality of frame images is recorded.

For example, when frame image 4 is preserved in the digital image preserving means 51, as shown in FIG. 11A, the frame number, image data, and the image parameters such as a maximum value MAXφ of the image data, a minimum value MINφ thereof, an average value AVEφ thereof, and a threshold value THRφ are preserved.

Since the image parameters are preserved together with the image data, a raw image can be regenerated (reproduced). Moreover, a preserved image can be quantitatively assessed. The use value of the image data is thus increased.

As mentioned above, according to the present embodiment, the parameter sampling means 41 samples the predetermined image parameters such as the maximum value MAXφ, minimum value MINφ, average value AVEφ, and threshold value THRφ from received image data. Among the sampled image parameters, the image parameters needed for optimization, that is, the maximum value MAXϕ and minimum value MINϕ are transferred to the contrast converting means 39 included in the PC 36. Contrast data contained in received image data is converted in order to optimize the contrast, whereby an optimal image is produced. The image is displayed in the real-time image display area R1 on the multi-image display means 40. Even when an observation image produced at a high magnification has an inappropriate contrast or an image contains a noise, the image can be displayed at an appropriate contrast.

Moreover, an image that depicts an edge (contour) of a tissue of an object of observation at an edge enhancement level equal to or higher than a predetermined level is displayed in any of the other image areas R2 to R4 on the multi-image display means 40. Thus, an image that depicts an edge of a tissue or the like at an edge enhancement level equal to or higher than the predetermined level can be displayed. Namely, only an image depicting a contour of a tissue or the like of an object of observation at an edge enhancement level equal to or higher than the predetermined level can be displayed. In other words, an image not depicting a contour at an edge enhancement level equal to or higher than the predetermined level is not displayed.

Therefore, even if the optical scanning probe 11A or 11B is shook during use, only an image that depicts a tissue of an object of observation (depicts the contour of the tissue some extent) is sampled and displayed. An image not depicting the contour is not displayed.

According to the present embodiment, the logarithmic amplifier 34 included in the analog signal processing circuit 31 provides a logarithmic function of an input signal. Thereafter, the logarithmic/linear transformation circuit 38 in the PC 36 inversely transforms the output signal of the logarithmic amplifier. Consequently, even an image represented by a signal enjoying a large dynamic range can be displayed with the large dynamic range left intact. An image can therefore be displayed with a gray scale or a tone close to a natural one, and preserved therewith.

Moreover, digital images to be displayed in the other image areas R2 to R4 on the multi-image display means 40 are preserved in the digital image preserving means 51. Only images depicting an edge of a tissue or the like at an edge enhancement level equal to or higher than a predetermined level are preserved efficiently.

In other words, images not depicting an edge of a tissue or the like of an object of observation at an edge enhancement level equal to or higher than the predetermined level are not preserved. Unnecessary images are therefore not preserved. Consequently, the labor of editing is lightened and the necessity of editing is obviated.

Figure 12:
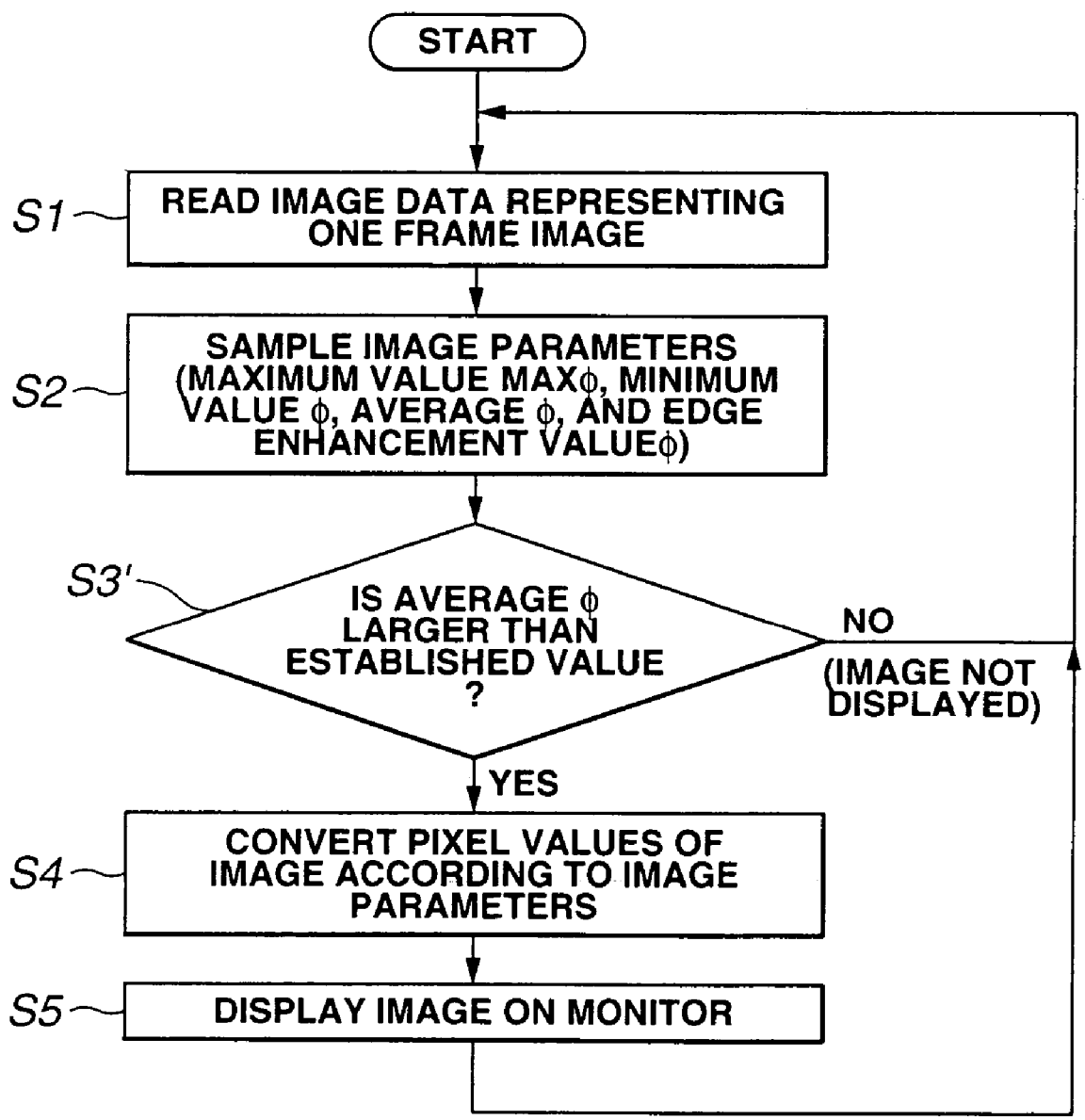

FIG. 12 is a flowchart describing operations to be performed for optimizing images and displaying the images in the image display areas R2 to R4 according to a variant. The operations are identical to those described in FIG. 10 except that step S3 is changed to step S3'.

At step S1, image data representing one frame image is read. At step S2, image parameters (a maximum value MAXϕ, a minimum value MINϕ, an average value AVEϕ, and an edge enhancement level EDGϕ) are sampled from the image data.

The image parameter sampling means 41 judges at step S3' whether the average value AVEϕ exceeds a predetermined value. In this case, the average value detection circuit 45 included in the image parameter sampling means 41 has the capability to sample the average value AVEϕ and judge whether the average value AVEϕ exceeds the predetermined value. Alternatively, the PC 36 makes the judgment.

If the average value AVEϕ does not exceed the predetermined value, control is returned to step S1 and the next image data is acquired. In this case, the acquired image data is not displayed.

On the other hand, if the average value AVEϕ exceeds the predetermined value, the PC 36 selects an image parameter needed to optimize image display among all the image parameters, and uses the image parameter to convert the values of pixels constituting an image. Specifically, the PC 36 converts the pixel values to optimize the contrast of the image according to the expression (1) or (2).

The PC 36 transmits the image, of which contrast is converted, to the multi-image display means 40 at step S5. After the image is displayed on the monitor screen of the multi-image display means 40, control is returned to step S1. The next image data is processed in the same manner. The present variant provides substantially the same advantage as the first embodiment.

In this case, the dynamic range is compressed using a logarithmic amplifier. Alternatively, gamma conversion may be performed in order to compress the dynamic range.

Moreover, in the digital image preserving means 51, a digital image whose contrast is converted is preserved together with image parameters thereof. Alternatively, an image whose contrast has not yet been converted may be preserved together with the image parameters.

Moreover, the differential circuit 46 shown in FIG. 3 may be replaced with a high-pass filter that samples a high-frequency component of an image signal. For example, a received signal may be passed through the high-pass filter, and the output signal components of the high-pass filter may be integrated during one frame. The resultant signal may be transferred to the threshold value circuit 50, and has the signal components thereof compared with a predetermined threshold value level determined by the threshold value circuit 50. The threshold value THRϕ based on the result of the comparison may be transmitted.

When the threshold value determined by the threshold value circuit 50 is increased, an image depicting a larger contour or an in-focus image can be detected.

Moreover, the cutoff characteristic of the high-pass filter may be selected from some cutoff characteristics.

In order to, for example, preserve a nearly in-focus image, a high-pass filer whose cutoff frequency is set to a high frequency is selected. The signal components passing through the high-pass filter are integrated, and the threshold value circuit 50 compares the resultant sum of the signal levels with a predetermined level. Thus, an image represented by an image signal whose integral level is equal to or larger than the predetermined level may be preserved.

Moreover, when an image is preserved, the result of comparison (judgment) made by the threshold value circuit 50 may also be preserved.

Second Embodiment

Next, a second embodiment of the present invention will be described below. According to the first embodiment, the contrast converting means 39 serving as an image optimizing means is realized mainly with software that is run in the PC 36. The present embodiment uses hardware to convert a contrast.

Figure 13:
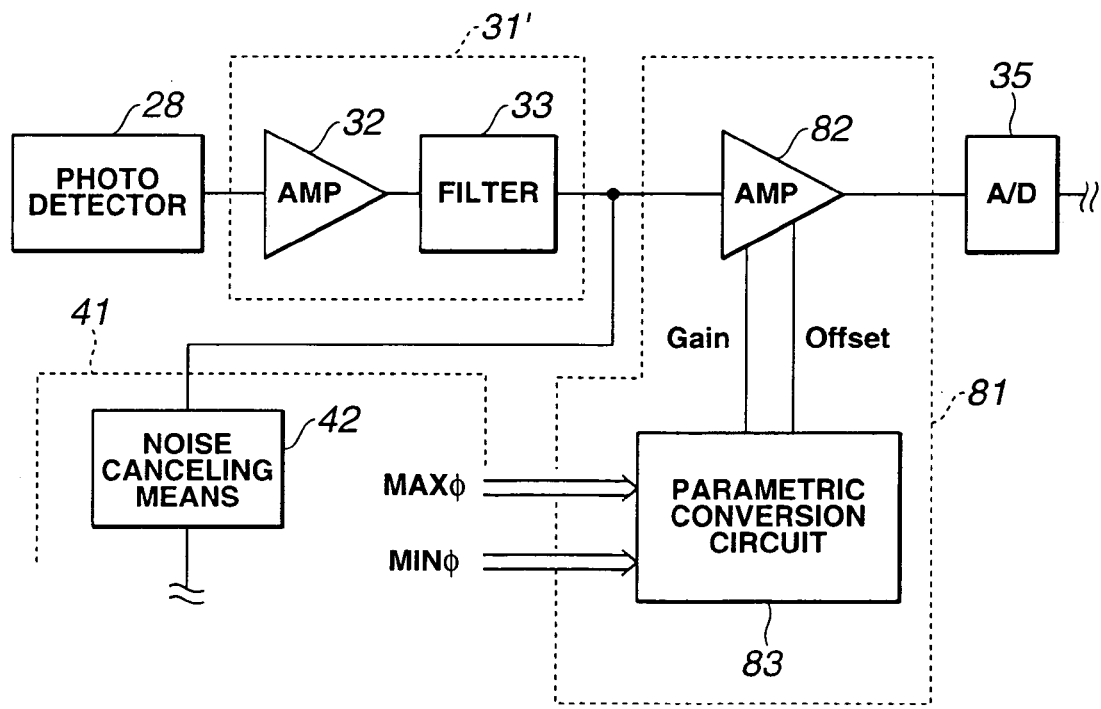
FIG. 13 is a block diagram showing the circuit elements of a contrast converting means and its peripherals employed in a second embodiment of the present invention.

FIG. 13 shows the configuration of a contrast converting means 81 and its peripherals employed in the second embodiment. The second embodiment does not have the contrast converting means 39 incorporated in the PC 36 shown in FIG. 3. Moreover, the analog signal processing circuit 31 shown in FIG. 3 is replaced with an analog signal processing circuit 31' comprising an amplifier 32 and a filter 33.

According to the present embodiment, an output signal of the filter 33 is transferred to an amplifier 82 included in the contrast converting means 81. A gain to be produced by the amplifier 82 and an offset needed thereby are controlled with an output signal sent from the parametric conversion circuit 83. A contrast represented by a signal sent from the amplifier 82 is converted so that an image exhibiting an appropriate contrast can be produced.

An output signal of the amplifier 82 is transferred to the A/D converter 35.

The image parameter sampling means 41 shown in FIG. 3 transfers image parameters, for example, a maximum value MAX$\phi$ and a minimum value MIN$\phi$ to the parametric conversion circuit 83. The parametric conversion circuit 83 performs parametric conversion so as to produce a signal, which is used to control the gain to be produced by the amplifier 82 and the offset needed thereby, according to the image parameters, and thus controls the amplifier 82.

Owing to the control, according to the present embodiment, contrast conversion based on the aforesaid expression (1) is performed in real time. The resultant signal is transmitted to the A/D converter 35. The stage succeeding the A/D converter 35 is identical to the one included in the circuitry which is shown in FIG. 3 and from which the contrast converting means 39 is excluded.

The present embodiment provides nearly the same operation and advantage as those of the first embodiment.

Third Embodiment

Figure 14A:
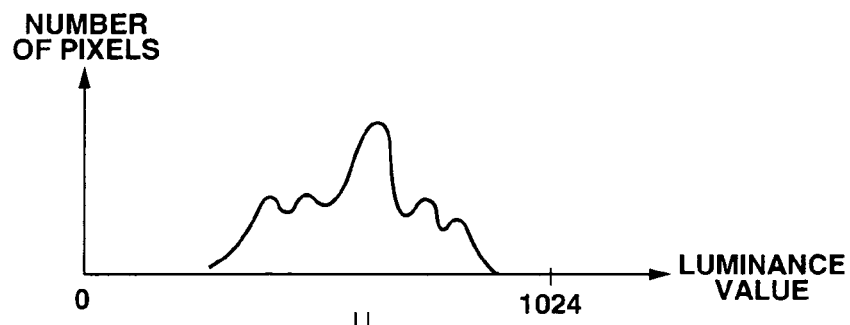

Next, a third embodiment of the present invention will be described below. According to the present embodiment, when an input image whose property is expressed with a histogram shown in FIG. 14A, the property of the image is converted to the one expressed with a histogram shown in FIG. 14B using software that is run in the PC 36 shown in FIG. 3 (CPU that is incorporated in the PC 36 and not shown). The resultant image is then displayed on the monitor 4.

Operations to be performed in this case will be described with reference to FIG. 15 below.

At step S11, the PC 36 reads image data representing one frame image. At step S12, the (CPU incorporated in the) PC 36 produces an image parameter whose values are plotted as a histogram, that is, data plotted in FIG. 14A.

The (CPU incorporated in the) PC 36 produces a conversion table listing pixel values so as to even out the histogram at step S13.

Figure 14B:
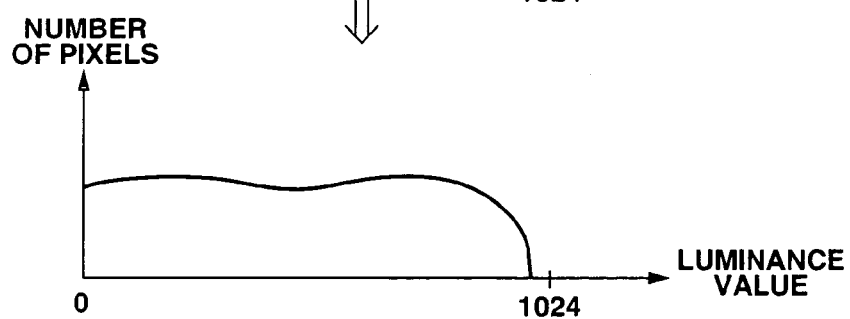

The (CPU incorporated in the) PC 36 converts the values of pixels constituting an image on the basis of the conversion table at step S14, and thus converts the image into an image expressed with the histogram shown in FIG. 14B. The PC 36 then transmits the image resulting from the conversion to the multi-image display means 40 at step S15. The resultant image is displayed on the monitor screen of the multi-image display means 40. Control is then returned to step S11, and the next image data is processed in the same manner.

The present embodiment provides nearly the same operation and advantage as those of the first embodiment.

Figure 16:
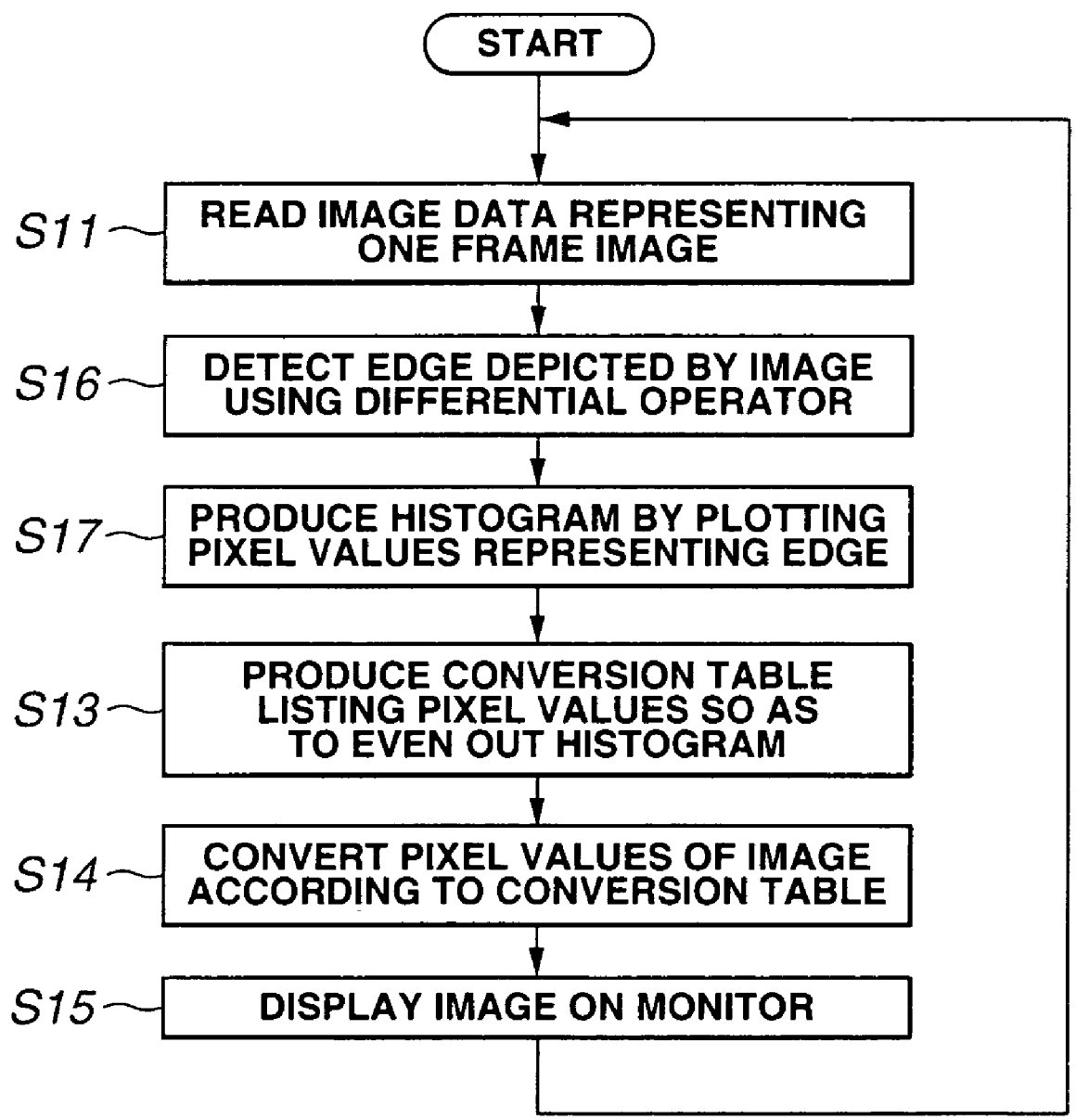

According to a first variant of the present embodiment, a process described in FIG. 16 may be executed.

Figure 15:
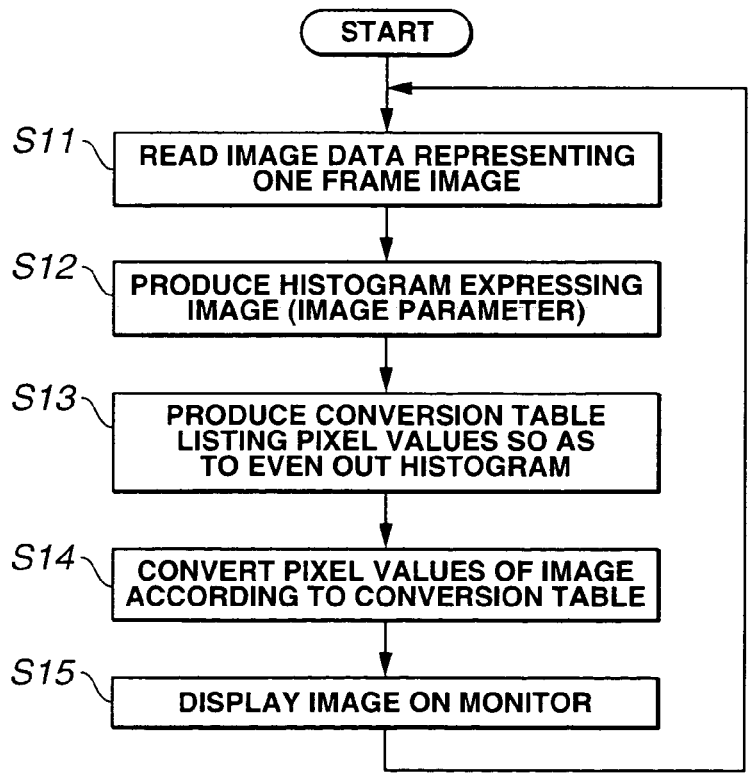

The process described in FIG. 16 is identical to the one described in FIG. 15 except that step S16 and step S17 are performed on behalf of step S12.

At step S11, the PC 36 reads image data representing one frame image. At step S16, the (CPU incorporated in the) PC 36 uses a differential operator to detect an edge depicted by an image.

At step S17, the (CPU incorporated in the) PC 36 produces a histogram using the values of pixels representing the edge. Thereafter, steps S13, S14, and S15 are carried out.

According to the present variant, a portion of an image depicting an edge of an object can be optimized and displayed.

Figure 17:
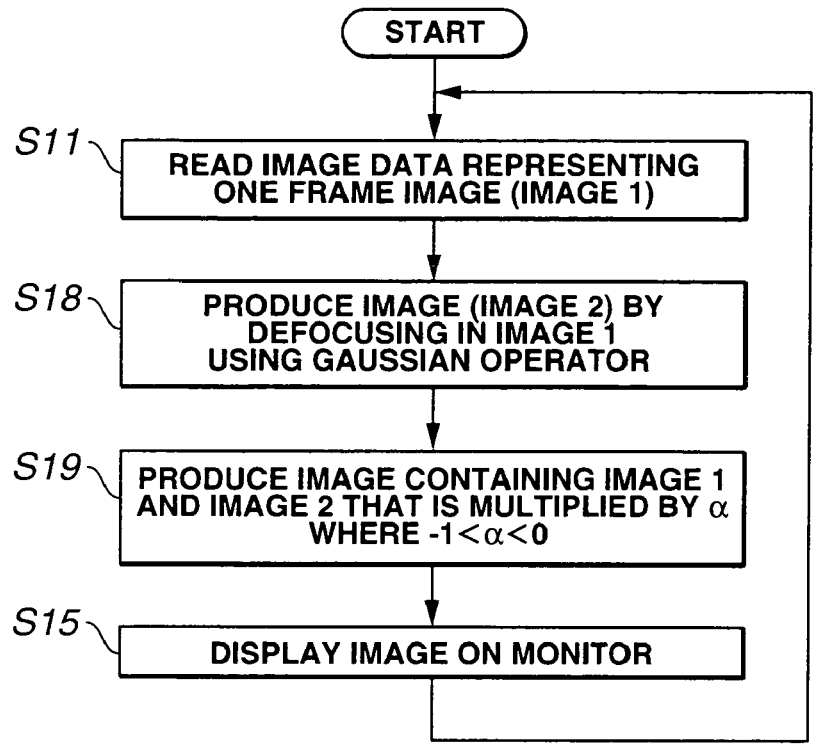

A process described in FIG. 17 and employed in a second variant may be executed. At step S11, the PC 36 reads image data (representing frame image 1). At step S18, the (CPU incorporated in the) PC 36 uses a Gaussian operator, which designates a Gaussian function, to produce an image (image 2) by shading in image 1 that is a raw image.

At the next step S19, the (CPU incorporated in the) PC 36 produces an image containing the image 1 and the image 2 enlarged to be $\alpha$ times larger. Herein, the parameter $\alpha$ ranges from −1 to 0. At step S15, the produced image is displayed on the monitor screen of the multi-image display means 40.

The present invention is not limited to a mode in which the process described in FIG. 10 or FIG. 12 is implemented in an algorithm to be followed by the CPU incorporated in the PC 36. Alternatively, the process may be implemented in software to be run in a digital signal processor or implemented in hardware.

The first to third embodiments have been described on the assumption that the condenser lens (objective lens) 12 shown in FIG. 2 or the diffraction grating lens 74 shown in FIG. 5 is not moved along the optical-axis direction corresponding to the depth direction of an object of observation (Z direction). A fourth embodiment to be described below will prove effective in a case where the condenser lens 12 is moved in the direction corresponding to the depth direction.

Fourth Embodiment

Next, a fourth embodiment of the present invention will be described below. The present embodiment will be described by taking the system including the condenser lens 12 for instance.

Figure 18:
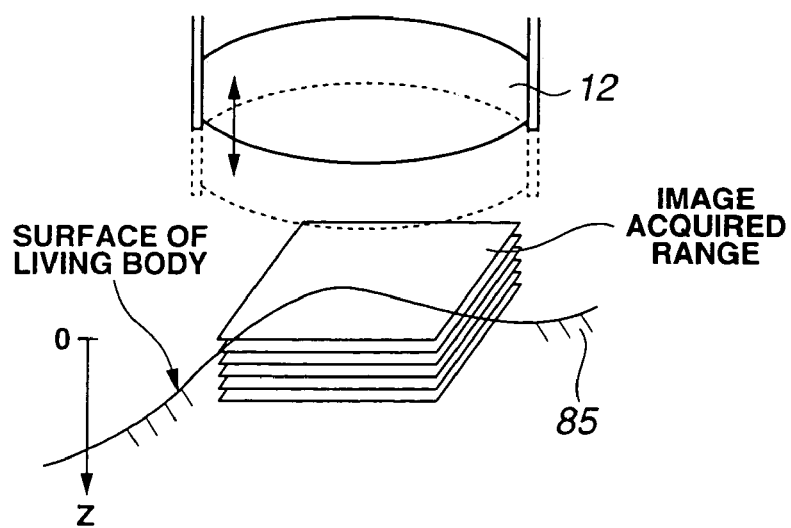

According to the present embodiment, as shown in FIG. 18, the condenser lens 12 is moved in the same direction as the depth direction of a living body 85 that is an object of observation in order to scan the living body. Images of two-dimensional scanned ranges (image-acquired ranges) are acquired at a plurality of positions that are scanned.

Assuming that a depth coordinate representing the depth of a scanning start point at which scanning in the depth direction is started is 0, time-sequential images shown in FIG. 19 are acquired.

For example, the average value AVE$\phi$ of frame image 1, that is, an image acquired at a depth represented by a depth coordinate Z of 0, and the threshold value THR$\phi$ therefor are 0s. The average value AVE$\phi$ of frame image 2, that is, an image acquired at a depth represented by a depth coordinate Z of 20 ($\mu$m), and the threshold value THR$\phi$ therefor are 0s. The average value AVE$\phi$ of frame image 3, that is, an image acquired at a depth represented by a depth coordinate Z of 40 ($\mu$m), and the threshold value THR$\phi$ therefor are 50 and 1 respectively.

When two-dimensional images are acquired by scanning a living body in the depth direction, for example, frame images 1 and 2 do not depict the contour of a tissue of an object of observation at all. However, when scanning in the depth direction proceeds, frame images 4 and 5 clearly depicting the contour of the tissue of the object of observation, that is, in-focus or nearly in-focus frame images can be acquired.

As mentioned above, the present embodiment provides the same advantage as, for example, the first embodiment. In addition, the present embodiment scans an object in the depth direction and detects information in the depth direction.

When image data is preserved in the digital image preserving means 51, the value of the depth coordinate Z is preserved as depth data together with the image data and image parameters.

In other words, according to the present embodiment, data representing one frame image is preserved in a file structure shown in FIG. 20. The data representing one frame image is identical to the one shown in FIG. 11A except that the depth data is appended.

Incidentally, image optimization or the like can be achieved by adopting the means or method described in relation to the first to third embodiments.

According to the present embodiment, an object is scanned in the depth direction. If a scanned range contains a point whose distance from an object of observation permits the object of observation to come into focus, an image depicting the object that is in focus or nearly in focus, that is, an image depicting the contour of the object (at an edge enhancement level higher than a predefined level) can be acquired nearly reliably.

Incidentally, two-dimensional images acquired at different depths may be synthesized in order to construct a three-dimensional image. Moreover, an object may be scanned in the depth direction and in one of X and Y directions orthogonal to the depth direction in order to display or preserve a two-dimensional tomographic image.

Fifth Embodiment

Next, a fifth embodiment of the present invention will be described below. The present embodiment will be described on the assumption that an optical scanning system includes the objective unit 16 having the condenser lens 12.

Figure 21:
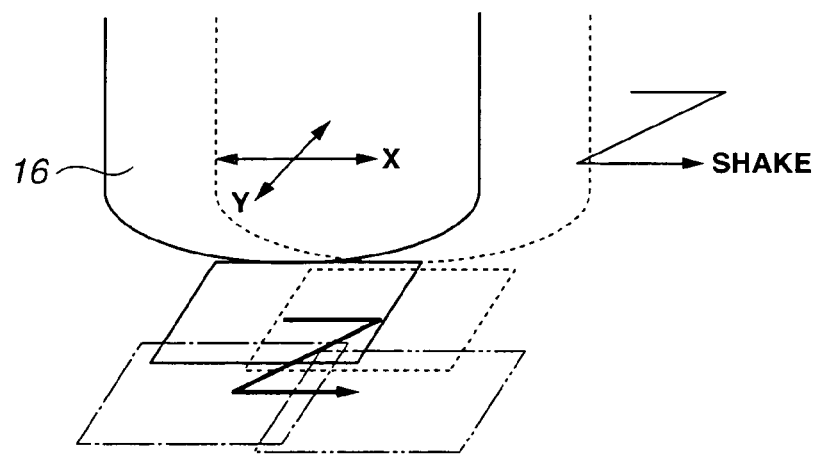
FIG. 21 to FIG. 23 are concerned with a fifth embodiment of the present invention.

As shown in FIG. 21, when the objective unit 16 is shook in, for example, a direction orthogonal to the depth direction, or more particularly, when the objective lens unit 16 is shook as if to draw letter Z in FIG. 21, a relatively scanned range is defined along the trajectory of the shake.

Figure 22:
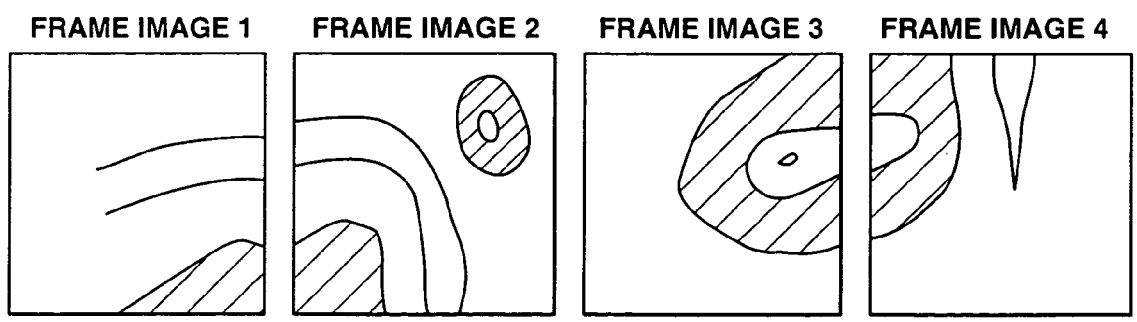

In this case, an object of observation is scanned along bold letter Z in FIG. 21. Two-dimensional images acquired in this case are, as shown in FIG. 22, for example, four frame images 1 to 4. The images partly depict the same region but depict different scanned ranges.

Figure 23:
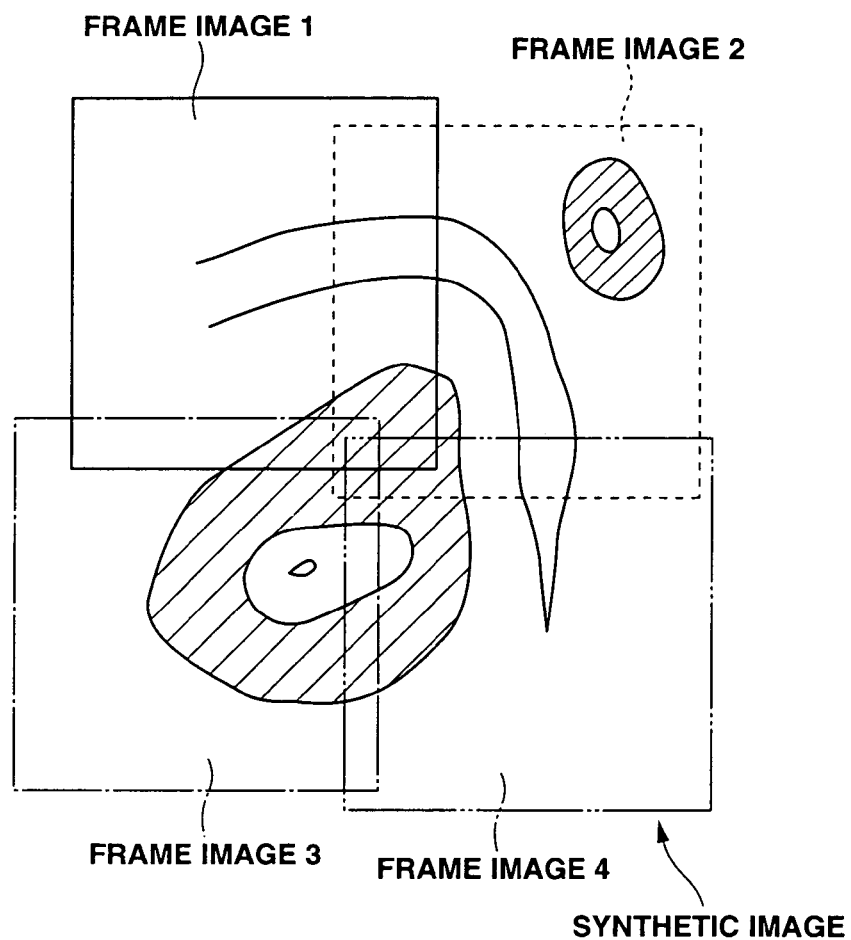

For example, the PC 36 employed in the present embodiment samples a characteristic quantity from each of the images. Based on the characteristic quantities (references), the plurality of images is synthesized (pasted) together so that they will be concatenated. Consequently, a synthetic image like the one shown in FIG. 23 is produced. The synthetic image is then displayed or preserved.

According to the present embodiment, even if a shake occurs, an image of a desired region near an object of observation can be acquired.

Sixth Embodiment

Figure 24:
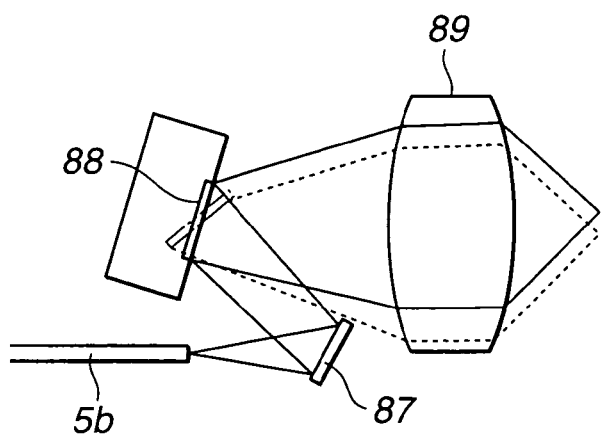

Next, a sixth embodiment of the present invention will be described. FIG. 24 shows an optical scanning means included in the sixth embodiment.

According to the present embodiment, a stationary mirror 87 is obliquely opposed to the optical fiber 5b lying through an optical scanning probe. Light reflected from the stationary mirror 87 is tilted as indicated with a solid line and an alternate long and two short dashes line (in reality, the light is also tilted in a direction vertical to the sheet of paper). The light is thus reflected from a scanning mirror 88 that two-dimensionally sweeps light according to the raster scan method. Thereafter, the light is converged on an objective lens 89 and irradiated to an object of observation.

Figure 25A:
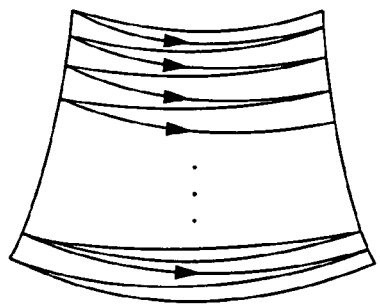
FIG. 25A to FIG. 25D are explanatory diagrams concerning displaying of an image with little distortion produced by masking an image produced using the optical scanning means shown in FIG. 24.
Figure 25B:
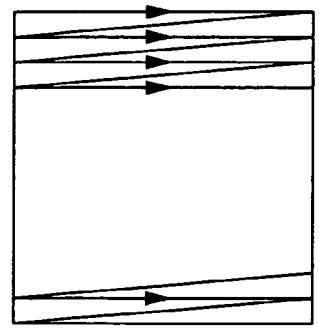

In this case, the trajectory along which light is swept to scan the object of observation is curved as shown in FIG. 25A. Therefore, upon displaying, the raster of scanning lines is corrected into the raster of scanning lines traced when light is swept linearly as shown in FIG. 25B.

Figure 25C:
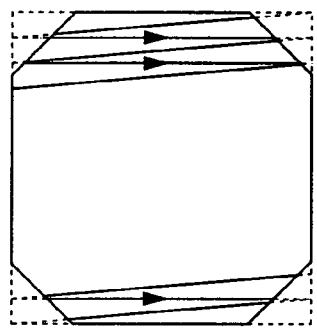

In this case, the margin of the raster, especially, the four corners of the raster are dissociated from the actual raster. Consequently, an image displayed as the raster is likely to distort. According to the present embodiment, therefore, the four corners shown in FIG. 25B are cut, not display, or masked. As shown in FIG. 25C, an image is displayed in an octagonal display area realized with the cut raster.

Figure 25D:
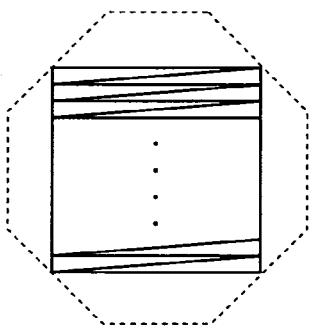

As mentioned above, when the portions of the raster thought to cause a terrible distortion are masked, an image affected with a little distortion can be displayed readily. Incidentally, only the center part of the raster may be, as shown in FIG. 25D, used as the image display area in which an image is displayed. In this case, an image hardly affected by a distortion can be displayed.

Seventh Embodiment

Figure 26:
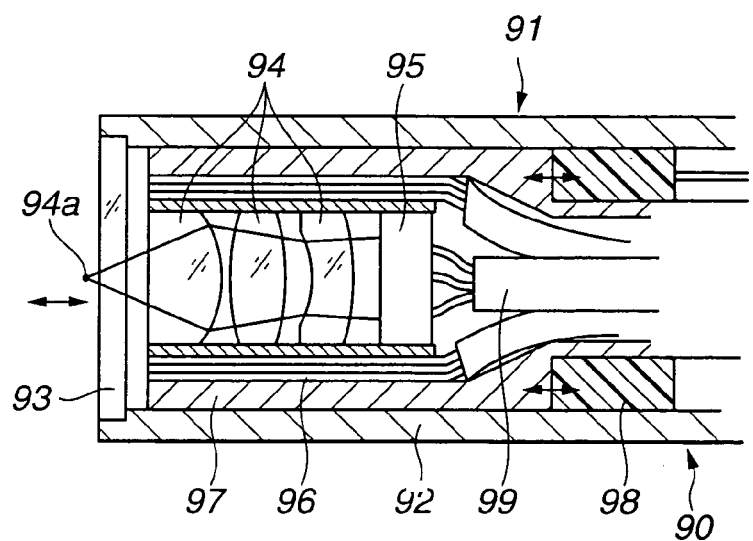
FIG. 26 shows the structure of a high-magnification observing means employed in a seventh embodiment of the present invention.

Next, a seventh embodiment of the present invention will be described below. FIG. 26 shows the structure of the distal section of an optical probe employed in the seventh embodiment. The present embodiment is an optical probe system that does not include the aforesaid two-dimensional scanning means but includes a high-magnification observing means (image pick-up means) that has a means for scanning an object in the depth direction alone (a means that moves in the depth direction alone).

According to the present embodiment, an object to be observed is dyed with a pigment generally adopted for endoscopic observation, such as, methylene blue, and then irrigated. The tip of an optical probe 90 passed through a forceps channel lying through an endoscope is brought into contact with the object for observation. In this case, a tissue or a glandular structure can be observed at a magnification ranging from 500 to 1000.

The distal section 91 of the optical probe 90 shown in FIG. 26 comprises an outer cylinder 92 and a cover glass 93 that shields the distal opening of the outer cylinder 92. An objective lens 94 locked in a lens frame, a CCD 95 located at the position of the image plane of the objective lens 94, and an inner cylinder 97 in which a light guide 96 placed on the periphery of the lens frame is stored are put in the outer cylinder 92 so that they can freely slide.

An actuator 98 is placed on the internal surface of the outer cylinder 92 near the rear end of the distal section 91. The actuator 98 is shaped like, for example, a ring, has the rear end thereof fixed to the outer cylinder 92, has the front end thereof fixed to the inner cylinder 97, and is formed with a piezoelectric element or the like. When a driving signal is applied to the actuator 98, the actuator 98 stretches or contracts as indicated with arrows, and thus moves the inner cylinder 97 in the directions of the optical axis of the objective lens 94.

Incidentally, the rear end of the light guide 96 is coupled to a light source unit that is not shown. Illumination light emanating from the light source unit is propagated along the light guide and emitted from the distal end of the light guide. Thus, an object of observation opposed to the cover glass 93 is illuminated.

Moreover, the CCD 95 is connected to a video processor (or a camera control unit), in which a drive circuit and a video signal processing circuit that are not shown are incorporated, over a signal cable 99. The CCD 95 images the illuminated object of observation via the objective lens 94.

In this case, the objective lens 94 has a large numerical aperture and forms an image at a high magnification. Therefore, an in-focus image is formed only near the focal point 94a of the objective lens 94.

According to the present embodiment, a driving signal is applied to the actuator 98 so that the actuator 98 will stretch or contract. Thus, the objective lens 94 and CCD 95 are moved together with the inner cylinder 97 in the optical-axis directions. The distances of the objective lens 94 and CCD 95 from the cover glass 93 are thus changed. Consequently, similarly to the first embodiment or the like in which the optical scanning probe 11A having an optical scanning means that two-dimensionally scans an object in the depth direction, the present embodiment provides a high-magnification observation image.

Eighth Embodiment

Next, referring to FIG. 27 to FIG. 39, an eighth embodiment of the present invention will be described below.

Figure 27:
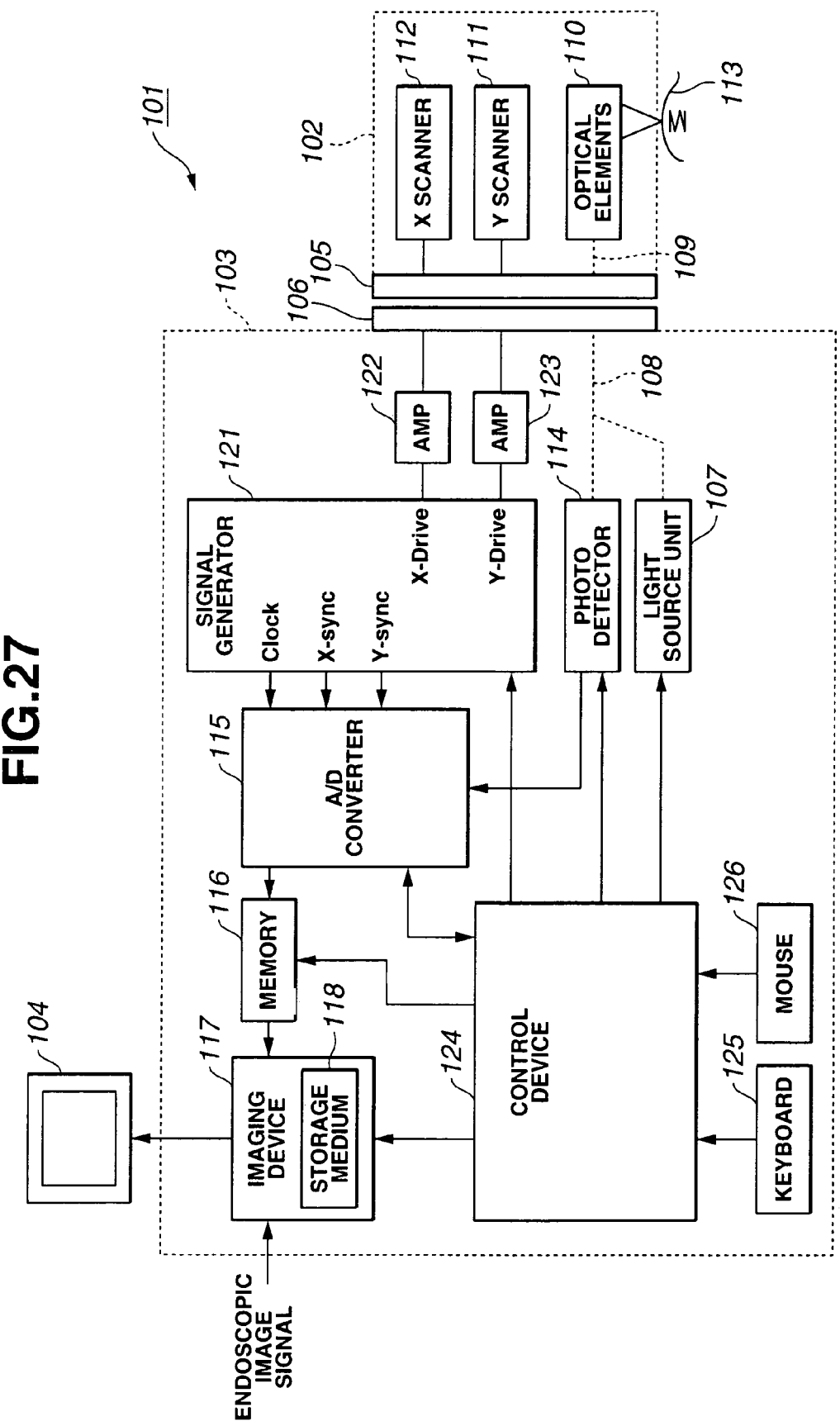

An optical probe system 101 in accordance with the eighth embodiment shown in FIG. 27 comprises: an optical scanning probe 102 of, for example, a confocal type; an observation unit 103 to which the optical scanning probe 102 is freely detachably attached; and a monitor 104 which is connected to the observation unit 103 and on which an image resulting from optical scanning is displayed.

The optical scanning probe 102 can be passed through a channel lying through an endoscope that is not shown. A connector 105 fixed to the rear end of the optical scanning probe 102 is joined to a connector receptacle 106 of the observation unit 103 so that it can be freely detachably attached. With the joint, luminous flux emanating from a light source unit 107 that is incorporated in the observation unit 103 and that is formed with, for example, a semiconductor laser and others is incident on the optical scanning probe 102.

The luminous flux (light beam) emanating from the light source unit 107 travels over an optical fiber 108 and falls on an optical fiber 109, which lies through the optical scanning probe 102, via the connector 105. The light is introduced to the distal section of the optical scanning probe 102 over the optical fiber 109.

An optical element 110 that includes an objective lens and a scanning mirror or the like for converging and irradiating luminous flux is included in the distal section. Luminous flux emitted from the distal end of the optical fiber 109 is converged on or irradiated to an object 113 via the optical scanning mirror and objective lens that are moved in an X or Y direction by an X scanner 111 or a Y scanner 112 serving as a scanning means.

Luminous flux irradiated from the optical element 110 to the object 113 that is an intracorporeal living tissue is two-dimensionally swept in the X and Y directions by means of the X scanner 111 and Y scanner 112. As described later, reflected (return) light is detected in order to acquire two-dimensional image information.

Luminous flux irradiated to the object 113 is partly reflected and routed to the optical element 110. The luminous flux also falls on the distal end of the optical fiber 109. In this case, the distal end of the optical fiber 109 has a small area like a spot. Only light reflected from the focal point on the object 113 falls on the distal end of the optical fiber 109 that has a confocal relationship to the optical element 110.

Light incident on the optical fiber 109 is branched by an optical coupler connected on the optical fiber 108, and received by a photo detector 114. Consequently, the light is photoelectrically converted into an electric signal. The electric signal is transferred to an A/D converter 115, and analog-to-digital converted into digital data. A photomultiplier tube may be substituted for the photo detector 114 serving as a photoelectric conversion means.

The analog-to-digital converted signal is transferred to a memory 116 in which digital data is stored (recorded). Image data representing at least a plurality of frames can be stored in the memory 116. A cine memory that enjoys a large storage capacity and in which a motion picture can be recorded may be adopted as the memory 116.

Image data transmitted through the output terminal of the memory 116 is transferred to an imaging device 117. After an image signal based on which an image can be displayed is produced, the image signal is transmitted to the monitor 104 serving as an image display means. An image resulting from optical scanning or an image produced from light having returned after the optical element 110 included in the optical scanning probe 102 is two-dimensionally moved, or more particularly, an observation image depicting the cells of a living tissue is displayed on the display surface of the monitor 104.

Moreover, the imaging device 117 has a recording medium (or a storage device) 118 such as a hard disk incorporated therein. An image resulting from optical scanning and being displayed on the monitor 104 can be recorded (preserved) in the imaging device 117.

Moreover, the observation unit 103 includes a signal generator 121 that determines the timing of producing an image. A clock to be used as a reference by the signal generator 121, and a sync signal to be used as a reference in producing one frame image, that is, a sync signal X-sync or Y-sync based on which an object is scanned in the X or Y direction are transferred to the A/D converter 115. Synchronously with the clock and sync signal, the A/D converter 115 performs analog-to-digital conversion.

Moreover, the signal generator 121 transmits driving signals X-Drive and Y-Drive, which are synchronous with the respective sync signals, to amplifiers 122 and 123. The X scanner 111 and Y scanner 112 are driven with the driving signals amplified by the amplifiers 122 and 123 respectively.

Moreover, in addition to the X scanner 111 and Y scanner 112, a means for scanning an object in a direction orthogonal to scanning planes to be scanned by the X and Y scanners, or normally, in the depth direction may be included, though the means is not shown in FIG. 27.

Moreover, a control device 124 having a CPU, which controls all the components, incorporated therein is included in the observation unit 103. The control device 124 controls the light source unit 107, photo detector 114, A/D converter 115, memory 116, and imaging device 117.

Figure 38:
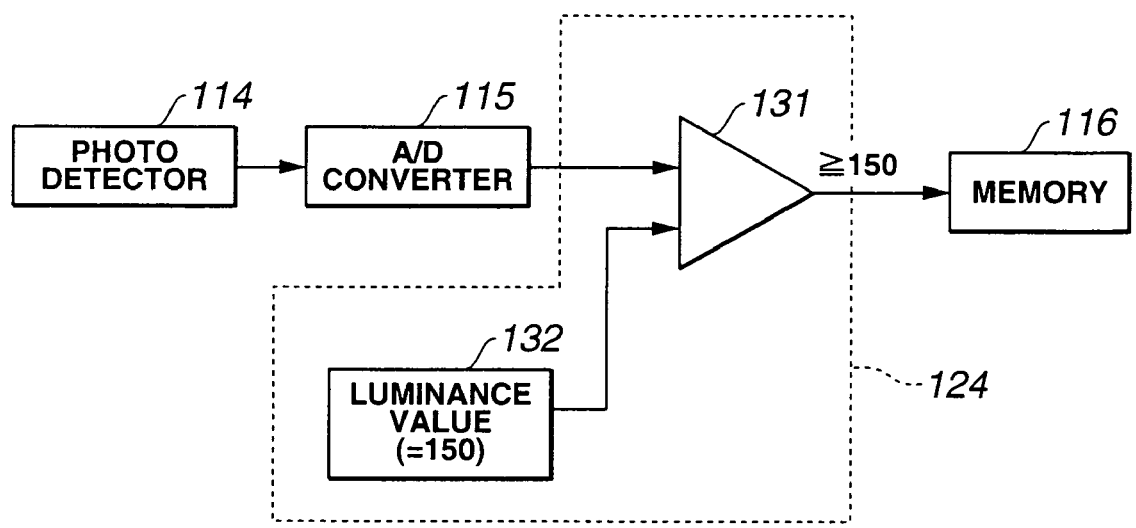

Moreover, as described in conjunction with FIG. 38, the control device 124 can fetch a signal analog-to-digital converted by the A/D converter 115. Furthermore, the control device judges through comparison whether a user-designated display or preservation parameter meets a selected condition.

Moreover, a keyboard 125 whose keys are pressed with a hand and a mouse 126 capable of being clicked and dragged are connected to the control device 124 as a display/preservation selecting means used to select or designate a display or preservation parameter. Incidentally, aside from the mouse 126, an input device having the similar capability, such as, a trackball may be adopted.

Aside from the optical scanning probe 102 utilizing confocal optical elements, an optical scanning probe that utilizes low-coherent light emanating from a low-coherent light source so as to produce an optical observation image will do.

Moreover, according to the present embodiment, an endoscopic image signal sent from a video processor or a camera control unit, which is included in an endoscope system that is not shown and produces an endoscopic image, is transferred to the imaging device 117. The imaging device 117 transmits the endoscopic image and an image resulting from optical scanning to the monitor 104 via a mixer or the like. Both the images are displayed on the monitor 104.

Moreover, the CPU that is included in the control device 124 and is not shown extends control according to programs stored in a ROM or the like that is not shown and that is incorporated in the control device 124.

In this case, control is extended as described with reference to FIG. 28 or the like so that an image resulting from optical scanning (specifically, an observation image depicting the cells of a living tissue) will be displayed on the monitor 104, a display/preservation mode permitting preservation in the recording medium 118 will be selected or designated, a reference for selection will be designated, and the image resulting from optical scanning will be displayed or preserved under a selected or designated condition.

Specifically, the present embodiment includes a display/preservation selecting means that permits selection of a display/preservation parameter with which a condition for display on the monitor 104 or preservation in the recording medium 118 is determined. A user handles the keyboard 125 or mouse 126 for selection or designation. The control device 124 controls the imaging device 117 that processes a signal so as to produce an image and the light source unit 107 so that an image will be displayed or preserved under a user-designated condition.

As mentioned above, the control device 124 extends control so that an image will be displayed or preserved under a condition a user has selected or designated in advance. Consequently, only an observation image depicting cells and meeting a user-designated condition for preservation is preserved, but an observation image depicting cells, not meeting the condition, and being unnecessary is not preserved.

Consequently, editing work needed to preserve only an observation image that depicts cells and that is thought to be required later becomes unnecessary or can be simplified. Since unnecessary observation images depicting cells are not recorded (unlike the related art), a storage capacity will not be limited (in other words, a filing capacity can be lessened). Required images depicting cells can be stored efficiently. This leads to improved maneuverability.

Moreover, as described later, display/preservation parameters with which display or preservation is designated may be presented on the monitor 104 on which an observation image depicting cells is displayed. A user can determine the parameters with the observation image depicting cells left viewable. Moreover, the determined settings can be checked easily. This contributes to improvement of user-friendliness (maneuverability).

Next, referring to FIG. 28, a display/preservation mode that can be selected according to the present embodiment will be detailed below.

Figure 28:
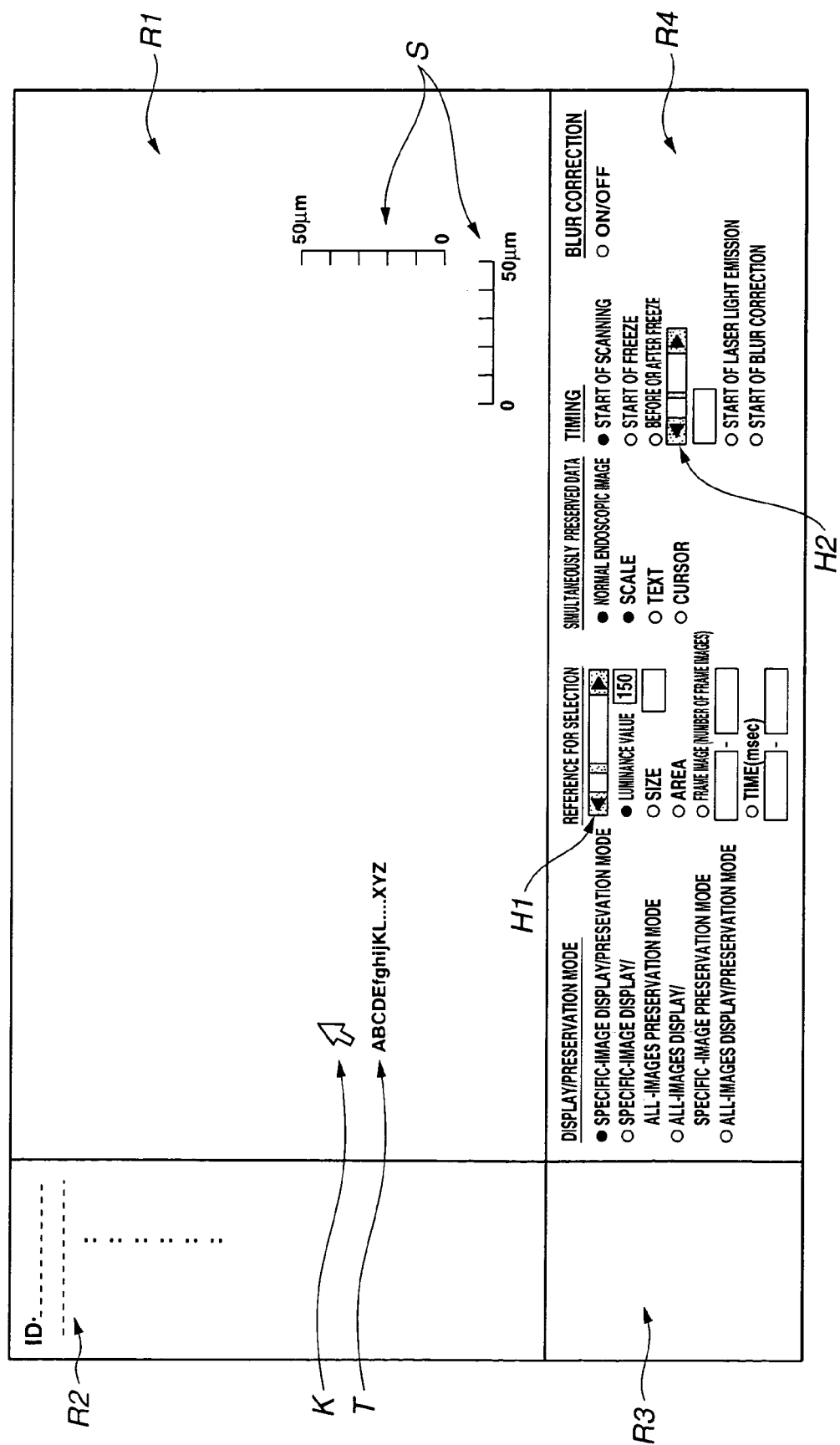

As shown in FIG. 28, a cell observation image display area R1 in which an observation image depicting cells, that is, an image resulting from optical scanning performed by the optical scanning probe 102 is displayed is defined in the right upper part of the display surface of the monitor 104. A patient information display area R2 in which patient information is displayed is defined in the left upper part of the display surface of the monitor 104. A normal endoscopic image display area R3 in which a normal endoscopic image is displayed is defined in the left lower part of the display surface of the monitor 104. A display/preservation parameter designation window R4 in which display/preservation parameters are designated is defined in the right lower part of the display surface of the monitor 104.

In the cell observation image display area R1, in addition to an observation image depicting cells and being produced by the optical scanning probe 102, a scale S indicating the size of a cell and a cursor K freely movable using the mouse 126 can be displayed at any positions. Using the keyboard 125, a text T can be displayed at any position while being superimposed on the observation image.

Moreover, in the display/preservation designation window R4, various conditions for display or preservation such as a display/preservation mode, a reference for selection, simultaneously preserved data, timing, and whether blur correction is effected are presented and can be determined. When the parameters are selected or designated, the information of the designated parameters is stored in a memory that is not shown and is incorporated in the control device 124. The control device 124 extends control so that display and/or preservation will be executed based on the selected or designated parameters (which will be described in conjunction with the flowchart of FIG. 30).

Four display/preservation modes are presented as display/preservation modes. Specifically, a specific-image display/preservation mode, a specific-image display/all-images preservation mode, an all-images display/specific-image preservation mode, and an all-images display/preservation mode are supported.

The specific-image display/preservation mode is a mode in which a specific image is displayed and preserved.

The specific-image display/all-images preservation mode is a mode in which a specific image is displayed and all images are preserved.

The all-images display/specific-image preservation mode is a mode in which all images are displayed and a specific image is preserved.

The all-images display/preservation mode is a mode in which all images are displayed and preserved.

A user selects a desired one of the four modes using the input device such as the keyboard 125 or mouse 126. Thus, a display/preservation mode can be selected. A white circle ○ or a black circle ● drawn at the heads of the mode names of the four modes including the specific-image display/preservation mode signifies that the designation of the mode is invalidated (off) or validated (on). The same applies to the designations of other conditions including the reference for selection.

Incidentally, the all-images display/preservation mode is designated as an initial setting. The present invention is not limited to this designation. Any of the other three modes may be designated as the initial setting (which will be described in conjunction with the flowchart of FIG. 31).

Moreover, when the mode for displaying or preserving a specific image is selected as a display/preservation mode, the specific image can be specified based on a reference for selection. The reference for selection is selected from among five items or parameters such as a luminance value, a size, an area, a frame image, and a time. Incidentally, the size is a reference for selection additionally selected when the luminance value is selected as the reference for selection (it can therefore be said that major references for selection are the other four references of selection).

Moreover, a horizontal bar H1 is displayed below the heading of Reference for Selection. The horizontal bar H1 makes it easy to determine the value of a parameter selected as a reference for selection.

When the luminance value is selected as a reference for selection, it means that an image whose luminance value is equal to or higher than a certain luminance value (luminance level) of an image should be selected as a specific image.

Specifically, for example, a luminance value is expressed with, for example, 8 bits and ranges from 0 to 255. The luminance value of 255 is the maximum value. Initially, the luminance value is designated and set to 255. The present invention is not limited to this setting. Alternatively, any luminance value may be adopted. Moreover, other item or parameter may be designated as an initial reference for selection.

When the reference for selection is set to the luminance value, the horizontal bar H1 below the heading of Reference for Selection shown in FIG. 28 is clicked using the keyboard 125 or mouse 126. According to the number of clicks, the luminance value can be easily set to any value ranging from 0 to 255 (8 bits).

In the example of FIG. 28, • signifies that the luminance value is selected as a reference for selection and set to 150 using the horizontal bar H1. In this case, when a specific image is selected or designated, if the luminance value of the specific image is equal to or larger than 150, the specific image is displayed or preserved.

Moreover, when "size" is selected as a reference for selection, it means that if an image displayed in the cell view display area R1 or an image preserved depicts a cell having the size, the image is displayed or preserved.

Moreover, when "area" is selected as a reference for selection, it means that an image in a display area or a preservation area is displayed or preserved.

Figure 29:
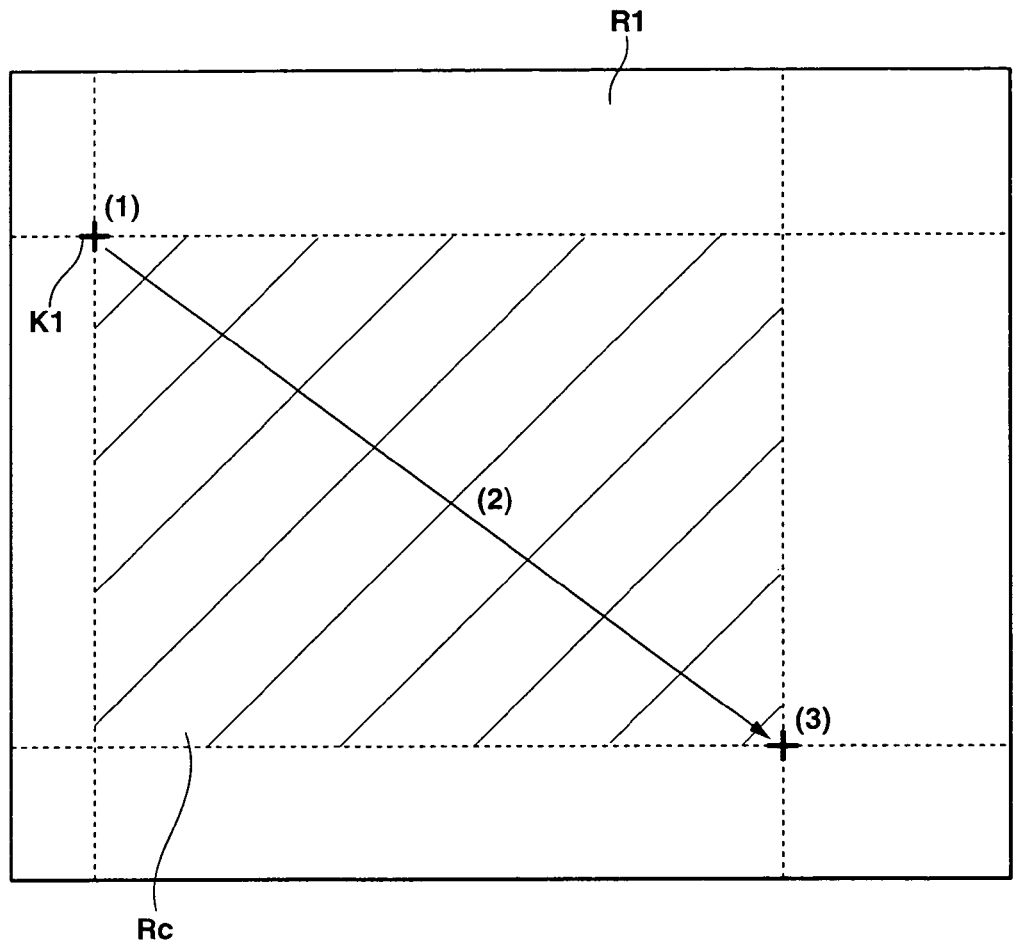

In this case, a cross cursor K1 like the one shown in FIG. 29 appears. The keyboard 125 or mouse 126 is used to click and drag the cursor. A defined area Rc (serving as a reference for selection) that is a hatched area in the drawing is designated as a display area or a preservation area.

Figure 33:
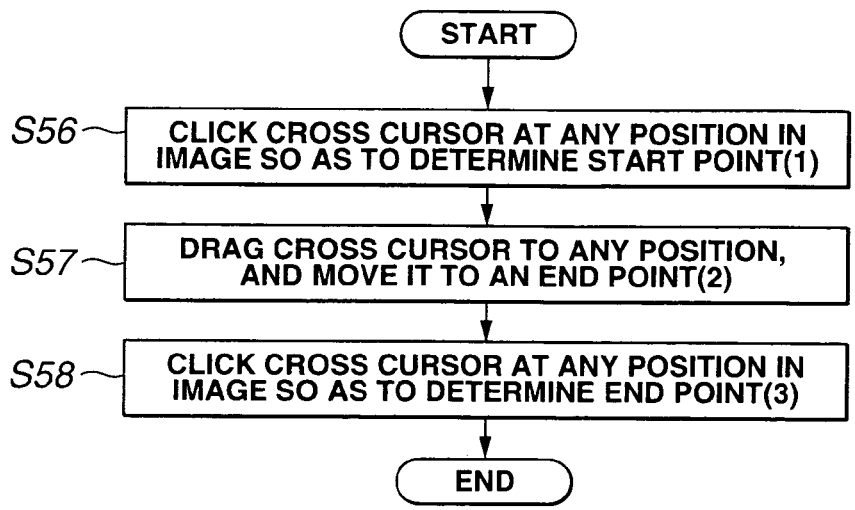

Specifically, as described in the flowchart of FIG. 33, at the first step S56, the cross cursor K1 is clicked at any position in an image in order to determine a start point (indicated with (1)). At the next step S57, the cross cursor K1 is dragged to any position (indicated with (2)) and finally moved to an end point.

At the next step S58, the cross cursor K1 is clicked at any position in the image in order to determine the end point (indicated with (3)). Thus, an area Rc serving as a reference for selection is defined.

When the frame image (data representing one frame image) is selected as a reference for selection, the horizontal bar H1 below the heading of Reference for Selection in FIG. 28 is clicked using the keyboard 125 or mouse 126 in order to designate a certain number of frame images to be displayed or preserved during a period from the start of display or preservation to the end thereof (in FIG. 28, any value ranging from 0 to 160).

When the time is selected as a reference for selection, the horizontal bar H1 below the heading of Reference for Selection in FIG. 28 is clicked using the keyboard 125 or mouse 126 in order to designate the time required from the start of display and/or preservation to the end thereof (in FIG. 28, any value ranging from 0 to 8000 msec).

Moreover, the simultaneously preserved data that is data to be simultaneously preserved with an observation image depicting cells can be selected from among a normal endoscopic image, a scale S, a text T, and a cursor K. For the aforesaid references for selection, one item or parameter can be selected. However, for this parameter or item, a plurality of items or parameters can be selected. In FIG. 28, the normal endoscopic image and scale S are selected as simultaneously preserved data.

Moreover, the timing signifies the condition that display and/or preservation of a specific image should be started at what timing. The timing may be selected from among items or parameters such as start of scanning, execution of freeze (freezing an image), before or after execution of freeze (before or after an image is frozen), start of laser light emission, and start of blur correction.

When the start of scanning is selected, a specific image is displayed at the timing of starting scanning, that is, optical scanning. When the execution of freeze is selected, a specific image is displayed at the timing of starting freezing (displaying a still image). When before or after execution of freeze is selected, the number of frame images preceding or succeeding a frame image that is frozen is designated as the timing of displaying an image.

In this case, a horizontal bar H2 is, like the horizontal bar H1 below the heading of Reference for Selection, displayed below the heading of Before or After Execution of Freeze. Similarly to the horizontal bar H1, the horizontal bar H2 is clicked in order to designate the number of frame images preceding or succeeding a frame image that is frozen. Consequently, a specific image is displayed at the timing.

When a user selects the start of laser light emission, a specific image is displayed at the timing that the laser starts oscillation (emitting light). When the start of blur correction is selected, a specific image is displayed at the start of blur correction.

Thus, the condition that display and/or preservation of an image should be started or stopped at what timing is designated.

Moreover, in the rightmost item of Blur Correction, whether blur correction should be performed is designated. When it is designated that blur correction should be performed, ON is highlighted. When it is designated that blur correction should not be performed, OFF is highlighted.

Next, the operation of the present embodiment will be described with reference to FIG. 30 and others.

Figure 30:
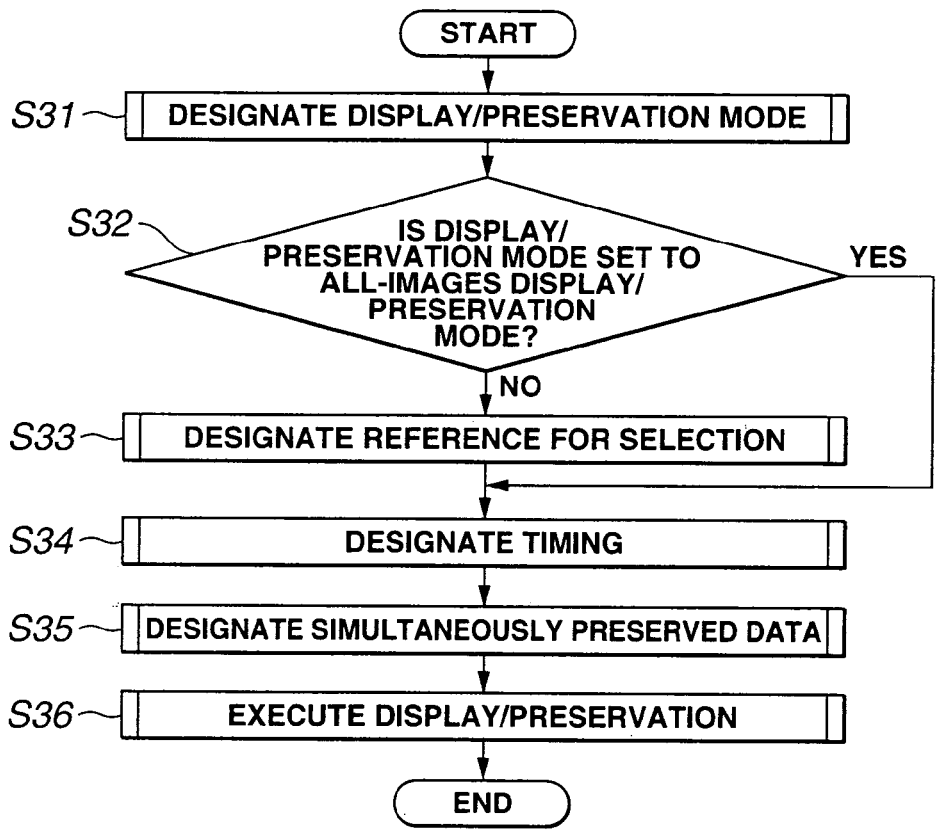

FIG. 30 describes a process ranging from designation of a display/preservation method to execution of display/preservation. When the power supply of the optical probe system 101 is turned on, the optical probe system starts up. At step S31, a display/preservation mode is designated.

Figure 31:
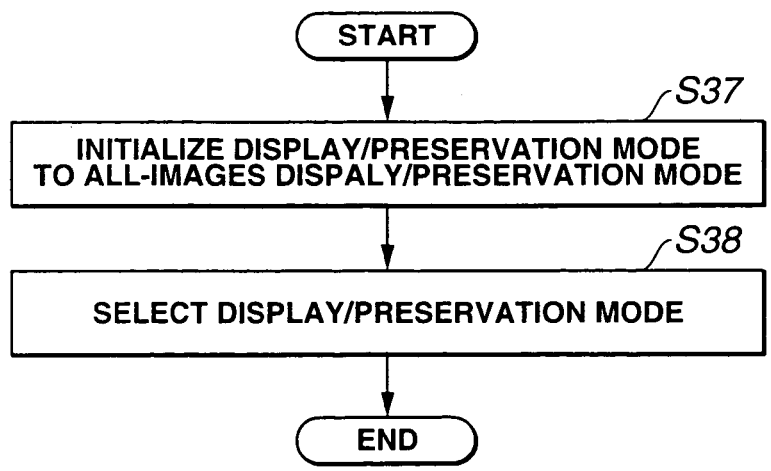

The display/preservation mode designation is detailed in FIG. 31. When the designation of a display/preservation mode is started, a display/preservation mode is initialized to the all-images display/preservation mode at step S37. At the next step S38, any of the display/preservation modes other than the all-images display/preservation mode is selected.

When the step S31 of the designation of a display/preservation mode described in FIG. 30 is completed, it is judged at step S32 whether the display/preservation mode is set to the all-images display/preservation mode. If the display/preservation mode is not set to the all-images display/preservation mode, a reference for selection is designated at step S33. Control is then passed to step S34. The designation of a reference for selection is detailed in FIG. 32.

On the other hand, if it is judged at step S32 that the display/preservation mode is not set to the all-images display/preservation mode, control is passed to the step S34 of designation of timing. The designation of timing is detailed in FIG. 8.

When the designation of timing is completed, step S35 of designation of simultaneously preserved data and step S36 of execution of display/preservation are carried out. The process described in FIG. 30 is then terminated. The step S35 of designation of simultaneously preserved data and the step S36 of execution of display/preservation are detailed in FIG. 35 and FIG. 37 respectively.

Figure 32:
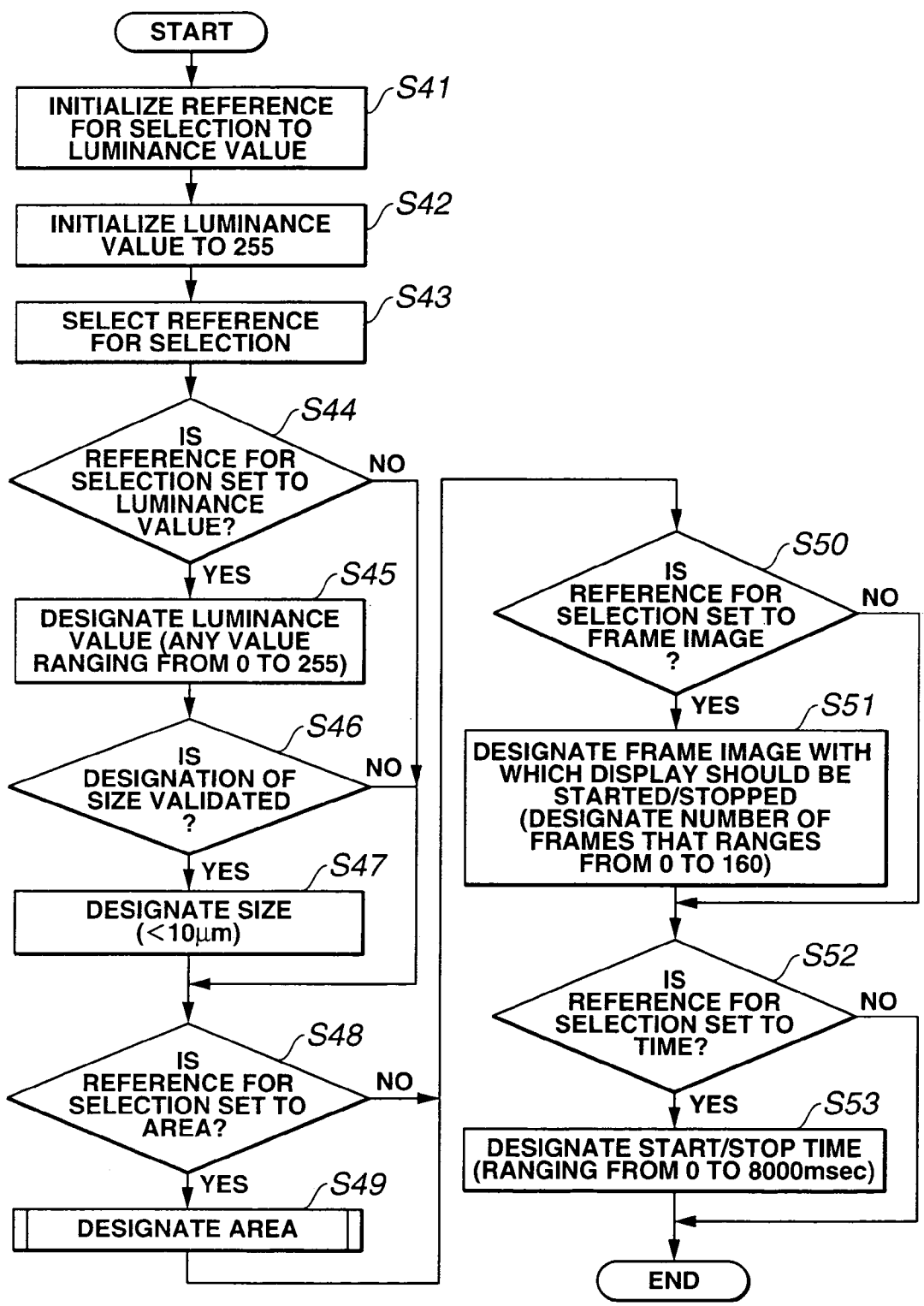

Next, the designation of a reference for selection will be described in conjunction with FIG. 32.

When the designation of a reference for selection is started, a reference for selection is initialized to a luminance value at step S41. The luminance value is initialized to 255 at step S42. Thereafter, control is passed to step S43 of selecting a reference for selection.

At step S44, a user is prompted to designate whether the luminance value is selected as a reference for selection. When the user selects the luminance value as the reference for selection, the luminance value is set to any value ranging from 0 to 255 at step S45. At the next step S46, the user is prompted to designate whether the designation of a size is validated (on). If the designation of a size is validated (on), the size is designated at step S47. For example, the size is set to 10 µm or less. Control is then passed to step S48.

On the other hand, if the user does not select the luminance value as a reference for selection, control is passed to step S48. At step S48, the user is prompted to designate whether an area is designated as a reference for selection. If the user selects the area, an area is defined at step S49. The definement of an area has been detailed with reference to FIG. 33.

When the definement of an area is completed, the user is prompted at step S50 to designate whether a frame image is selected as a reference for selection. If the user selects the frame image, the user designates with what frame image display should be started or stopped, or in other words, the number of frame images preceding a frame image with which display should be started/stopped at step S51. Control is then passed to step S52. As a concrete example of the step S51 of designating with which frame image display should be started or stopped, the user designates the number of frames ranging from 0 to 160.

If the user does not select a frame image at step S50, control is passed to step S52. At step S52, the user is prompted to designate whether a time is selected as a reference for selection. If the user selects a time, the user designates a start/stop time at step S53. The process described in FIG. 32 is then terminated.

As a concrete example of the designation of a start/stop time, a user designates a time ranging from, for example, 0 to 8000 msec. If a time is not selected, step S53 is skipped and the process described in FIG. 32 is terminated.

Next, the designation of timing will be described in conjunction with FIG. 34.

When the designation of timing is started, the timing is initialized to the start of scanning at step S61. At step S62, timing is selected. At step S63, a user is prompted to designate whether the start of blur correction is selected as timing. If the user selects the start of blur correction, the user is prompted at step S64 whether designation of blur correction is invalidated (off).

If the user designates that designation of blur correction is invalidated (off), since the designation is inconsistent with the selection made at step 63, control is returned to step S63. On the other hand, if the start of blur correction is not selected as timing, control is passed to step S65, the user is prompted to designate whether the timing before or after execution of freeze is selected as timing. If the user selects the timing before or after execution of freeze, the user designates at step S66 the number of frame images preceding or succeeding a frame image that is frozen.

Figure 34:
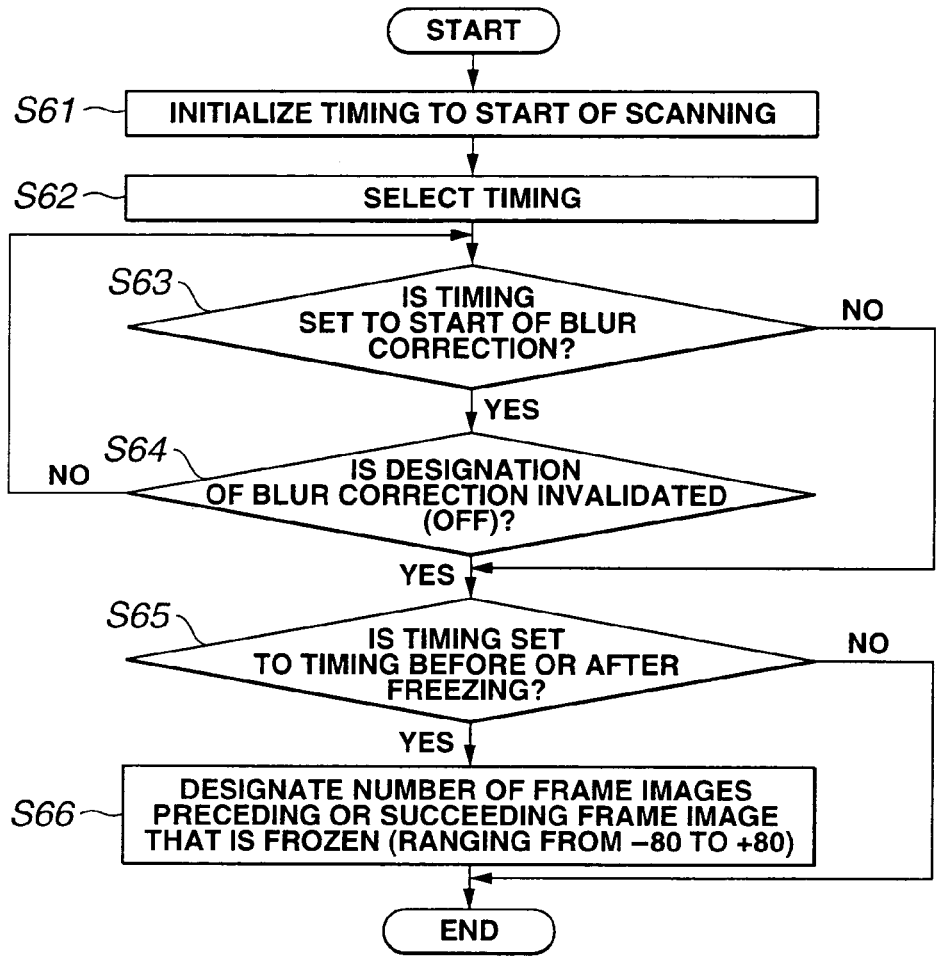

Specifically, the user designates the number of frame images ranging from, for example, −80 to +80, and the process described in FIG. 34 is terminated. If the timing before or after execution of freeze is not selected as timing at step S65, step S66 is skipped and the process described in FIG. 34 is terminated.

Figure 35:
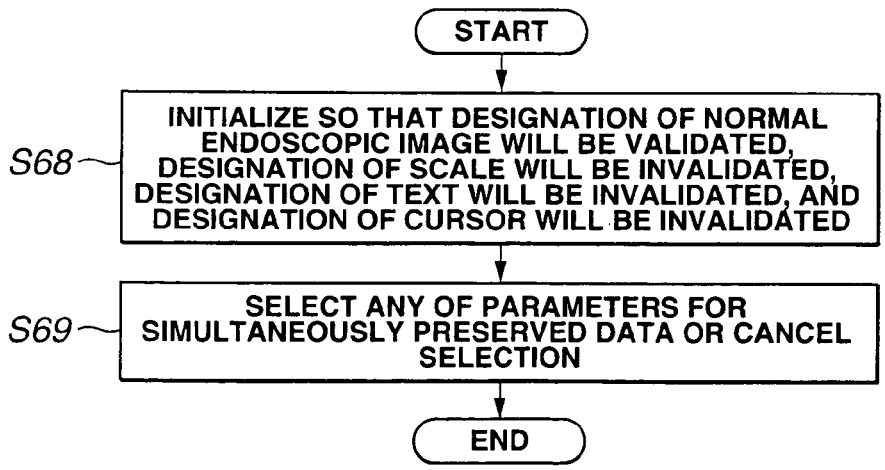

Next, designation of simultaneously preserved data will be described in conjunction with FIG. 35 below.

When the designation of simultaneously preserved data is started, initialization is performed at step S68 so that designation of a normal endoscopic image will be validated (on), designation of a scale will be invalidated (off), designation of a text will be invalidated (off), and designation of a cursor will be invalidated (off). At the next step S69, any of the parameters for simultaneously preserved data is selected or selection is canceled. In other words, a user selects a parameter different from the initially selected parameter at step S69, and the process described in FIG. 35 is terminated.

After the designation of various parameters is terminated, a specific image is displayed or preserved based on the settings. Consequently, a specific image can be displayed or preserved based on user-designated settings.

As listed in FIG. 36A and FIG. 36B, the number of settings for display and/or preservation comes to 80 in total.

FIG. 36A and FIG. 36B lists the number of patterns of display/preservation parameters conceivable in a case where a reference for selection is selected from among the parameters of a luminance value, an area, a freeze, and a time. As described in the flowchart of FIG. 32, if a plurality of items or parameters, for example, both the luminance value and area are made selective as references for selection, the number of patterns of display/preservation parameters becomes much larger.

Typical examples of settings will be successively described with reference to FIG. 37, FIG. 40, FIG. 41, FIG. 43, FIG. 46, and FIG. 48 respectively.

Figure 37:
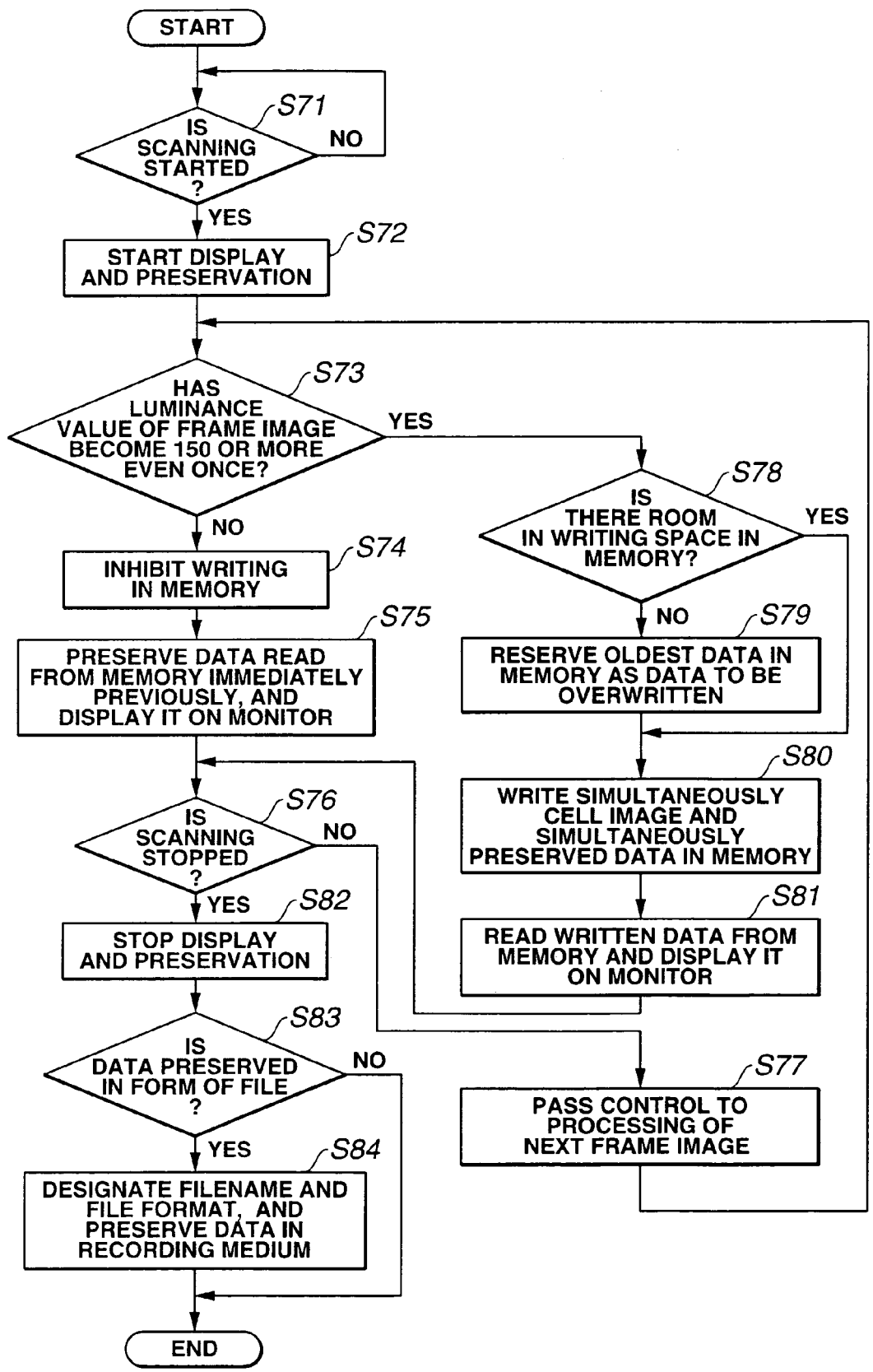

The flowchart of FIG. 37 describes operations to be performed in a case where: similarly to an example of display shown in FIG. 28, a display/preservation mode is set to the specific image display/preservation mode; a reference for selection is set to a luminance value (=150); designation of a size is invalidated (off); timing is set to the start of scanning, designation of blur correction is invalidated (off); and simultaneously preserved data is set to a normal endoscopic image and a scale.

When the power supply of the optical probe system 101 is turned on, the optical probe system starts up. The control device 124 enters an operating state and waits at step S71 in FIG. 37 until scanning is started.

When scanning is started, the control unit 124 starts display and preservation at step S72. At the next step S73, the control device 124 judges whether the luminance value of a frame image has become 150 or more even once.

FIG. 38 shows the circuitry of a signal processing system that judges whether a reference for selection is set to a luminance value and whether a signal which represents an observation image depicting cells and whose luminance signal component has a level equal to or larger than a predetermined luminance value has been received.

For example, as shown in FIG. 38, an output signal of the A/D converter 115 is applied to one input terminal of a comparator 131 included in the control device 124. Moreover, a luminance value (=150) stored in a parameter storage unit 132 included in the control device 124 is applied as a reference value to the other input terminal of the comparator 131. The comparator 131 judges whether a view signal depicting cells and exhibiting a luminance value equal to or higher than the reference luminance value (=150) has been received. Based on an output signal of the comparator 131, writing a signal in the memory 116 is controlled.

If the luminance value of a frame image has not become 150 or more even once, the control device 124 inhibits writing in the memory 116 at step S74. At the next step S75, immediately before writing in the memory 116 is inhibited, data is read from the memory 116. The data is held in a display RAM and displayed on the monitor 104. Control is then passed to step S76.

In other words, if the luminance value of a frame image has not become 150 or more even once, the latest data representing a previous frame image and containing a luminance value that has become 150 or more even once is read. The data is held in the display RAM, and kept displayed on the monitor 104.

The control device 124 judges at step S76 whether scanning is stopped. If scanning is not stopped, control is passed to step S77 of processing the next frame image. After control is passed to the processing of the next frame image, control is returned to step S73.

If it is judged at step S73 that the luminance value of a frame image has become 150 or more even once, the control device 124 judges at step S78 whether the writing space in the memory 116 has room to store data representing one frame image and other data (more accurately, room to store data representing one frame image, image data, and simultaneously preserved data). If the writing space has no room, the oldest data in the memory 116 is reserved as data to be overwritten at step S79. Control is then passed to step S80.

On the other hand, if the writing space in the memory 116 has room to store data representing one frame image and other data, control is passed to step S80. The control device 124 simultaneously writes an observation image depicting cells (cell image in FIG. 37) and simultaneously preserved data in the memory 116 at step S80. Thereafter, control is passed to step S81.

At step S81, the written data is read from the memory 116, and displayed on the monitor 104. Thereafter, control is passed to step S76. It is then judged as mentioned above whether scanning is stopped. If scanning is not stopped, control is returned to step S73 via step S77.

If a user designates at step S76 that scanning should be stopped, control is passed to step S82. The control device 124 stops display and preservation.

At step S83, the user is prompted to designate whether data is preserved in the form of a file. Assume that the user designates that data should be preserved in the form of a file. In this case, at step S84, a filename and a file format are designated, and the data is preserved on the recording medium 118. The process described in FIG. 37 is then terminated.

If the user does not designate at step S83 that data should be preserved in the form of a file, preservation on the recording medium 118 is not carried out, but the process described in FIG. 37 is then terminated.

Figure 39:
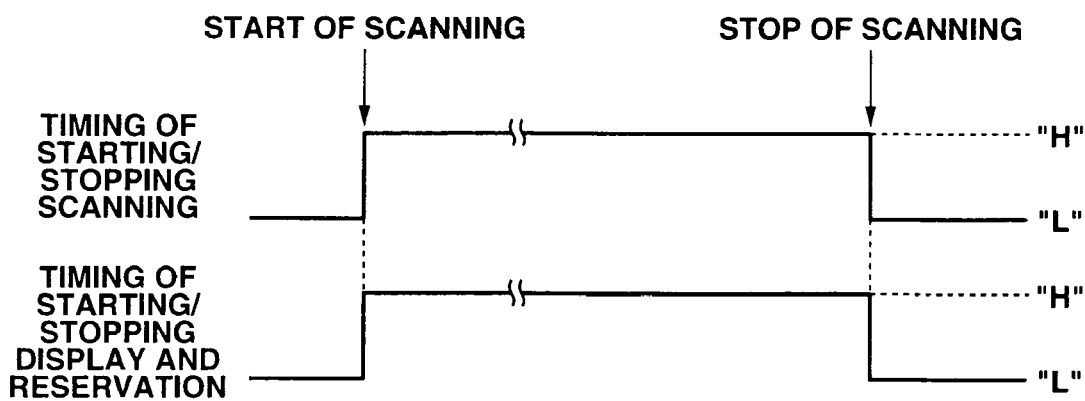

FIG. 39 is a timing chart indicating the timings of the operations described in FIG. 37. As shown in FIG. 39, display and preservation are started simultaneously with start of scanning. Moreover, the display and preservation are stopped simultaneously with stop of scanning. After scanning is stopped, image data recorded in the memory 116 can be preserved in a predetermined file format in the recording medium 18 (for example, a magnetic disk such as a hard disk, or a magneto-optical disk such as a CD-R disk, an MO disk, or a DVD-R disk). The filename can be designated arbitrarily, and the file format may be the multi tagged image file format (TIFF) in which a multi-still image file is stored, the audio video interleave (AVI) file format, or the MPEG-1 or MPEG-2 file format in which a motion picture file is stored.

Next, referring to FIG. 40, the second typical example of operations will be described below. In this case, when the parameters are selected or designated as shown in FIG. 28, the designation of a size is validated (on).

Specifically, the conditions for display/preservation are identical to those concerning FIG. 37 except that the designation of a size is validated. More particularly, a display/preservation mode is set to the specific-image display/preservation mode, a reference for selection is set to a luminance value (=150), designation of a size is validated (on), timing is set to the start of scanning, designation of blur correction is invalidated (off), and simultaneously preserved data is set to a normal endoscopic image and a scale. Operations to be performed for display/preservation under these conditions will be described below.

For example, when a frame image depicts a cell having a size of 10 μm, if the number of pixels constituting a display image is a product (approximately 200,000 pixels) of 512 by 512, the number of pixels whose luminance values are 150 or more is about 10,000.

Therefore, if a luminance value is 150 or more and the number of pixels constituting one frame image is 10,000, the frame image depicts a cell. The frame image is therefore displayed or preserved.

Figure 40:
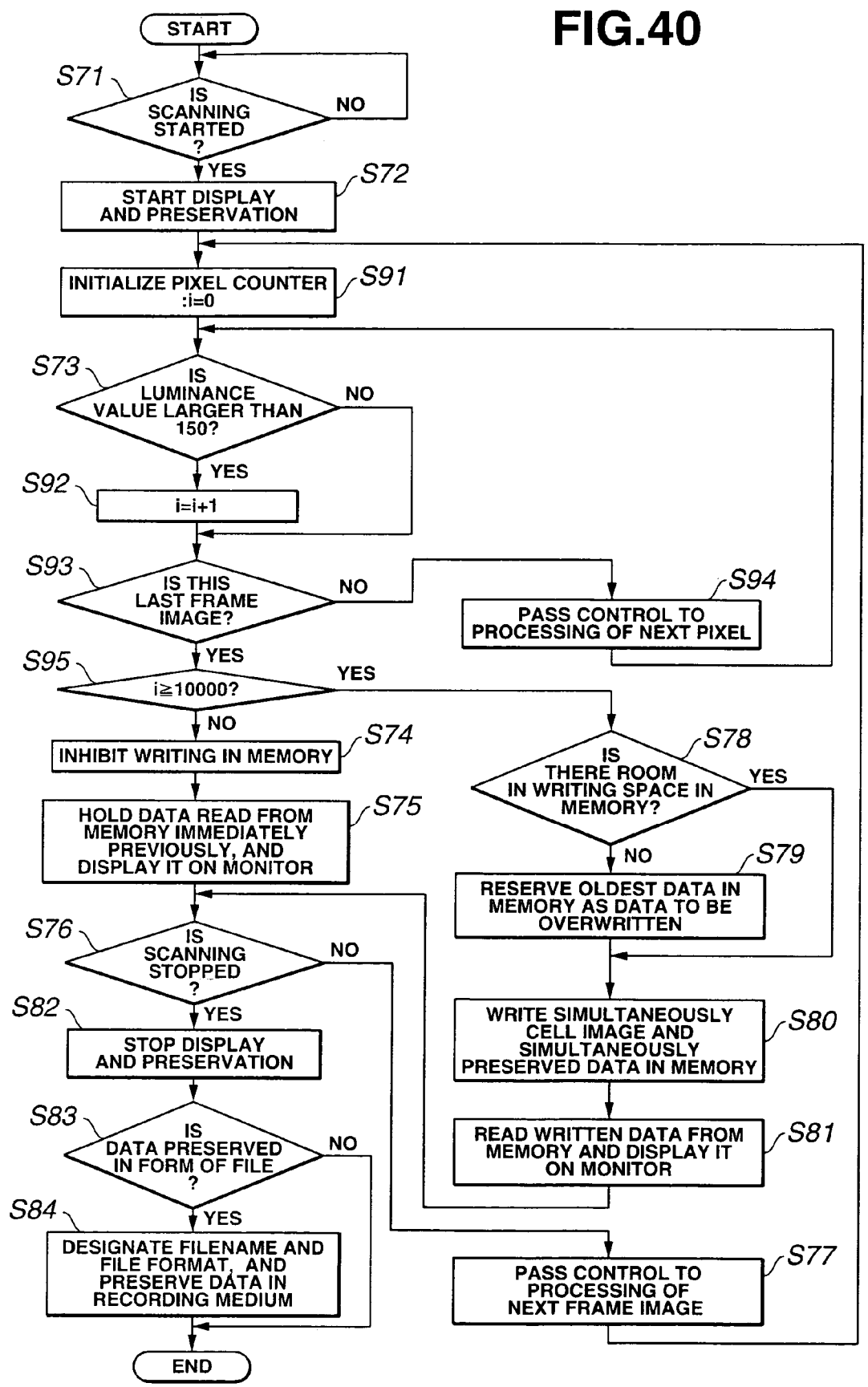

The flowchart of FIG. 40 is identical to the flowchart of FIG. 37 except that step S91 is inserted between steps S72 and S73 (or more particularly, similar step S43'), and steps S92 to S95 are inserted between step S73 and step S74. The fundamental difference from FIG. 37 will be described below.

When a process is started, similarly to FIG. 37, steps S71 and S72 are performed. Thereafter, step S91 of initialization of a pixel counter is performed. Specifically, a count variable i is reset to 0. Thereafter, at step S73', the control device 124 judges whether a luminance value contained in received image data (of each pixel) is equal to or larger than 150 (serving as a reference luminance value).

If the above condition is met, the count variable i is incremented by one at step S92. At the next step S93, it is judged whether the frame image is the last one. If the frame image is not the last one, control is passed to step S94 of processing the next pixel. Control is then returned to step S73'. At step S73', if the luminance value of a received pixel is not equal to or larger than 150, step S92 is skipped and control is passed to step S93.

At step S93, if the frame image is the last one, control is passed to step S95. The control device 124 judges whether the count variable i is equal to or larger than 10,000 (that is, i≧10,000). If the condition is met, it is judged that the frame image depicts a cell having a size of 10 μm. Control is then passed to step S78, and data is written in the memory 116.

On the other hand, if it is found at step S95 that the condition is not met, control is passed to step S74. Writing in the memory 116 is inhibited. The latest data previously written in the memory 116 is read and displayed on the monitor 104.

The other operations are identical to those described in FIG. 37.

Next, the third typical example will be described. In this case, a display/preservation mode is set to the specific-image display/all-images preservation mode, a reference for selection is set to an area, timing is set to the execution of freeze (display of a still image), designation of blur correction is invalidated (off), and simultaneously preserved data is set to a text.

Whatever are the settings for blur correction and simultaneously preserved data, it does not influence a process. Therefore, the description of the settings will be omitted. In this case, only a still image falling within an area Rc defined through definition of an area described in conjunction with FIG. 29 is displayed, and all the pixels constituting the still image are preserved. An input device such as the keyboard 125 or mouse 126 is used to freeze an image. This initiates a process described in the flowchart of FIG. 41.

When the optical scanning probe system starts up, the control device 124 waits until scanning is started at step S101. Thereafter, at step S102, the control device 124 waits until freeze is directed.

When freeze is directed, the control device 124 judges at step S103 whether the writing space in the memory 116 has room. If the writing space has no room, the oldest data in the memory 116 is reserved as data to be overwritten at step S104. At the next step S105, an observation image depicting cells and simultaneously preserved data are written simultaneously in the memory 116. Control is then passed to the next step S106.

On the other hand, if the writing space in the memory 116 has room at step S103, control is passed to step S105.

At step S106, written data is read from the memory 116 and displayed on the monitor 104. At the next step S107, it is judged whether a pixel concerned lies outside the defined area Rc (for brevity's sake, the reference numeral Rc is omitted from FIG. 41 but only the defined area is stated).

If the pixel concerned lies outside the defined area Rc, the control device 124 resets the luminance value of the pixel to 0 at step S108. In other words, the luminance value of a pixel outside the defined area Rc is determined so that the pixel will appear in black. Thereafter, the control device 124 judges at step S109 whether the frame image is the last one. If the frame image is not the last one, control is passed to step S110 of processing the next pixel. Control is then returned to step S107.

On the other hand, if it is judged at step S107 that the pixel concerned lies within the defined area Rc, the control device 124 passes control to step S109. If the control device 124 judges at step S109 that the frame image is the last one, an observation image depicting cells within the defined area Rc is displayed on the monitor 104 at step S111.

Figure 41:
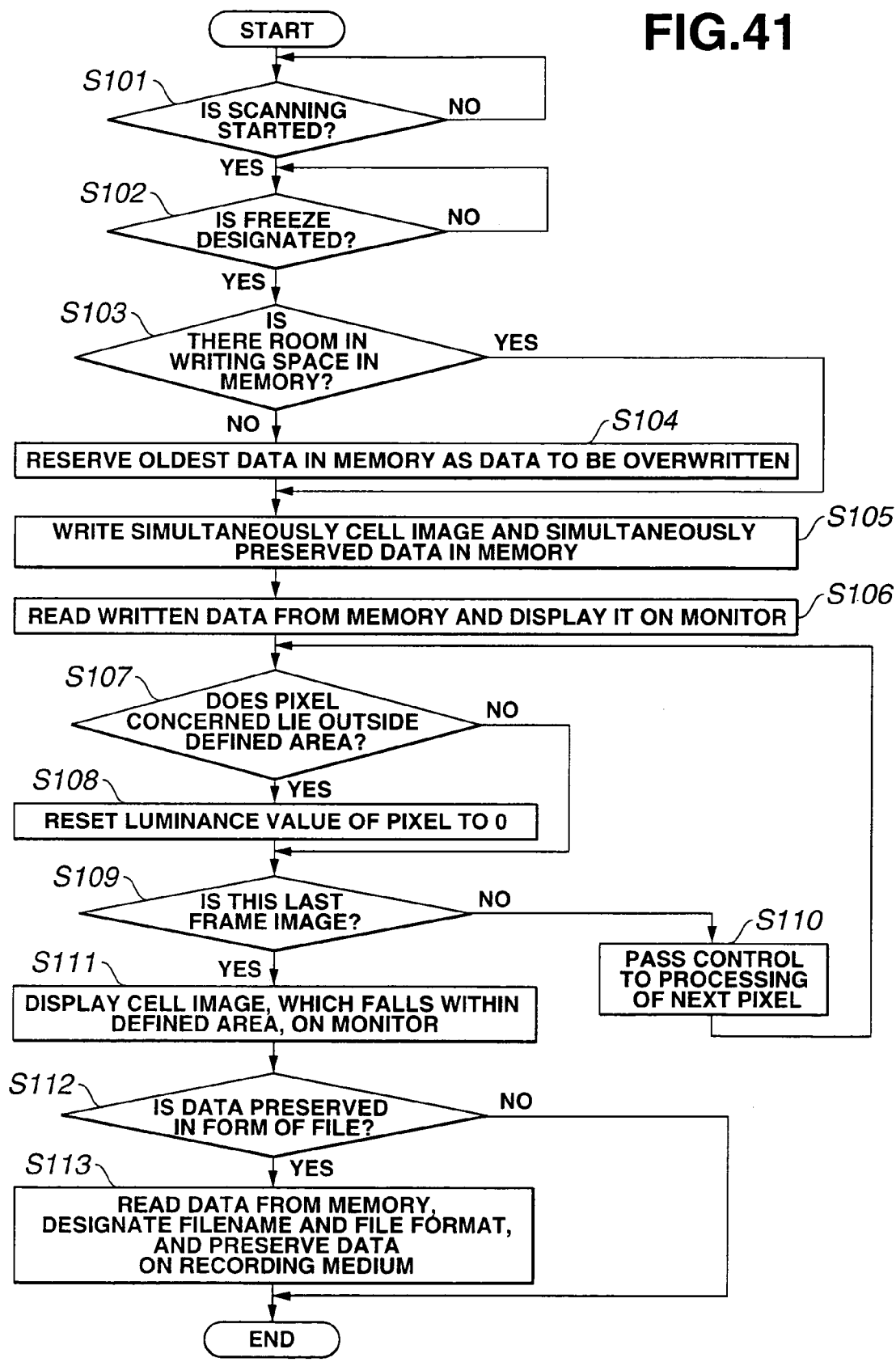

Thereafter, at the next step S112, the control device 124 prompts a user to designate whether data should be stored in the form of a file. If the user designates that data should be stored in the form of a file, the data is read from the memory 116, and preserved on the recording medium 118 with a filename and a file format designated. The process described in FIG. 41 is then terminated. If data should not be stored in the form of a file, step S113 is skipped and the process described in FIG. 41 is terminated.

Figure 42:
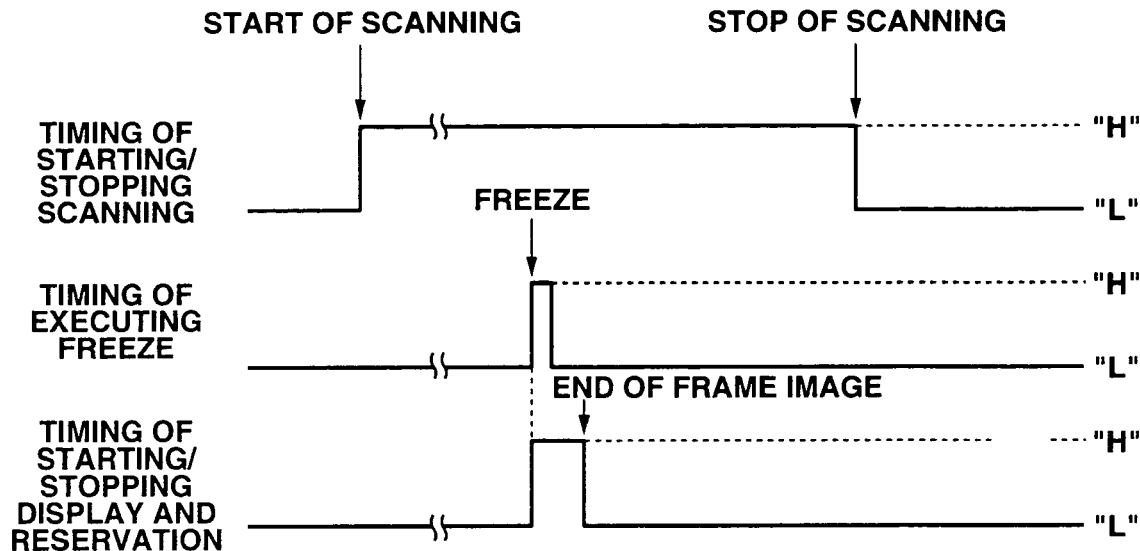

FIG. 42 is a timing chart indicating operations performed as described in FIG. 41. As shown in FIG. 42, when scanning is started, all still images are recorded in the memory 116 at the timing that freeze is executed, that is, the timing that freeze is designated and a freeze designation signal is transmitted. The control device 124 extends control so that among the images represented by the data read from the memory 116, only an image falling within the defined area Rc will be displayed as a still image.

Image data recorded in the memory 116 is preserved on the recording medium 118 according to a certain file format. Any filename can be assigned, and the file format may be the TIFF or BMF in which data is stored as a still image file.

Next, the fourth typical example will be described below. In this case, a display/preservation mode is set to the all-images display/specific-image preservation mode, a reference for selection is set to a frame image, the number of frames is 50 ranging from frame image 1 to frame image 50, timing is set to the timing before or after execution of freeze (timing point is −10), designation of blur correction is invalidated (off), and simultaneously preserved data is set to a cursor.

Whatever are the settings for blur correction and simultaneously preserved data, it will not influence a process. The description of the settings will be omitted. In this case, display and preservation are started at the timing that precedes the timing of freezing a frame image by ten frame-image productions. Only frame images ranging from frame image 1 to frame image 50 are preserved, and a still image of a frame image preceding ten frame images is displayed. An input device such as the keyboard 125 or mouse 126 is used to freeze a frame image. Consequently, data that is written in the memory 116 ten frame-image productions previously is read and displayed as described in the flowchart of FIG. 43 and the timing chart of FIG. 44.

Furthermore, when data is preserved in the form of a file, fifty consecutive frame images starting with a frame image produced ten frame images previously are preserved.

Figure 43:
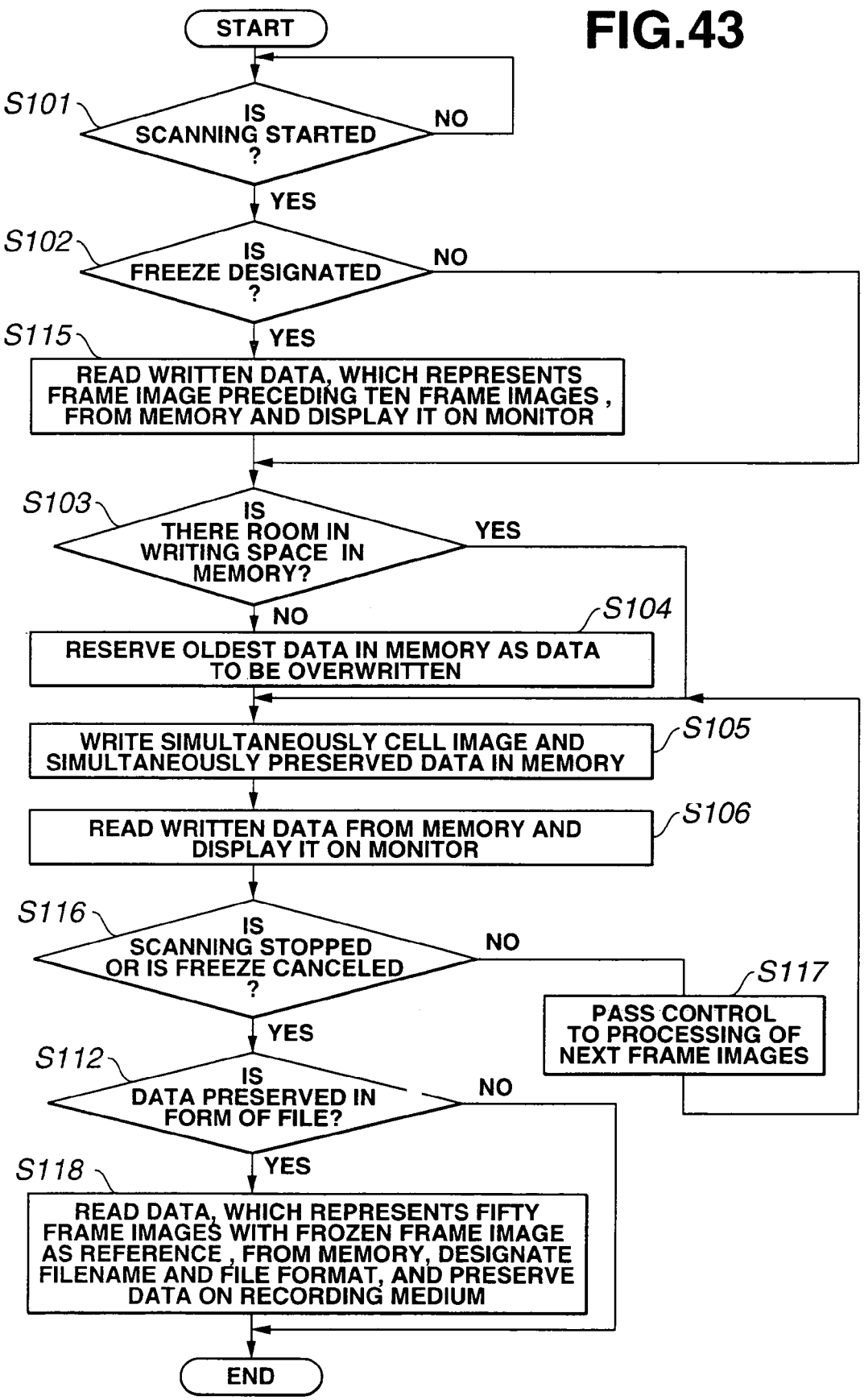

Referring to FIG. 43, operations performed will be described. Similarly to FIG. 41, the control device 124 waits at step S101 until scanning is started. At the next step S102, it is judged whether freeze is directed.

If freeze is directed, the control device 124 reads data, which is written ten frame-image productions previously, from the memory 116 at step S115, and permits the data to be displayed on the monitor 104. Control is then passed to the next step S103. Step S103 to step S106 are identical to those in FIG. 41. Namely, data read from the memory 116 is displayed on the monitor 104.

Thereafter, the control device 124 judges at step S116 whether scanning is stopped or freeze is canceled. If neither scanning is stopped nor freeze is canceled, control is passed to step S117 of processing the next frame image. Control is then returned to step S105.

On the other hand, if it is found at step S102 that freeze is not directed, the control device 124 jumps control to step S115, and executes step S103.

Moreover, if it is judged at step S116 that scanning is stopped or freeze is canceled, control is passed to step S82. The control device 124 prompts a user to designate whether data should be preserved in the form of a file. If the user does not designate the preservation, the control device 124 does not preserve data but terminates the process. If the user designates the preservation, the control device 124 reads data, which represents 50 frame images starting with a frozen image, from the memory 116 at step S118. The data is then preserved on the recording medium 118 with a filename and a file format designated. The process described in FIG. 43 is then terminated.

Figure 44:
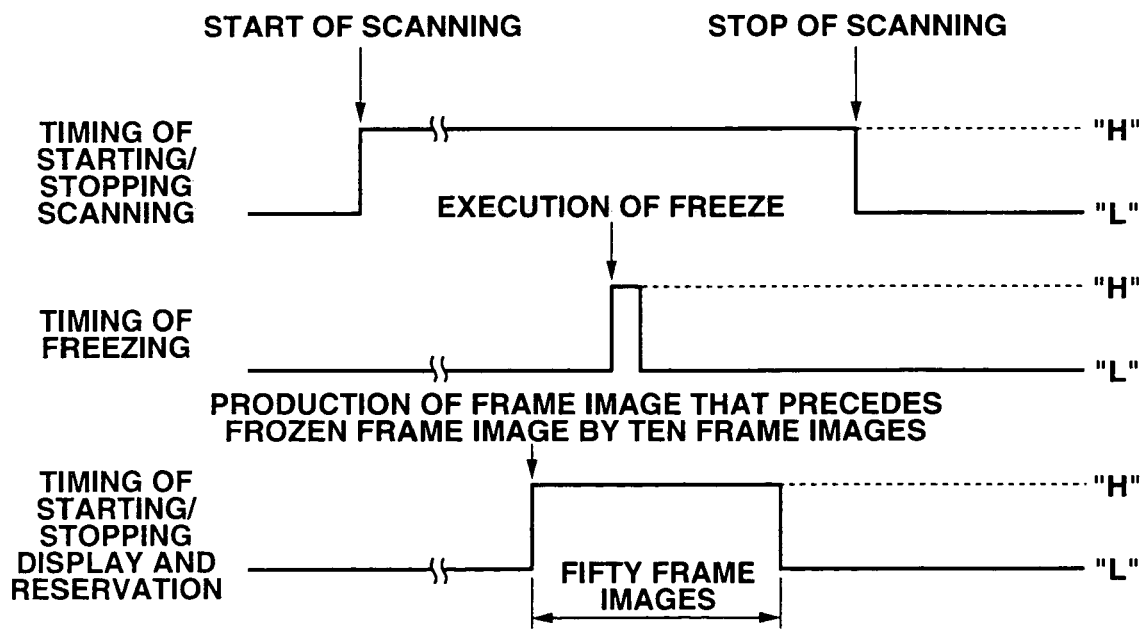

FIG. 44 shows the timings of starting and stopping display and preservation according to the process described in FIG. 43. After scanning is started as shown in FIG. 44, if freeze is directed, data written ten frame-image productions previously is read from the memory 116, and displayed and preserved.

Figure 45:
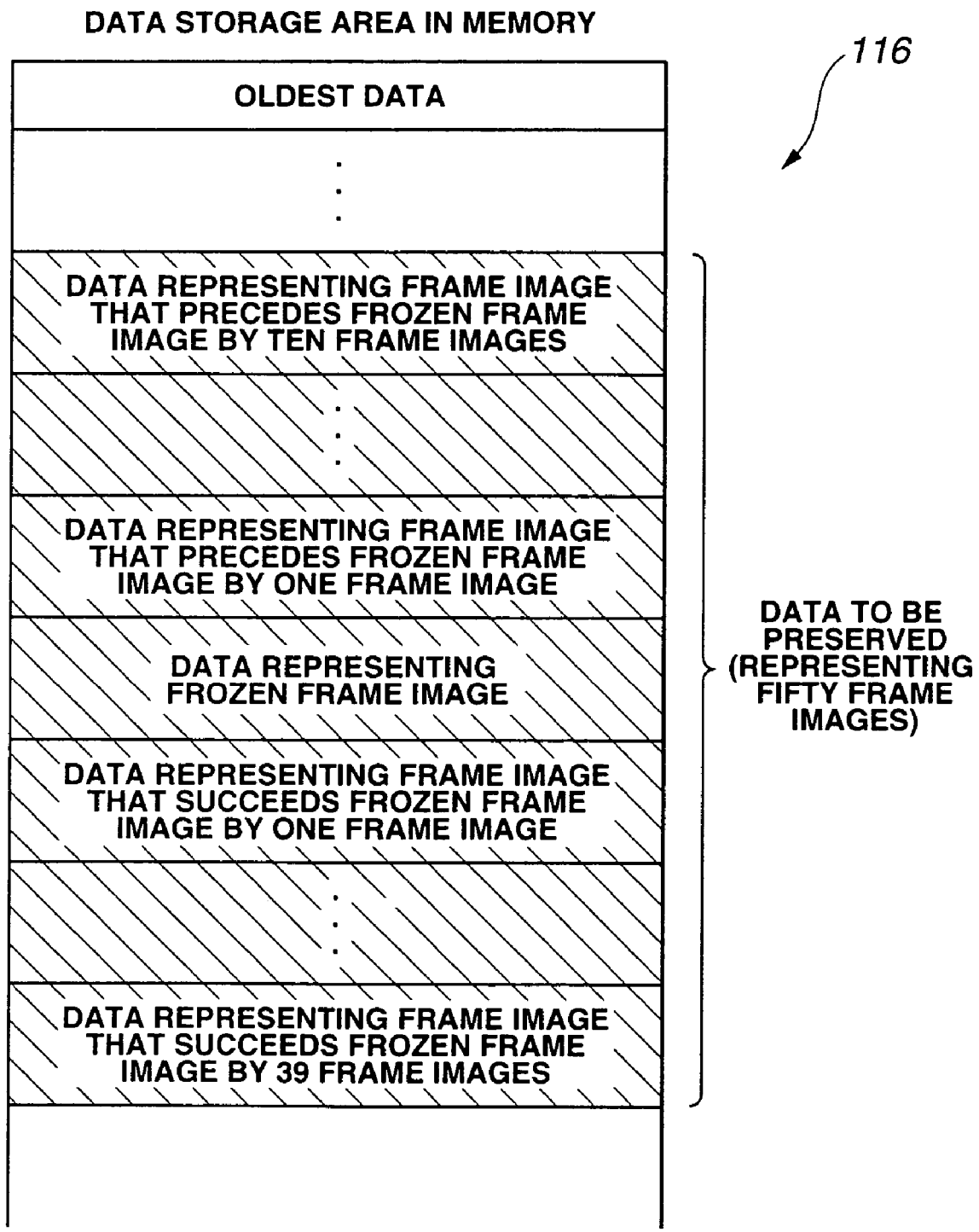

Moreover, FIG. 45 shows the state of the memory 116 in which data is stored. As shown in FIG. 45, data representing 50 frame images that start with a frame image produced ten frame-image productions previous to the timing of directing freeze is preserved.

Referring to FIG. 44, scanning continues after the timing of stopping display/preservation, that is, the timing that the designated number of frame images has been displayed or preserved. If scanning stops before the designated number of frame images has been displayed or preserved, display/preservation is stopped at the timing (consequently, in this case, a smaller number of frame images than 50 frame images is displayed or preserved).

Next, the fifth typical example will be described below. In this case, a display/preservation mode is set to the specific-image display/preservation mode, a reference for selection is set to a time, a designated time is 1000 msec, timing is set to the start of laser light emission, designation of blur correction is invalidated (off), and simultaneously preserved data is set to a normal endoscopic image.

Whatever are the settings for blur correction and simultaneously reserved data, it does not influence a process. The description of the settings will therefore be omitted.

Operations will be briefed below. As described in FIG. 46 and FIG. 47, when timing is set to the start of laser light emission, the timing of turning on or off the laser agrees with the timing of starting or stopping scanning. Therefore, a process is analogous to the one described in the flowchart of FIG. 37. However, when the timing disagrees with the timing of starting or stopping scanning, display and preservation are performed only during laser light emission. Thus, display and preservation of unnecessary images can be omitted.

Figure 47:
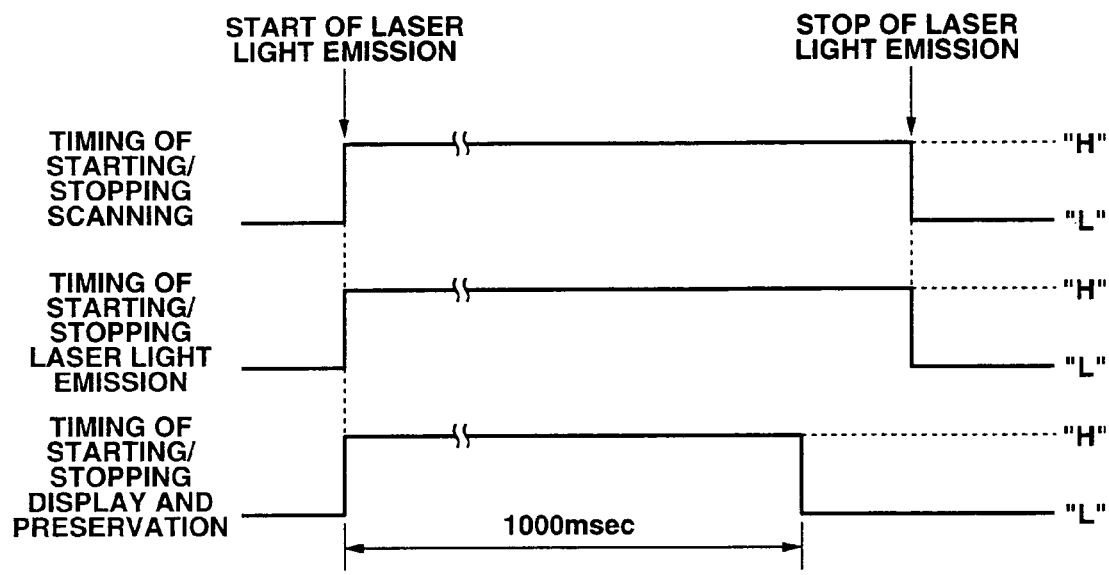

Similarly to the fourth typical example, as shown in FIG. 47, if laser light emission (or scanning) is stopped before the reference for selection is met, that is, the time of 1000 msec elapses, display or preservation is stopped at the timing.

Figure 46:
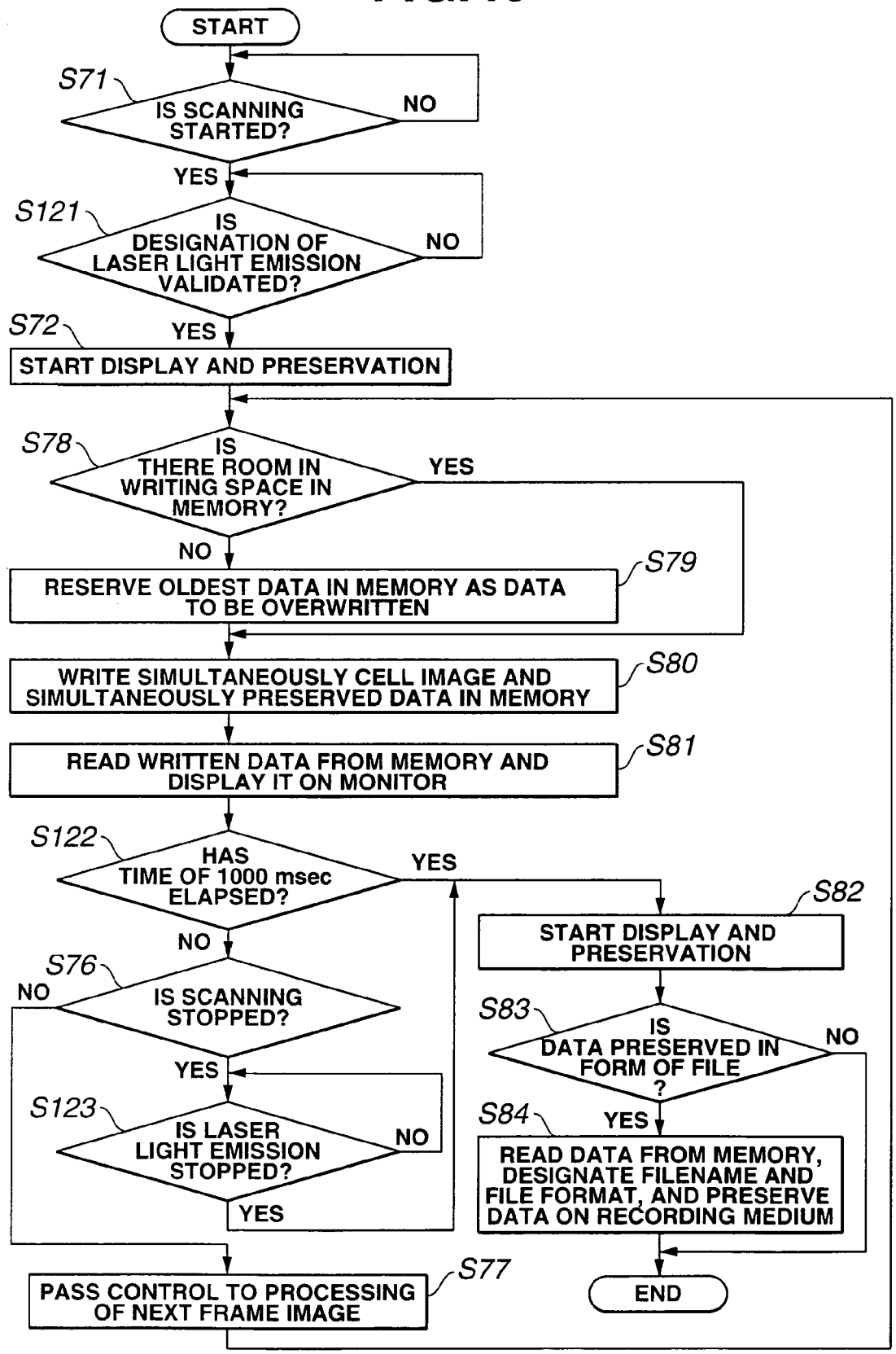

Next, a description will be made with reference to the flowchart of FIG. 46. Operations described in FIG. 46 are analogous to those described in the flowchart of FIG. 37. The same step numbers as those in FIG. 37 will be employed.

Similarly to the process described in FIG. 37, at the first step S71, the control device 124 waits until scanning is started. At the next step S121, the control device 124 waits until the laser is turned on. Thereafter, at step S72, display and preservation are started. At step S78, it is judged whether the writing space in the memory has room.

Step S78 to step S81 are the same as those in FIG. 37. Thereafter, the control device 124 judges at step S122 whether the time of 1000 msec has elapsed. If the time has not elapsed, it is judged at step S76 whether scanning is stopped.

If scanning is not stopped, control is passed to step S77 of processing the next frame image. Control is then returned to step S78. If scanning is stopped, it is judged at step S123 whether laser light emission is stopped. A wait state continues until the laser light emission is stopped. Thereafter, control is passed to step S82 of stopping display and preservation. Thereafter, similarly to the process described in FIG. 37, control is passed to step S83 and step S84.

If the control device 124 judges at step S122 that 1000 msec has elapsed, the control device 124 passes control to step S82.

As mentioned above, FIG. 47 is the timing chart indicating the timings of the foregoing operations. Referring to FIG. 47, the start of laser oscillation is synchronous with the start of scanning, and the stop of laser oscillation is also synchronous therewith.

Next, the sixth typical example will be described below. In this case, a display/preservation mode is set to the all-images display/preservation mode, timing is set to the start of blur correction, designation of blur correction is validated (on), and simultaneously preserved data is set to a scale. Whatever is the setting for simultaneously preserved data, it does not influence a process. The description of the setting will therefore be omitted.

In this case, preservation is started at the timing that blur correction is started using an input device such as the keyboard 125 or mouse 126 (when it is designated in advance that blur correction is performed, blur correction is started synchronously with the start of scanning). Preservation continues until blur correction is canceled or scanning is completed (refer to the flowchart of FIG. 48 and the timing chart of FIG. 49).

Figure 49:
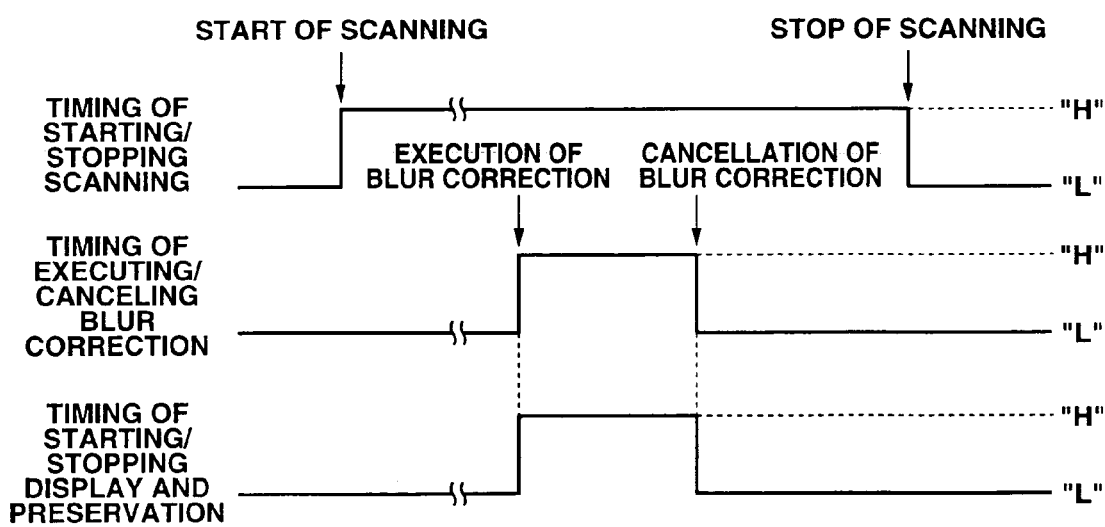
Figure 48:
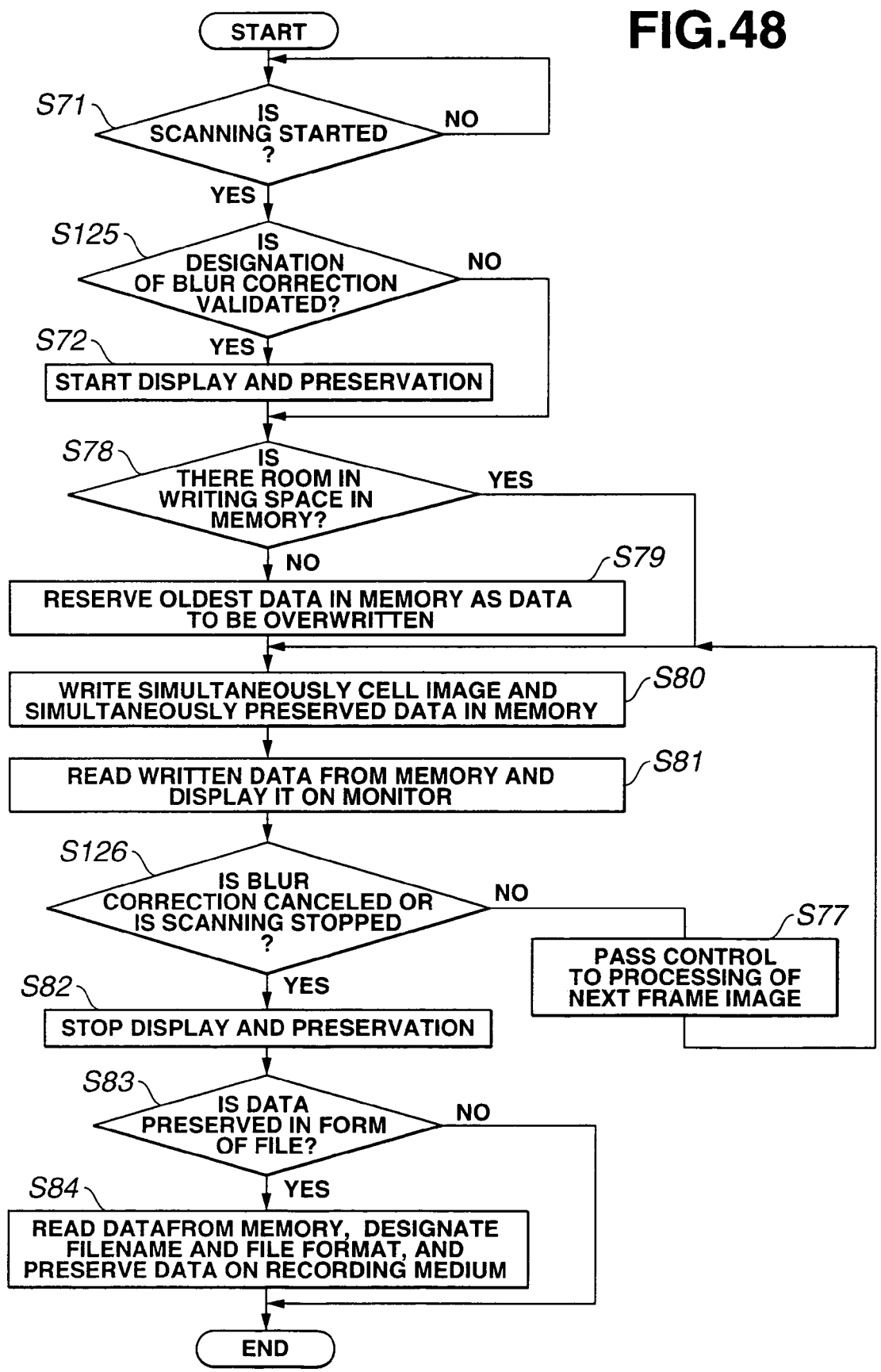

Referring to FIG. 48 and FIG. 49, if scanning is stopped before blur correction is stopped, preservation is stopped at the timing.

Moreover, blur correction is implemented according to a method that employs a generally known algorithm. For example, if a degree of the difference of one frame image depicting cells from an adjoining one exceeds a certain degree, the frame image is removed but not displayed. Data of a previous frame image is held and kept displayed.

Referring to the flowchart of FIG. 48, operations to be performed will be described below.

The operations are analogous to those described in the flowchart of FIG. 37. The same step numbers as those in FIG. 37 will therefore be employed.

Similarly to FIG. 37, at the first step S71, the control device 124 waits for the start of scanning. At the next step S125, the control device 124 waits until designation of blur correction is validated. After designation of blur correction is validated, control is passed to step S72. Thereafter, step S78 to step S81 are executed.

After the completion of step S81, the control device 124 judges whether blur correction is canceled or scanning is stopped. If not, control is passed to step S77 of processing the next frame image. Control is then returned to step S78.

On the other hand, if blur correction is canceled or scanning is stopped, the control device 124 passes control to step S82 of stopping display and preservation. Thereafter, steps S83 and S84 are executed, and the process described in FIG. 48 is terminated.

FIG. 49 is the timing chart indicating the timings of the foregoing operations. Namely, after scanning is started, display and preservation are started at the timing that blur correction is executed. Thereafter, if blur correction is canceled, display and preservation are stopped at the timing.

As described above, according to the present embodiment, the settings or conditions for display and preservation can be determined, selected, or designated on the monitor 104 on which an observation image depicting cells and being produced by the optical scanning probe 102 is displayed. Only an image meeting the conditions can be displayed or preserved. This leads to improved user-friendliness (maneuverability).

Moreover, the designated conditions can be checked on the monitor 104. In other words, the designated conditions can be checked easily. This proves that the optical scanning probe system is user-friendly.

Moreover, a desired image can be preserved efficiently. Unlike the related art, unnecessary images will not be preserved. The necessity of editing or other work of sampling a desired still image from the unnecessary images is obviated or largely reduced.

Moreover, since unnecessary images are not preserved, a recording medium not having a large storage capacity may be adopted as the recording medium 118.

Ninth Embodiment

Figure 51:
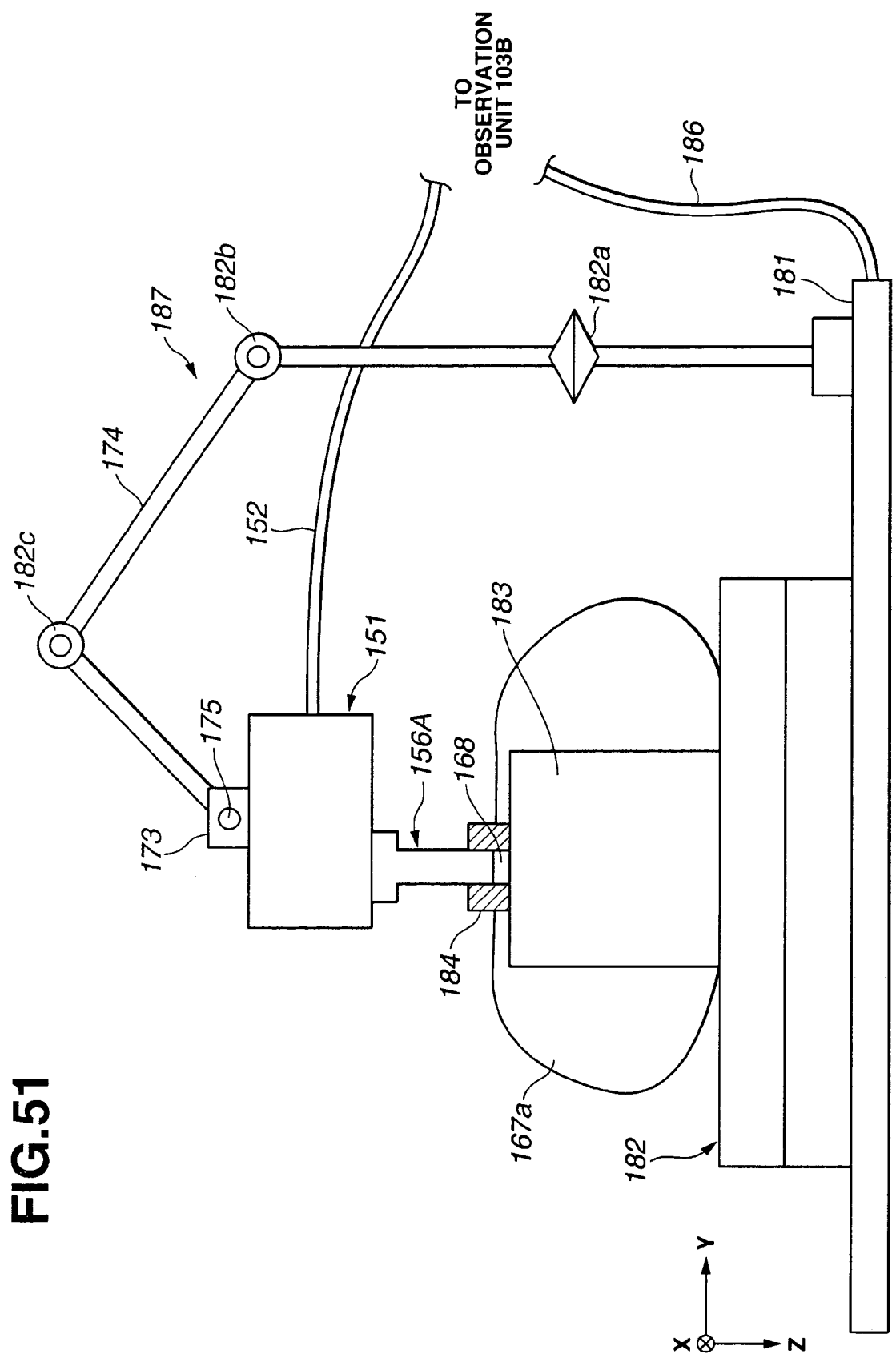

Next, referring to FIG. 50 and FIG. 51, a ninth embodiment of the present invention will be described below. FIG. 50 shows the internal configuration of an optical scanning probe of a rigid type included in an optical probe system in accordance with the ninth embodiment. FIG. 51 shows an example of use of the optical scanning probe.

An optical probe system 150 in accordance with the present embodiment adopts an optical scanning probe 151 of a rigid type shown in FIG. 50. The rigid-type optical scanning probe 151 comprises: a rigid probe housing 155 which is coupled to the distal end of a flexible sheath 152 (formed with a soft tube) and in which a focusing unit 153 and a two-dimensional scanning means 154 are incorporated; and objective units 156A and 156B that are selectively freely detachably attached to the probe housing 155.

The probe housing 155 is compact and lightweight, and one side of the probe housing 155 is several tens of millimeters long. Lens barrels 164 of the respective objective units 156A and 156B have an outer diameter of about several millimeters, for example, about three millimeters.

An optical fiber 157 and an electric cable 158 are passed through the sheath 152. A connector 105 is fixed to the proximal end of the sheath 152, and joined to a connector receptacle 106 of an observation apparatus 103B.

Luminous flux emanating from a light source unit included in the observation apparatus 103B and traveling over an optical fiber is incident on the optical fiber 157.

The luminous flux is propagated to the distal end of the optical fiber 157 over the optical fiber 157. The distal end of the optical fiber 157 is extended from the distal end of the sheath 152 to the probe housing 155. In the focusing unit 153, the distal end of the optical fiber 157 is held in a ferrule 159. The ferrule 159 is held so that it can be freely moved in the axial directions of the optical fiber 157 (Z directions in FIG. 50) indicated with arrows in FIG. 50 by means of a focusing drive unit 162 via a ferrule holding member 161.

The focusing drive unit 162 is designed to control the position of an actuator. The actuator is formed with, for example, a linear stage 162b having a motor 162a with an encoder. For example, the ferrule holding member 161 is borne by the movable section of the linear stage 162b so that it can be freely moved. With the rotation of a stepper motor 162a, the ferrule holding member 161 is moved in the axial directions of the optical fiber 157 via gears or the like that are not shown. In this case, a stroke the ferrule holding member 161 moves is, for example, about several millimeters, or more particularly, 5 mm. Moreover, the resolving power is about several micrometers, for example, 5 μm.

The actuator included in the focusing drive unit 162 may be realized with the combination of a stepper motor and a ball screw.

According to the present embodiment, the focusing unit 153 is designed so that the ferrule 159 included therein will be moved in the optical-axis directions. Alternatively, the focusing unit 153 may be designed to move a collimator lens 163 in the optical-axis directions. Specifically, the focusing drive unit 162 moves a member, which holds the collimator lens 163 and is not shown, instead of moving the ferrule holding member 161.

Moreover, the focusing unit 153 can shift a viewing point 168 in the optical-axis directions. Therefore, a tomographic image of an object of observation 167 in a depth direction can be produced.

Light emitted from the distal end of the optical fiber 157 is recomposed into parallel luminous fluxes by the collimator lens 163, and reflected from a two-dimensional scanning means 154 formed with a micro-machined mirror or the like. When the micro-machined mirror forming the two-dimensional scanning means 154 is two-dimensionally driven, the reflected luminous flux is two-dimensionally swept (in FIG. 50, in X and Y directions perpendicular to the axis of the optical fiber 157).

The luminous flux reflected from the two-dimensional scanning means 154 passes through an objective lens 166I locked in the distal part of the lens barrel 164 via a pupil lens relay 165 locked near the proximal end of the lens barrel 164 of an objective unit 156I (I corresponds to A or B). The light is then converged at and irradiated to the object of observation 167. At this time, the focusing unit 153 adjusts the focus of the optical scanning probe so that light will be focused on the viewing point 168 near the surface of the object of observation 167.

According to the present embodiment, the pupil lens relay 165 is locked in the objective unit 156I. Alternatively, the pupil lens relay 165 may be disposed in the probe housing 155 and separated from the objective unit 156I.

The probe housing 155 has an objective unit mount 169 fitted in an opening formed in a direction in which light is swept by the two-dimensional scanning means 154. The proximal part 170 of the lens barrel 164 included in the objective unit 156I is abutted on the objective unit mount 169, whereby the objective unit 156I is positioned and mounted.

Moreover, an ID detector 171 is opposed to the objective unit mount 169 with the proximal part 170 of the lens barrel 164 in the opening between them. The ID detector 170 detects a notch 172I formed in the proximal part 170 of the objective unit 156I, and thus verifies the power of the objective lens 166I.

The objective units 156A and 156B are different from each other in a point that, for example, the powers of the objective lenses 166A and 166B are different from each other. Moreover, the positions of the notches 172A and 172B are different from each other. The ID detector 171 detects the position of the notch 172A or 172B using an electric contact or an optical sensor. The ID detector 171 transmits an ID detection signal when it detects the position.

Instead of distinguishing an objective unit from another according to a mechanical difference between, for example, the notches 172A and 172B, ID information may be electrically read from a recording medium, a storage device (for example, a ROM), or the like in which ID information is stored.

The electric cable 158 comprises a drive line 158A over which the focusing drive unit 162 is driven, a drive line 158B over which the two-dimensional scanning means 154 is driven, and a signal line 158C over which the ID detection signal produced by the ID detector 171 is transmitted. When the connector 105 is coupled to the observation apparatus 103B, the electric cable 158 is coupled to a control device incorporated in the observation apparatus 103B.

The control device incorporated in the observation apparatus 103B has the same capability as the control device 124 shown in FIG. 27. In addition, the control device has the capability to produce a driving signal for use in focusing, and the capability to control a scanned range in case the two-dimensional scanning means 154 is driven based on the ID detection signal produced by the ID detector 171.

For example, assume that the power of the objective lens 166A locked in the objective unit 156A is four times higher than the power of the objective lens 166B locked in the objective unit 156B. Based on the ID detection signal produced when the objective unit 156A is mounted, the amplitude of a light wave to be swept by the two-dimensional scanning means 154 is controlled to be a quarter of the one of a signal applied when the objective unit 156B is mounted.

Light two-dimensionally swept by the two-dimensional scanning means 154 is converged on the objective lens 166A, and reflected from near the viewing point 168. The light then passes through the objective lens 166A and falls on the distal end of the optical fiber 157. The light is then photoelectrically converted within the observation apparatus 103B, whereby an image signal is produced. Consequently, an image represented by the image signal is displayed on a monitor connected to the observation apparatus 103B.

Even in the present embodiment, the distal end of the optical fiber 157 and the objective lens 166I (that converges light at the viewing point 168) have a nearly confocal relationship to each other, whereby a confocal microscope is realized.

Focusing is finely performed so that light will be focused on the viewing point 168 even after observation is continuously performed for a long period of time ranging from several weeks to several months. The focusing is adjustment of the focus of the optical scanning probe in a depth direction (or distance direction) orthogonal to directions in which two-dimensional scanning is performed.

An arm fixture 173 is formed on the external surface of the probe housing 155. As shown in FIG. 51, a passive joint 175 fixed to the distal end of an arm 174 is attached to the arm fixture 173.

FIG. 51 shows an example of use mainly of the optical scanning probe 151 included in the optical probe system 150 in accordance with the present embodiment. The optical scanning probe 151 is held at any position with the arm 174 whose proximal end is fixed to an observation table 181. The arm 174 has first to third joints 182a to 182c, which can freely swivel, arranged in the longitudinal direction of the arm 174. The position of the distal passive joint 175 at which the optical scanning probe 151 is held can be three-dimensionally adjusted or set to any position.

The first joint 182a can freely swivel in the axial directions of the arm 174, while the second and third joints 182b and 182c can freely swivel in directions orthogonal to the axis of the arm 174.

An XY stage 182 that is freely movable in X and Y directions is mounted on the observation table 181. An object-of-observation locking unit 183 shaped like, for example, letter U is secured to the XY stage 182.

The object-of-observation locking unit 183 clamps or locks, for example, a rat 167a that is the object of observation 167 as if to grasp it.

Moreover, an objective unit locking member 184 that locks the distal side of the objective unit 156I as if to grasp it is placed on the top of the object-of-observation locking unit 183 (in FIG. 51, the objective unit 156A).

A driving means such as a stepper motor that is not shown is incorporated in the XY stage 182. One end of the electric cable 186 extended from the observation table 181 is coupled to the driving means, and the other end thereof is coupled to the observation apparatus 103B.

The keyboard 125 (see FIG. 27) included in the observation apparatus 103B is handled in order to control driving by the stepper motor using a control signal produced by the control device 124. The position of the XY stage 182 (the position of the object-of-observation locking member 183 on the top of the XY stage) is adjusted arbitrarily on an XY plane by freely moving the XY stage 182 in the directions of two axes such as in the X and Y directions.

The object-of-observation locking member 183 on the top of the XY stage 182 is used to position the objective unit 156A of the rigid-type optical scanning probe 151. Thus, the object of observation 167, for example, the rat 167a can be observed for a prolonged period of time. When the object of observation 167 is thus observed for a prolonged period of time, the XY stage 182 is moved in order to finely adjust the position of the viewing point 168.

According to the present embodiment, an object of observation can be observed for a long period of time by performing simple work as if it were observed using a confocal microscope.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An optical probe system comprising:
   an optical probe to be inserted into a body cavity;
   a light source that generates lights which is irradiated to an object;
   a high-magnification observation unit incorporated in the distal section of the optical probe;
   an image digtization unit that digitizes a luminance signal produced by the high-magnification observation unit;
   an image parameter sampling unit that samples an image parameter from an image;
   an optimization parameter calculation unit that calculates an optimization parameter on the basis of the image parameter;
   an image optimization unit that optimizes an image according to the optimization parameter;
   an image display device on which an optimized image is displayed;
   a digital image preservation unit in which a digital image is preserved;
   a display/preservation selection device that is used to select or designate display/reservation parameters, which determine displaying and preserving an image, on the image display device, and wherein the display/preservation parameters include at least one of:
a parameter concerning display/preservation mode in which at least a specific image is displayed and/or preserved;
a parameter concerning a reference for selection based on which an image to be displayed on the image device, that is, an object of display and/or preservation is specified;
a parameter concerning simultaneously preserved data, that is, data other than an image that should be preserved together with an image displayed on the image display device;
a parameter concerning timing of preservation, that is, at what timing an image displayed on the image display device should be preserved; and
a parameter concerning blur correction, that is, whether a blur in an image displayed on the image display device should be corrected; and
a control device that controls any one of the light source, image display device, and digital image preservation unit on the basis of the display/preservation parameters, and executed display and preservation;
wherein the display/preservation selection device is used to select or designate the reference for selection from among:
a luminance value represented by a luminance signal sampled by the high-magnification observation unit;
an area that is defined within an image range produced by the high-magnification observation unit;
a frame image that specifies a certain number of frame images from among time-sequentially consecutive frame images; and
a time during which a specific frame image out of time-sequentially consecutive frame images is displayed or preserved.

2. An optical scanning probe system according to claim 1, wherein the control device controls the image display device and digital image preservation unit so that
an image whose luminance value is equal to or larger than a predetermined luminance value will be displayed and/or preserved; and
an image whose luminance value falls below the predetermined luminance value is not displayed and/or preserved.

3. An optical scanning probe system according to claim 2, wherein the control device controls the image display device and digital image preservation unit so that
when the reference for selection is set to the luminance value, an image whose luminance value is equal to or larger than to predetermined luminance value and which depicts an object in a size equal to or larger than a predetermined size will be displayed and/or preserved; and
an image whose luminance value falls below the predetermined luminance value and which depicts an object in a size falling below the predetermined size will not be displayed and/or preserved.

4. An optical scanning probe system according to claim 2, wherein when the reference for selection is set to the luminance value, the display/preservation selection device can be used to set the predetermined luminance value to any value.

5. An optical scanning probe system according to claim 2, wherein when the reference for selection is set to the luminance value, the display/preservation selection device can be used to set the predetermined luminance value and predetermined object size to any values.

6. An optical scanning probe system according to claim 1, wherein the control device controls the image display device and digital image preservation unit so that when the reference for selection is set to the area, a predetermined area alone will be displayed and/or preserved but the other area will not be displayed and/or preserved.

7. An optical scanning probe system according to claim 6, wherein when the reference for selection is set to the area, the display/preservation selection device can be used to set that predetermined area to any area.

8. An optical scanning probe system according to claim 1, wherein when the reference for selection is set to the frame image, the control device controls the image display device and digital image preservation unit so that a predetermined frame image alone will be displayed and/or preserved but the other frame images will not be displayed and/or preserved.

9. An optical scanning probe system according to claim 8, wherein when the reference for selection is set to the time, the display/preservation selection device can be used to set the predetermined frame image to any frame image.

10. An optical scanning probe system according to claim 1, wherein when the reference for selection is set to the time, the control device controls the image display device and digital image preservation unit so that display and/or preservation is performed during a predetermined time but not performed during the other time.

11. An optical scanning probe system according to claim 10, wherein when the reference for selection is set to the time, the display/preservation selection device can be used to set the predetermined time to any time.

12. An optical probe system comprising:
an optical probe to be inserted into a body cavity;
a light source that generates light which is irradiated to an object;
a high-magnification observation unit incorporated in the distal section of the optical probe;
an image digitization unit that digitizes a luminance signal produced by the high-magnification observation unit;
an image parameter sampling unit that samples an image parameter from an image;
an optimization parameter calculation unit that calculates an optimization parameter on the basis of the image parameter;
an image optimization unit that optimizes an image according to the optimization parameter;
an image display device on which an optimized image is displayed;
a digital image preservation unit in which a digital image is preserved;
a display/preservation selection device that is used to select or designate display/preservation parameters, which determine displaying an preserving an image, on the image display device, and wherein the display preservation parameters include at least one of;
a parameter concerning a display/reservation mode in which at least a specific image is displayed and/or preserved;
a parameter concerning a reference for selection based on which an image to be displayed on the image display device, that is an object of display and/or preservation is specified;

a parameter concerning simultaneously preserved data, that is, data other than an image that should be preserved together with an image displayed on the image display device;

a parameter concerning, timing of preservation, that is, at what timing an image displayed on the image display device should be preserved; and a parameter concerning blur correction, that is, whether a blur in an image displayed on the image display device should be corrected; and a control device that controls any one of the light source, image display device, and digital image preservation unit on the basis of the display/preservation parameters, and executes display and preservation;

wherein the display/preservation selection device can be used to select or designate the simultaneously preserved data from at least one and more among a normal endoscopic image, a scale, any text, and any cursor.

13. An optical probe system comprising:

an optical probe to be inserted into a body cavity;

a light source that generates light which is irradiated to an object;

a high-magnification observation unit incorporated in the distal section of the optical probe;

an image digitization unit that digitizes a luminance signal produced by the high-magnification observation unit;

an image parameter sampling unit that samples an image parameter from an image;

an optimization parameter calculation unit that calculates an optimization parameter on the basis of the image parameter;

an image optimization unit that optimizes an image according to the optimization parameter;

an image display device on which an optimized image is displayed;

a digital image preservation unit in which a digital image is preserved;

a display/preservation selection device that is used to select or designate display/preservation parameters, which determine display and preserving an image, on the image display device, and wherein the display/preservation parameters include at least one of:

a parameter concerning a display/preservation made in which at least a specific image is displayed and/or preserved;

a parameter concerning a reference for selection based on which an image to be displayed on the image display device, that is, an object of display and/or preservation is specified;

a parameter concerning simultaneously preserved data, that is, data other than an image that should be preserved together with an image displayed on the image display device;

a parameter concerning timing of preservation, that is, at what timing an image displayed on the image display device should be preserved; and a parameter concerning blur correction, that is whether a blur in an image displayed on the image display device should be corrected; and a control device that controls any one of the light source, image display device, and digital image preservation unit on the basis of the display/preservation parameters and executes display and preservation;

wherein the display/preservation selection device can be used to select or designate the timing of preservation from among:

the timing of starting and/or stopping observation which is determined by the control device;

the timing of displaying a still image or the timing before or after the display;

the timing of starting and/or stopping emission of light from the light source which is determined by the control device; and the timing of executing and/or canceling blur correction which is determined by the control device.

14. An optical probe comprising:

an optical probe to be inserted into a body cavity;

a light source that generates light which is irradiated to an object;

a high-magnification observation unit incorporated in the distal section of the optical probe;

an image digitization unit that digitizes a luminance signal produced by the high-magnification observation unit;

an image parameter sampling unit that samples an image parameter from an image;

an optimization parameter calculation unit that calculates an optimization parameter on the basis of the image parameter;

an image optimization unit that optimizes an image according to the optimization parameter;

an image display device on which an optimized image is displayed;

a digital image preservation unit in which a digital image is preserved;

a display/preservation selection device that is used to select or designate display/preservation parameters, which determine displaying and preserving an image, on the image display device, and wherein the display/preservation parameters include at least one of;

a parameter concerning a display/preservation mode in which at least a specific image is displayed and/or preserved;

a parameter concerning a reference for selection based on which an image to be displayed on the image display device, that is, an object of display and/or preservation is specified;

a parameter concerning simultaneously preserved data, that is, data other than an image that should be preserved together with an image displayed on the image display device;

a parameter concerning timing of preservation, that is, at what timing an image displayed on the image display device should be preserved; and a parameter concerning blur correction, that is, whether a blur in an image displayed on the image display device should be corrected; and a control device that controls any one of the light source, image display device, and digital image preservation unit on the basis of the display/preservation parameters, and executes display and preservation;

wherein the display/preservation selection device can be used to designate execution or cancellation of blur correction.

* * * * *